United States Patent
Maetzke et al.

(10) Patent No.: US 7,605,111 B2
(45) Date of Patent: Oct. 20, 2009

(54) HERBICIDES

(75) Inventors: Thomas Maetzke, Münchenstein (CH);
André Stoller, Blotzheim (FR);
Sebastian Wendeborn, Binningen (CH);
Henry Szczepanski, Wallbach (CH)

(73) Assignee: Syngenta Crop Protection, Inc.,
Greensboro, NC (US)

( * ) Notice: Subject to any disclaimer, the term of this patent is extended or adjusted under 35 U.S.C. 154(b) by 595 days.

(21) Appl. No.: 11/083,415

(22) Filed: Mar. 18, 2005

(65) Prior Publication Data

US 2005/0164883 A1 Jul. 28, 2005

Related U.S. Application Data

(62) Division of application No. 10/070,767, filed on Jun. 25, 2002, now Pat. No. 6,894,005.

(51) Int. Cl.
*A01N 31/06* (2006.01)
*C07D 321/00* (2006.01)

(52) U.S. Cl. ............... 504/218; 504/221; 504/223; 504/235; 504/238; 504/254; 504/269; 504/348; 549/200

(58) Field of Classification Search .............. 549/200; 504/218, 221, 223, 235, 238, 254, 269, 348
See application file for complete search history.

(56) References Cited

U.S. PATENT DOCUMENTS

| | | | |
|---|---|---|---|
| 4,834,908 A | 5/1989 | Hazen et al. |
| 5,683,965 A | 11/1997 | Bachmann et al. |
| 6,221,810 B1 | 4/2001 | Kruger et al. |
| 6,410,480 B1 | 6/2002 | Muhlebach et al. |
| 6,555,499 B1 | 4/2003 | Glock et al. |
| 6,962,894 B1 | 11/2005 | Glock |
| 2005/0164886 A1 | 7/2005 | Glock |
| 2005/0187110 A1 | 8/2005 | Maetzke et al. |

FOREIGN PATENT DOCUMENTS

| | | |
|---|---|---|
| DE | 3939503 A1 | 6/1991 |
| DE | 4331448 A1 | 3/1995 |
| DE | 19728568 A1 | 1/1998 |
| EP | 0 508 126 | 10/1992 |
| EP | 0508126 A1 | 10/1992 |
| WO | 9611574 A1 | 4/1996 |
| WO | 9621652 A1 | 7/1996 |
| WO | WO 96 25395 | 8/1996 |
| WO | 9813361 A1 | 4/1998 |
| WO | 9916744 A1 | 4/1999 |
| WO | 9947525 A1 | 9/1999 |
| WO | 0030447 A1 | 6/2000 |
| WO | 0047585 A1 | 8/2000 |
| WO | WO 00 78712 | 12/2000 |
| WO | 0117351 A1 | 3/2001 |
| WO | 03067984 A1 | 8/2003 |

OTHER PUBLICATIONS

Glock, J., "Herbicidal Composition", U.S. Appl. No. 10/070,936, Aug. 9, 2002.

*Primary Examiner*—James O. Wilson
*Assistant Examiner*—Paul V. Ward
(74) *Attorney, Agent, or Firm*—James Cueva

(57) ABSTRACT

Compounds of formula

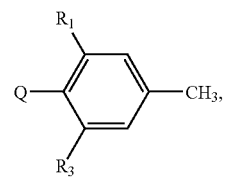

(I)

wherein the substituents have the meanings given in claim 1, and agronomically tolerable salts, isomers and enantiomers of those compounds, are suitable for use as herbicides.

5 Claims, No Drawings

HERBICIDES

This application is a divisional application of U.S. Ser. No. 10/070,767, filed Jun. 25, 2002 now U.S. Pat. No. 6,894,005, the contents of which are incorporated herein by reference.

The present invention relates to novel herbicidally active heterocycles substituted by a phenyl group, to processes for the preparation thereof, to compositions comprising such compounds, and to the use thereof in controlling weeds, especially in crops of useful plants, or in inhibiting plant growth.

3-Hydroxy-4-aryl-5-oxo-pyrazoline derivatives having herbicidal action are described, for example, in EP-A-0 508 126, WO 96/25395 and WO 96/21652.

Novel heterocycles substituted by a phenyl group having herbicidal and growth-inhibiting properties have now been found.

The present invention accordingly relates to compounds of formula I

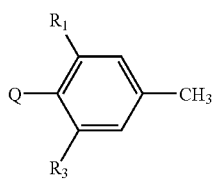
(I)

wherein $R_1$ and $R_3$ are each independently of the other ethyl, haloethyl, ethynyl, $C_1$-$C_2$alkoxy, $C_1$-$C_2$haloalkoxy, $C_1$-$C_2$alkylcarbonyl, $C_1$-$C_2$hydroxyalkyl or $C_1$-$C_2$alkoxycarbonyl;

Q is a group

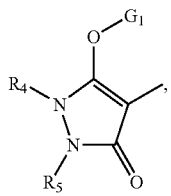
(Q1)

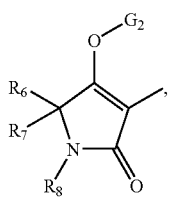
(Q2)

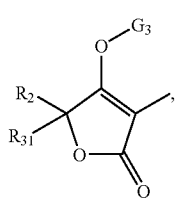
(Q3)

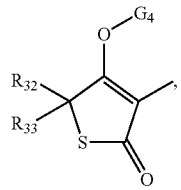
(Q4)

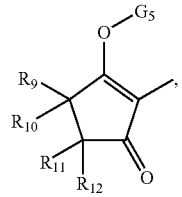
(Q5)

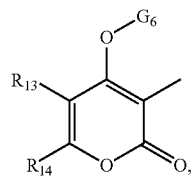
(Q6)

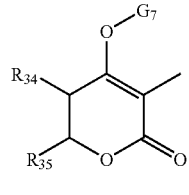
(Q7)

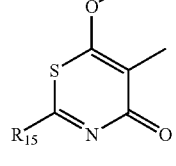
(Q8)

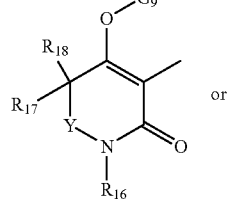
(Q9)

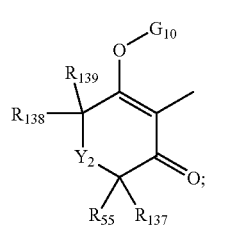
(Q10)

$R_4$ and $R_5$ are each independently of the other $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_2$-$C_{10}$-N-alkoxyiminoalkyl, $C_2$-$C_{10}$alkoxycarbonylalkyl, $C_1$-$C_{10}$aminoalkyl, $C_3$-$C_{10}$dialkylaminoalkyl, $C_2$-$C_{10}$alkylaminoalkyl, $C_1$-$C_{10}$cyanoalkyl, $C_4$-$C_{10}$cycloalkylalkyl, $C_1$-$C_{10}$phenylalkyl, $C_1$-$C_{10}$heteroarylalkyl, $C_1$-$C_{10}$phenoxyalkyl, $C_1$-$C_{10}$heteroaryloxyalkyl, $C_1$-$C_{10}$alkylideneaminooxyalkyl, $C_1$-$C_{10}$nitroalkyl, $C_1$-$C_{10}$trialkylsilylalkyl, $C_2$-$C_{10}$alkylaminocarbonylalkyl, $C_2$-$C_{10}$dialkylaminocarbonylalkyl, $C_2$-$C_{10}$alkylaminocarbonyloxyalkyl, $C_3$-$C_{10}$dialkylaminocarbonyloxalkyl, $C_2$-$C_{10}$alkoxycarbonylaminoalkyl, $C_1$-$C_{10}$-N-alkoxycarbonyl-N-alkylaminoalkyl, $C_1$-$C_{10}$cycloalkyl, aryl or heteroaryl; or $R_4$ and $R_5$, together with the atoms to which they are bonded, form a 5- to 7-membered cyclic group that may contain one or two hetero atoms selected from nitrogen, oxygen and sulfur and that, in addition, may contain a fused or spiro-bound alkylene or alkenylene chain consisting of from 2 to 6 carbon atoms, which chain may in turn contain one or two hetero atoms selected from oxygen and sulfur, wherein the cyclic group may be substituted by phenyl or benzyl, which in turn may be substituted by halogen, $C_1$-$C_6$alkyl, $C_1$-$C_6$haloalkyl, $C_3$-$C_6$cycloalkyl, hydroxy, $C_1$-$C_6$alkoxy, $C_1$-$C_6$alkoxy-$C_1$-$C_6$alkoxy, $C_1$-$C_6$haloalkoxy or by nitro;

$R_2$, $R_6$ and $R_{32}$ are each independently of the others $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_3$-$C_{10}$cycloalkyl, aryl or heteroaryl;

$R_7$, $R_{31}$ and $R_{33}$ are each independently of the others hydrogen, $C_1$-$C_{10}$alkyl, $C_2$-$C_{10}$alkenyl, $C_2$-$C_{10}$alkynyl or $C_2$-$C_{10}$alkoxyalkyl;

$R_8$ is hydrogen, $C_1$-$C_{10}$alkyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_3$-$C_{10}$cycloalkyl, aryl or heteroaryl; or $R_6$ and $R_7$ or $R_2$ and $R_{31}$ or $R_{32}$ and $R_{33}$, together with the atom to which they are bonded, form a saturated 3- to 7-membered cyclic group that may contain one or two hetero atoms selected from nitrogen, oxygen and sulfur; or $R_6$ and $R_8$, together with the atoms to which they are bonded, form a 5- to 7-membered cyclic group that may contain one or two hetero atoms selected from nitrogen, oxygen and sulfur;

$R_9$, $R_{10}$, $R_{11}$ and $R_{12}$ are each independently of the others $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_3$-$C_{10}$cycloalkyl, aryl or heteroaryl; or $R_9$ and $R_{11}$ or $R_9$ and $R_{10}$, together with the atoms to which they are bonded, form a 5- to 7-membered cyclic group that may contain one or two hetero atoms selected from nitrogen, oxygen and sulfur;

$R_{13}$, $R_{14}$, $R_{34}$ and $R_{35}$ are each independently of the others $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_3$-$C_{10}$cycloalkyl, aryl or heteroaryl; or $R_{13}$ and $R_{14}$ or $R_{34}$ and $R_{35}$, together with the atoms to which they are bonded, form a 5- to 7-membered cyclic group that may contain one or two hetero atoms selected from nitrogen, oxygen and sulfur;

$R_{15}$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_2$-$C_{10}$alkoxycarbonylalkyl, $C_1$-$C_{10}$aminoalkyl, $C_3$-$C_{10}$dialkylaminoalkyl, $C_2$-$C_{10}$alkylaminoalkyl, $C_1$-$C_{10}$cyanoalkyl, $C_4$-$C_{10}$cycloalkylalkyl, $C_1$-$C_{10}$phenylalkyl, $C_1$-$C_{10}$heteroarylalkyl, $C_1$-$C_{10}$phenoxyalkyl, $C_1$-$C_{10}$heteroaryloxyalkyl, $C_1$-$C_{10}$nitroalkyl, $C_3$-$C_{10}$cycloalkyl, aryl or heteroaryl;

$R_{16}$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthiolkyl, $C_2$-$C_{10}$alkylsulfinylalkyl, $C_2$-$C_{10}$alkylsulfonylalkyl, $C_3$-$C_{10}$cycloalkyl, aryl or heteroaryl;

$R_{17}$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_3$-$C_{10}$cycloalkyl, aryl or heteroaryl;

$R_{18}$ is hydrogen, $C_2$-$C_{10}$alkenyl, $C_2$-$C_{10}$alkynyl, $C_1$-$C_{10}$alkyl or $C_1$-$C_{10}$alkoxyalkyl; or $R_{17}$ and $R_{18}$, together with the atoms to which they are bonded, form a 3- to 7-membered cyclic group that may contain one or two hetero atoms selected from nitrogen, oxygen and sulfur;

Y is oxygen, sulfur, C—$R_{19}$ or N—$R_{36}$;

$R_{19}$ and $R_{36}$ are each independently of the other $C_1$-$C_{10}$alkyl, $C_1$-$C_{10}$haloalkyl, phenyl or heteroaryl; or $R_{18}$ and $R_{19}$ or $R_{18}$ and $R_{36}$, together with the atom to which they are bonded, form a saturated 5- to 7-membered cyclic group that may contain one or two hetero atoms selected from nitrogen, oxygen and sulfur;

$G_1$, $G_2$, $G_3$, $G_4$, $G_5$, $G_6$, $G_7$, $G_8$, $G_9$ and $G_{10}$ are each independently of the others hydrogen, —C($X_1$)—$R_{20}$, —C($X_2$)—$X_3$—$R_{21}$, —C($X_4$)—N($R_{22}$)—$R_{23}$, —SO$_2$—$R_{24}$, an alkali metal cation, alkaline earth metal cation, sulfonium cation or ammonium cation, —P($X_5$)($R_{25}$)—$R_{26}$ or —CH$_2$—$X_6$—$R_{27}$;

$X_1$, $X_2$, $X_3$, $X_4$, $X_5$ and $X_6$ are each independently of the others oxygen or sulfur;

$R_{20}$, $R_{21}$, $R_{22}$ and $R_{23}$ are each independently of the others hydrogen, $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfoxyl-$C_1$-$C_5$alkyl, $C_1$-$C_5$alkylsulfonyl-$C_1$-$C_5$alkyl, $C_2$-$C_8$alkylideneaminooxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$aminocarbonyl-$C_1$-$C_5$alkyl, $C_2$-$C_8$dialkylaminocarbonyl-$C_1$-$C_5$alkyl, $C_1$-$C_5$alkylcarbonylamino-$C_1$-$C_5$alkyl, $C_1$-$C_5$alkylcarbonyl-($C_2$-$C_5$alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino, or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, phenylamino, or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or $C_3$-$C_7$cycloalkylamino, di-$C_3$-$C_7$cycloalkylamino or $C_3$-$C_7$cycloalkoxy;

$R_{24}$, $R_{25}$ and $R_{26}$ are hydrogen, $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfoxyl-$C_1$-$C_5$alkyl, $C_1$-$C_5$alkylsulfonyl-$C_1$-$C_5$alkyl, $C_2$-$C_8$alkylideneaminooxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$aminocarbonyl-$C_1$-$C_5$alkyl, $C_2$-$C_8$dialkylaminocarbonyl-$C_1$-$C_5$alkyl, $C_1$-$C_5$alkylcarbonylamino-$C_1$-$C_5$alkyl, $C_1$-$C_5$alkylcarbonyl-($C_2$-$C_5$alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino, or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, phenylamino, or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or $C_3$-$C_7$cycloalkylamino, di-$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino, $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{27}$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfoxyl-$C_1$-$C_5$alkyl, $C_1$-$C_5$alkylsulfonyl-$C_1$-$C_5$alkyl, $C_2$-$C_8$alkylideneaminooxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$aminocarbonyl-$C_1$-$C_5$alkyl, $C_2$-$C_8$dialkylaminocarbonyl-$C_1$-$C_5$alkyl, $C_1$-$C_5$alkylcarbonylamino-$C_1$-$C_5$alkyl, $C_1$-$C_5$alkylcarbonyl-($C_2$-$C_5$alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino, diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or phenylamino, phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, $C_3$-$C_7$cycloalkylamino, di-$C_3$-$C_7$cycloalkylamino, $C_3$-$C_7$cycloalkoxy or $C_1$-$C_{10}$alkylcarbonyl;

$Y_2$ is oxygen, sulfur, C—$R_{140}$—$R_{141}$ or N—$R_{142}$, $R_{55}$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_3$-$C_{10}$cycloalkyl, aryl or heteroaryl;

$R_{137}$ is hydrogen, $C_1$-$C_{10}$alkyl, $C_2$-$C_{10}$alkenyl, $C_2$-$C_{10}$alkynyl or $C_1$-$C_{10}$alkoxyalkyl; or $R_{55}$ and $R_{137}$, together with the atoms to which they are bonded, form a 3- to 7-membered cyclic group that may contain one or two hetero atoms selected from nitrogen, oxygen and sulfur;

$R_{138}$ and $R_{139}$ are each independently of the other hydrogen, $C_1$-$C_{10}$alkyl, $C_2$-$C_{10}$alkenyl, $C_2$-$C_{10}$alkynyl or $C_2$-$C_{10}$alkoxyalkyl; and $R_{140}$ and $R_{141}$ are each independently of the other hydrogen, $C_1$-$C_{10}$alkyl, $C_2$-$C_{10}$alkenyl, $C_2$-$C_{10}$alkynyl or $C_1$-$C_{10}$alkoxyalkyl; or $R_{55}$ and C—$R_{140}$, together with the atoms to which they are bonded, form a saturated or unsaturated 3- to 7-membered cyclic group that may contain one or two hetero atoms selected from nitrogen, oxygen and sulfur;

$R_{142}$ is hydrogen, $C_1$-$C_{10}$alkyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_3$-$C_{10}$cycloalkyl, aryl or heteroaryl; or $R_{55}$ and N—$R_{142}$, together with the atoms to which they are bonded, form a saturated or unsaturated 3- to 7-membered cyclic group that may contain one or two hetero atoms selected from nitrogen, oxygen and sulfur;

and also to agronomically tolerable salts, isomers and enantiomers of those compounds.

The alkyl groups occurring in the substituent definitions may be straight-chain or branched and are, for example, methyl, ethyl, n-propyl, isopropyl, n-butyl, sec-butyl, isobutyl, tert-butyl and the isomers of pentyl, hexyl, heptyl, octyl, nonyl and decyl. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl or dichlorofluoromethyl. Alkoxyalkyl is, for example, methoxymethyl, ethoxymethyl, propoxyethyl, isopropoxyethyl, n-butoxymethyl, isobutoxy-n-butyl, sec-butoxymethyl and tert-butoxyisopropyl, preferably methoxymethyl and ethoxymethyl. Alkoxy, alkenyl, alkynyl, alkoxyalkyl, alkylthio, alkylsulfonyl, alkylaminocarbonyl, dialkylaminocarbonyl, alkylaminoalkyl, phenylalkyl, nitroalkyl, aminoalkyl and N-alkoxycarbonyl-N-alkylaminoalkyl groups are derived from the mentioned alkyl radicals. The alkenyl and alkynyl groups may be mono- or poly-unsaturated. Alkenyl is to be understood as meaning, for example, vinyl, allyl, methallyl, 1-methylvinyl or but-2-en-1-yl. Alkynyl is, for example, ethynyl, propargyl, but-2-yn-1-yl, 2-methylbutyn-2-yl or but-3-yn-2-yl. Alkynyl is, for example, ethynyl, propargyl, but-2-yn-1-yl, 2-methylbutyn-2-yl or but-3-yn-2-yl. Haloalkyl groups preferably have a chain length of from 1 to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl or 2,2,2-trichloroethyl; preferably trichloromethyl, difluorochloromethyl, difluoromethyl, trifluoromethyl or dichlorofluoromethyl. Suitable haloalkenyl groups include alkenyl groups mono- or poly-substituted by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Of the $C_2$-$C_6$alkenyl groups mono-, di- or tri-substituted by halogen, preference is given to those having a chain length of from 3 to 5 carbon atoms. Alkoxy groups preferably have a chain length of from 1 to 6 carbon atoms. Alkoxy is, for example, methoxy, ethoxy, propoxy, isopropoxy, n-butoxy, isobutoxy,-sec-butoxy or tert-butoxy and the isomers of pentyloxy and hexyloxy; preferably methoxy and ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Alkylthio groups preferably have a chain length of from 1 to 4 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl or tert-butylsulfinyl; preferably methylsulfinyl or ethylsulfinyl. Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl. Alkylamino is, for example, methylamino, ethylamino, n-propylamino, isopropylamino or the butylamine isomers. Dialkylamino is, for example, dimethylamino, methylethylamino, diethylamino, n-propylmethylamino, dibutylamino or diisopropylamino. Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. Phenyl may be in substituted form. The substituents may in that case be in the ortho, meta and/or para position. Preferred substituents positions are the ortho and para positions relative to the point of attachment to the ring.

Aryl is, for example, phenyl or naphthyl. Those groups may also be substituted. When not specified otherwise in the definitions, phenyl, also as part of a substituent such as phenylalkyl, may, for example, be substituted by halogen, nitro, cyano, $C_1$-$C_4$alkyl, $C_1$-$C_4$alkoxy, $C_1$-$C_4$alkylthio, $C_1$-$C_4$alkylsulfoxy, $C_1$-$C_4$alkylsulfonyl, carboxyl, $C_1$-$C_4$alkoxycarbonyl, amino, $C_1$-$C_4$alkylamino, $C_1$-$C_4$dialkylamino or by $C_1$-$C_4$alkylcarbonylamino.

Heteroaryl groups are usually aromatic heterocycles that contain preferably from 1 to 3 hetero atoms, such as nitrogen, sulfur and oxygen. Examples of suitable heterocycles and heteroaromatic compounds include: pyrrolidine, piperidine, pyran, dioxane, azetidine, oxetane, pyridine, pyrimidine, triazine, thiazole, thiadiazole, imidazole, oxazole, isoxazole and also pyrazine, furan, morpholine, piperazine, pyrazole, benzoxazole, benzthiazole, quinoxaline and quinoline. Those heterocycles and heteroaromatic compounds may be further substituted, for example by halogen, alkyl, alkoxy, haloalkyl, haloalkoxy, nitro, cyano, thioalkyl, alkylamino or by phenyl.

Within the scope of the present invention, 3- to 7-membered cyclic groups are to be understood as meaning ring systems that, in addition to the hetero atoms that may already be present in the ring of the substituent Q, may contain, besides the carbon atoms, one or more hetero atoms, such as nitrogen, oxygen and/or sulfur. They may be saturated or unsaturated. The unsaturated bond may, for example in the group $Q_2$, be formed by the substituents $R_6$ and $R_7$. Preferably, such ring systems contain from 5 to 7 ring atoms. 3- to 7-membered cyclic groups, including the cycloalkyls, for example cyclopropyl, cyclobutyl, cyclopentyl, cyclohexyl, cycloheptyl or cyclooctyl, may also be substituted. Suitable substituents include halogen, hydroxy, nitro, cyano, $C_1$-$C_4$alkylcarbonyl, $C_1$-$C_4$alkoxycarbonyl, $C_1$-$C_4$alkyl, $C_1$-$C_4$haloalkyl, keto, $C_2$-$C_4$alkenyloxyimino, $C_1$-$C_4$alkoxy, $C_1$-$C_4$alkoxyalkoxy, $C_1$-$C_4$alkylthio, or one of the following three groups:

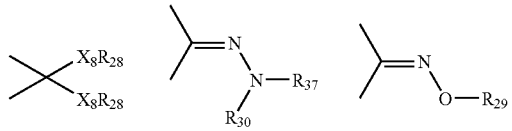

wherein $X_8$ is sulfur or oxygen, $R_{28}$ is $C_1$-$C_4$alkoxy or the two $R_{28}$ radicals, together with the —$X_8$—C—$X_8$— bridge to which they are bonded, form a 5- or 6-membered ring that may be substituted by methyl, ethyl, methoxy or by a keto group, $R_{29}$ is $C_1$-$C_4$alkyl, $C_1$-$C_4$haloalkyl, $C_2$-$C_4$alkenyl or $C_2$-$C_4$haloalkenyl, $R_{30}$ and $R_{37}$ are each independently of the other $C_1$-$C_4$alkyl, phenyl or $C_2$-$C_4$alkenyl, or $R_{30}$ and $R_{37}$, together with the nitrogen atom to which they are bonded, form a 5- or 6-membered ring that may contain a hetero atom selected from nitrogen, oxygen and sulfur.

In the substituent definitions, the number of carbon atoms is the total number of carbon atoms in the alkyl, alkenyl and alkynyl groups and the groups derived therefrom, for example haloalkyl or alkenyloxy. $C_2$-$C_3$Alkoxyalkyl accordingly comprises methoxymethyl, methoxyethyl and ethoxymethyl. $C_3$Alkoxycarbonylalkyl comprises methoxycarbonylethyl and ethoxycarbonylmethyl.

Alkali metal, alkaline earth metal or ammonium cations for the substituents $G_1$ to $G_{10}$ are, for example, the cations of sodium, potassium, magnesium, calcium and ammonium. Preferred sulfonium cations are especially trialkylsulfonium cations in which the alkyl groups preferably each contain from 1 to 4 carbon atoms.

Depending on the nature of the substituents, the compounds of formula I may also be in the form of geometric and/or optical isomers and mixtures of isomers as well as in the form of tautomers and mixtures of tautomers. The present invention relates also to those compounds of formula I. For example, the compounds of formula I wherein Q is $Q_1$ and the group $G_1$ is hydrogen may be present in the following tautomeric equilibria:

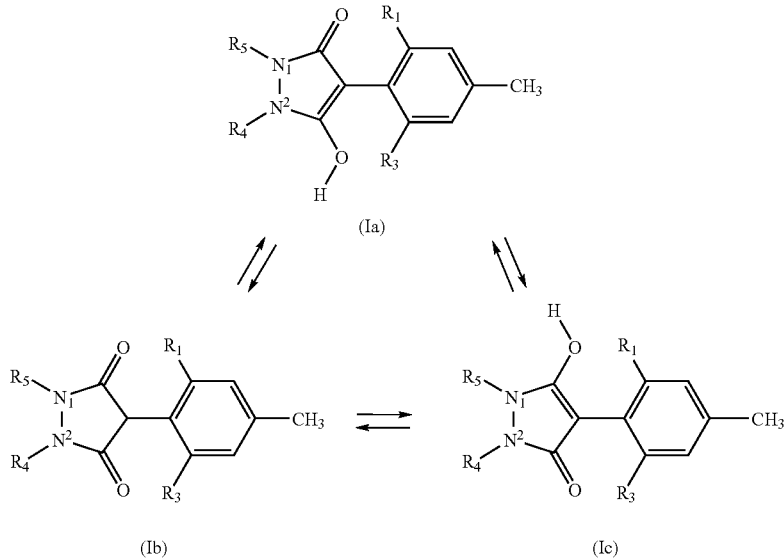

When $G_1$ to $G_{10}$ is other than hydrogen and the cyclic group formed by $R_4$ and $R_5$ together is asymmetrically substituted, fused or spiro-bound, for example the compound of formula I may be present in the form of an isomer of formula Id

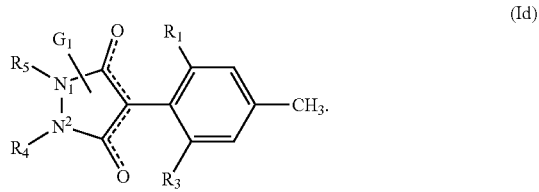

The invention likewise includes the salts that the compounds of formula I are able to form preferably with amines, alkali metal and alkaline earth metal bases or quaternary ammonium bases. Suitable salt formers are described, for example, in WO 98/41089.

The invention likewise includes the salts that the compounds of formula I are able to form with amines, alkali metal and alkaline earth metal bases or quaternary ammonium bases.

Of the alkali metal and alkaline earth metal hydroxides as salt formers, attention is drawn to the hydroxides of lithium, sodium, potassium, magnesium or calcium, but especially to those of sodium or potassium.

Examples of amines suitable for ammonium salt formation include both ammonia and also primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for the salt formation correspond, for example, to the formula $[N(R_aR_bR_cR_d)]OH$, wherein $R_a$, $R_b$, $R_c$ and $R_d$ are each independently of the others $C_1$-$C_4$ alkyl. Other suitable tetraalkylammonium bases having other anions can be obtained, for example, by anion exchange reactions.

Of the compounds of formula I, preference is given to those wherein Q is $Q_1$, $Q_2$, $Q_3$, $Q_4$, $Q_5$, $Q_6$, $Q_7$, $Q_8$ or $Q_9$.

Preference is given also to compounds of formula I wherein $R_4$ and $R_5$ are each independently of the other $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthioalkyl, $C_2$-$C_6$alkylsulfoxylalkyl, $C_2$-$C_6$alkylsulfonylalkyl, $C_2$-$C_6$alkylcarbonylalkyl, $C_3$-$C_6$-N-alkoxy-iminoalkyl, $C_3$-$C_6$alkoxycarbonylalkyl, $C_1$-$C_6$aminoalkyl, $C_2$-$C_6$dialkylaminoalkyl, $C_3$-$C_6$alkylaminoalkyl, $C_1$-$C_6$cyanoalkyl, $C_4$-$C_8$cycloalkylalkyl, $C_7$-$C_8$phenylalkyl, $C_7$-$C_8$heteroarylalkyl, $C_7$-$C_8$phenoxyalkyl, $C_7$-$C_8$heteroaryloxyalkyl, $C_4$-$C_6$alkylideneaminooxyalkyl, $C_1$-$C_6$nitroalkyl, $C_4$-$C_8$trialkylsilylalkyl, $C_4$-$C_6$alkylaminocarbonyl, $C_3$-$C_6$dialkylaminocarbonyl, $C_4$-$C_8$alkylaminocarbonyloxyalkyl, $C_4$-$C_8$dialkylaminocarbonyloxyalkyl, $C_4$-$C_8$alkoxycarbonylaminoalkyl, $C_4$-$C_8$-N-alkoxycarbonyl-N-alkylaminoalkyl, $C_3$-$C_8$cycloalkyl, aryl or heteroaryl, or $R_4$ and $R_5$, together with the atoms to which they are bonded, form a 5- to 7-membered cyclic group.

Preference is given also to compounds of formula I wherein $R_2$, $R_6$ and $R_{32}$ are each independently of the others $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthioalkyl, $C_2$-$C_6$alkylsulfoxylalkyl, $C_2$-$C_6$alkylsulfonylalkyl, $C_3$-$C_6$alkylcarbonylalkyl, $C_3$-$C_8$cycloalkyl, aryl or heteroaryl;

$R_7$, $R_{31}$ and $R_{33}$ are hydrogen, $C_1$-$C_6$alkyl or $C_1$-$C_6$alkoxyalkyl;

$R_8$ is hydrogen, $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_1$-$C_6$alkylthioalkyl, $C_1$-$C_6$alkylsulfinylalkyl, $C_1$-$C_6$alkylsulfonylalkyl, $C_3$-$C_8$cycloalkyl, aryl or heteroaryl; or $R_6$ and $R_7$ or $R_2$ and $R_{31}$ or $R_{32}$ and $R_{33}$, together with the atoms to which they are bonded, form a 5- to 7-membered cyclic group that may contain one or two hetero atoms selected from nitrogen, oxygen and sulfur, or $R_6$ and $R_8$, together with the atoms to which they are bonded, form a 5- to 7-membered cyclic group that may contain one or two hetero atoms selected from nitrogen, oxygen and sulfur;

$R_9$, $R_{10}$, $R_{11}$ and $R_{12}$ are each independently of the others $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthialkyl, $C_2$-$C_6$alkylsulfinylalkyl, $C_2$-$C_6$alkylsulfonylalkyl, $C_3$-$C_6$alkylcarbonylalkyl, $C_3$-$C_8$cycloalkyl, aryl or heteroaryl; or $R_9$ and $R_{11}$ or $R_9$ and $R_{10}$, together with the atoms to which they are bonded, form a 5- to 7-membered cyclic group that may contain one or two hetero atoms selected from nitrogen, oxygen and sulfur, or $R_9$ and $R_{10}$, together with the atom to which they are bonded, form a saturated 3- to 7-membered cyclic group that may contain one or two hetero atoms selected from nitrogen, oxygen and sulfur;

$R_{13}$, $R_{14}$, $R_{34}$ and $R_{35}$ are each independently of the others $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthioalkyl, $C_2$-$C_6$alkylsulfoxylalkyl, $C_2$-$C_6$alkylsulfonylalkyl, $C_3$-$C_6$alkylcarbonylalkyl, $C_3$-$C_8$cycloalkyl, aryl or heteroaryl; or $R_{13}$ and $R_{14}$ or $R_{34}$ and $R_{35}$, together with the atoms to which they are bonded, form a 5- to 7-membered cyclic group that may contain one or two hetero atoms selected from nitrogen, oxygen and sulfur, $R_{15}$ is $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthioalkyl, $C_2$-$C_6$alkylsulfoxylalkyl, $C_2$-$C_6$alkylsulfonylalkyl, $C_3$-$C_6$alkylcarbonylalkyl, $C_3$-$C_6$alkoxycarbonylalkyl, $C_2$-$C_6$aminoalkyl, $C_4$-$C_6$dialkylaminoalkyl, $C_4$-$C_6$alkylaminoalkyl, $C_2$-$C_6$cyanoalkyl, $C_3$-$C_8$cycloalkylalkyl, $C_7$-$C_8$phenylalkyl, $C_7$-$C_8$heteroarylalkyl, $C_7$-$C_8$phenoxyalkyl, $C_6$-$C_8$heteroaryloxyalkyl, $C_1$-$C_6$nitroalkyl, $C_3$-$C_8$cycloalkyl, aryl or heteroaryl;

$R_{16}$ is $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthiolkyl, $C_2$-$C_6$alkylsulfinylalkyl, $C_2$-$C_6$alkylsulfonylalkyl, $C_3$-$C_8$cycloalkyl, aryl or heteroaryl;

$R_{17}$ is $C_1$-$C_6$alkyl, $C_1$-$C_6$haloalkyl, $C_2$-$C_6$alkoxyalkyl, $C_4$-$C_6$alkenyloxyalkyl, $C_4$-$C_6$alkynyloxyalkyl, $C_2$-$C_6$alkylthialkyl, $C_2$-$C_6$alkylsulfinylalkyl, $C_2$-$C_6$alkylsulfonylalkyl, $C_3$-$C_6$alkylcarbonylalkyl, $C_3$-$C_8$cycloalkyl, aryl or heteroaryl;

$R_{18}$ is hydrogen, $C_1$-$C_6$alkyl or $C_2$-$C_6$alkoxyalkyl; or $R_{17}$ and $R_{18}$, together with the atoms to which they are bonded, form a 3- to 7-membered cyclic group that may contain one or two hetero atoms selected from nitrogen, oxygen and sulfur, $R_{19}$ and $R_{36}$ are each independently of the other $C_1$-$C_6$alkyl, $C_1$-$C_6$haloalkyl, phenyl or heteroaryl; or $R_{18}$ and $R_{19}$ or $R_{18}$ and $R_{36}$, together with the atom to which they are bonded, form a saturated 5- to 7-membered cyclic group that may contain one or two hetero atoms selected from nitrogen, oxygen and sulfur;

$R_{20}$, $R_{21}$, $R_{22}$, $R_{23}$ and $R_{27}$ are each independently of the others hydrogen, $C_1$-$C_8$alkyl, $C_1$-$C_8$haloalkyl, $C_1$-$C_8$cyanoalkyl, $C_1$-$C_8$nitroalkyl, $C_1$-$C_8$aminoalkyl, $C_1$-$C_5$alkylamino-$C_1$-$C_2$alkyl, $C_2$-$C_6$dialkylamino-$C_1$-$C_2$alkyl, $C_3$-$C_7$cycloalkyl-$C_1$-$C_2$alkyl, $C_2$-$C_8$alkoxyalkyl, $C_4$-$C_8$alkenyloxyalkyl, $C_4$-$C_8$alkynyloxyalkyl, $C_2$-$C_8$alkylthioalkyl, $C_1$-$C_2$alkylsulfoxyl-$C_1$-$C_2$alkyl, $C_1$-$C_2$alkylsulfonyl-$C_1$-$C_2$alkyl, $C_2$-$C_8$alkylideneaminooxy-$C_1$-$C_2$alkyl, $C_1$-$C_5$alkylcarbonyl-$C_1$-$C_2$alkyl, $C_1$-$C_5$alkoxycarbonyl-$C_1$-$C_2$alkyl, $C_1$-$C_5$amino-carbonyl-$C_1$-$C_2$alkyl, $C_2$-$C_8$dialkylaminocarbonyl-$C_1$-$C_2$alkyl, $C_1$-$C_5$alkylcarbonylamino-$C_1$-$C_2$alkyl, $C_1$-$C_2$alkylcarbonyl-N-$C_1$-$C_3$alkyl-$C_1$-$C_2$aminoalkyl, $C_3$-$C_6$-trialkylsilyl-$C_1$-$C_3$alkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_2$-$C_5$alkenyl, $C_2$-$C_5$haloalkenyl, $C_3$-$C_8$cycloalkyl, phenyl or heteroaryl;

$R_{24}$, $R_{25}$ and $R_{26}$ are each independently of the others hydrogen, $C_1$-$C_8$alkyl, $C_1$-$C_8$haloalkyl, $C_1$-$C_8$cyanoalkyl, $C_1$-$C_8$nitroalkyl, $C_1$-$C_8$aminoalkyl, $C_1$-$C_5$alkylamino-$C_1$-$C_2$alkyl, $C_2$-$C_6$dialkylamino-$C_1$-$C_2$alkyl, $C_3$-$C_7$cycloalkyl-$C_1$-$C_2$alkyl, $C_2$-$C_8$alkoxyalkyl, $C_4$-$C_8$alkenyloxyalkyl, $C_4$-$C_8$alkynyloxyalkyl, $C_2$-$C_8$alkylthioalkyl, $C_1$-$C_2$alkylsulfoxyl-$C_1$-$C_2$alkyl, $C_1$-$C_2$alkylsulfonyl-$C_1$-$C_2$alkyl, $C_2$-$C_8$alkylideneaminooxy-$C_1$-$C_2$alkyl, $C_1$-$C_5$alkylcarbonyl-$C_1$-$C_2$alkyl, $C_1$-$C_5$alkoxycarbonyl-$C_1$-$C_2$alkyl, $C_1$-$C_5$amino-carbonyl-$C_1$-$C_2$alkyl, $C_2$-$C_8$dialkylamino-carbonyl-$C_1$-$C_2$alkyl, $C_1$-$C_5$alkylcarbonylamino-$C_1$-$C_2$alkyl, $C_1$-$C_2$alkylcarbonyl-N-$C_1$-$C_3$alkyl-$C_1$-$C_2$aminoalkyl, $C_3$-$C_6$trialkylsilyl-$C_1$-$C_3$alkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_2$-$C_5$alkenyl, $C_2$-$C_5$haloalkenyl, $C_3$-$C_8$cycloalkyl, phenyl, heteroaryl, $C_1$-$C_6$alkoxy, $C_1$-$C_6$haloalkoxy, $C_1$-$C_3$alkylamino, $C_2$-$C_6$dialkylamino, or benzyloxy or phenoxy in which the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or by nitro; and $R_{27}$ is $C_1$-$C_8$alkyl, $C_1$-$C_8$haloalkyl, $C_1$-$C_8$cyanoalkyl, $C_1$-$C_8$nitroalkyl, $C_1$-$C_8$aminoalkyl, $C_1$-$C_5$alkylamino-$C_1$-$C_2$alkyl, $C_2$-$C_6$dialkylamino-$C_1$-$C_2$alkyl, $C_3$-$C_7$cycloalkyl-$C_1$-$C_2$alkyl, $C_2$-$C_8$alkoxyalkyl, $C_4$-$C_8$alkenyloxyalkyl, $C_4$-$C_8$alkynyloxyalkyl, $C_2$-$C_8$alkylthioalkyl, $C_1$-$C_2$alkylsulfoxyl-$C_1$-$C_2$alkyl, $C_1$-$C_2$alkylsulfonyl-$C_1$-$C_2$alkyl, $C_2$-$C_8$alkylideneaminooxy-$C_1$-$C_2$alkyl, $C_1$-$C_5$alkylcarbonyl-$C_1$-$C_2$alkyl, $C_1$-$C_5$alkoxycarbonyl-$C_1$-$C_2$alkyl, $C_1$-$C_5$amino-carbonyl-$C_1$-$C_2$alkyl, $C_2$-$C_8$dialkylamino-carbonyl-$C_1$-$C_2$alkyl, $C_1$-$C_5$alkylcarbonylamino-$C_1$-$C_2$alkyl, $C_1$-$C_2$alkylcarbonyl-N-$C_1$-$C_3$alkyl-$C_1$-$C_2$aminoalkyl, $C_3$-$C_6$trialkylsilyl-$C_1$-$C_3$alkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_2$-$C_5$alkenyl, $C_2$-$C_5$haloalkenyl, $C_3$-$C_8$cycloalkyl, phenyl, heteroaryl, $C_1$-$C_6$alkoxy, $C_1$-$C_6$haloalkoxy, $C_1$-$C_8$alkylcarbonyl, $C_1$-$C_3$alkylamino, $C_2$-$C_6$dialkylamino, or benzyloxy or phenoxy in which the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or by nitro.

Special preference is given to compounds of formula I wherein $R_1$ and $R_3$ are each independently of the other ethyl, haloethyl, ethynyl, $C_1$-$C_2$alkoxy, $C_1$-$C_2$haloalkoxy or $C_1$-$C_2$alkylcarbonyl;

$R_4$ and $R_5$ are each independently of the other $C_1$-$C_6$alkyl, $C_1$-$C_6$haloalkyl, $C_2$-$C_6$alkoxyalkyl, $C_2$-$C_6$alkylcarbonylalkyl, $C_3$-$C_6$alkoxycarbonylalkyl, $C_1$-$C_6$aminoalkyl, $C_2$-$C_6$dialkylaminoalkyl, $C_3$-$C_6$alkylaminoalkyl, $C_1$-$C_6$cyanoalkyl, $C_3$-$C_8$cycloalkyl, aryl or heteroaryl; or $R_4$ and $R_5$, together with the atoms to which they are bonded, form a 5- to 7-membered cyclic group that may contain one or two hetero atoms selected from nitrogen, oxygen and sulfur;

$R_2$, $R_6$ and $R_{32}$ are each independently of the others $C_1$-$C_6$alkyl, $C_1$-$C_6$haloalkyl, $C_2$-$C_6$alkoxyalkyl, $C_3$-$C_8$cycloalkyl, aryl or heteroaryl;

$R_7$, $R_{31}$ and $R_{33}$ are each independently of the others hydrogen, $C_1$-$C_6$alkyl or $C_1$-$C_6$alkoxyalkyl;

$R_8$ is hydrogen, $C_1$-$C_6$alkyl, $C_1$-$C_6$haloalkyl, $C_2$-$C_6$alkoxyalkyl, $C_1$-$C_6$alkylthioalkyl, $C_3$-$C_8$cycloalkyl, aryl or heteroaryl; or $R_6$ and $R_7$ or $R_2$ and $R_{31}$ or $R_{32}$ and $R_{33}$, together with the atom to which they are bonded, form a saturated 3- to 7-membered cyclic group that may contain one or two hetero atoms selected from nitrogen, oxygen and sulfur; or $R_6$ and $R_8$, together with the atoms to which they are bonded, form a 5- to 7-membered cyclic group that may contain one or two hetero atoms selected from nitrogen, oxygen and sulfur;

$R_9$, $R_{10}$, $R_{11}$ and $R_{12}$ are each independently of the others $C_1$-$C_6$alkyl, $C_1$-$C_6$haloalkyl, $C_2$-$C_6$alkoxyalkyl, $C_3$-$C_8$cycloalkyl, aryl or heteroaryl; or $R_9$ and $R_{10}$, together with the atoms to which they are bonded, form a 5- to 7-membered cyclic group that may contain one or two hetero atoms selected from nitrogen, oxygen and sulfur; or $R_9$ and $R_{10}$, together with the atom to which they are bonded, form a saturated 3- to 7-membered cyclic group that may contain one or two hetero atoms selected from nitrogen, oxygen and sulfur;

$R_{13}$, $R_{14}$, $R_{34}$ and $R_{35}$ are each independently of the others $C_1$-$C_6$alkyl, $C_3$-$C_8$cycloalkyl, aryl or heteroaryl; or $R_{13}$ and $R_{14}$ or $R_{34}$ and $R_{35}$, together with the atoms to which they are bonded, form a 5- to 7-membered cyclic group that may contain one or two hetero atoms selected from nitrogen, oxygen and sulfur;

$R_{15}$ is $C_1$-$C_6$alkyl, $C_1$-$C_6$haloalkyl, $C_2$-$C_6$alkoxyalkyl, $C_4$-$C_6$alkenyloxyalkyl, $C_2$-$C_6$alkylthioalkyl, $C_2$-$C_6$alkylsulfoxylalkyl, $C_3$-$C_6$alkoxycarbonylalkyl, $C_3$-$C_8$cycloalkyl, aryl or heteroaryl;

$R_{16}$ is $C_1$-$C_6$alkyl, $C_1$-$C_6$haloalkyl, $C_2$-$C_6$alkoxyalkyl, $C_3$-$C_8$cycloalkyl, aryl or heteroaryl;

$R_{17}$ is $C_1$-$C_6$alkyl, $C_1$-$C_6$haloalkyl, $C_3$-$C_8$cycloalkyl, aryl or heteroaryl;

$R_{18}$ is hydrogen, $C_1$-$C_6$alkyl or $C_2$-$C_6$alkoxyalkyl; or $R_{17}$ and $R_{18}$, together with the atoms to which they are bonded, form a 3- to 7-membered cyclic group that may contain one or two hetero atoms selected from nitrogen, oxygen and sulfur;

$R_{19}$ and $R_{36}$ are each independently of the other $C_1$-$C_6$alkyl or $C_1$-$C_6$haloalkyl; or $R_{18}$ and $R_{19}$ or $R_{18}$ and $R_{36}$, together with the atom to which they are bonded, form a saturated 5- to 7-membered cyclic group that may contain one or two hetero atoms selected from nitrogen, oxygen and sulfur;

$R_{20}$, $R_{21}$, $R_{22}$ and $R_{23}$ are each independently of the others hydrogen, $C_1$-$C_8$alkyl, $C_1$-$C_8$haloalkyl, $C_3$-$C_7$cycloalkyl-$C_1$-$C_2$alkyl, $C_2$-$C_8$alkoxyalkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_2$-$C_5$alkenyl, $C_2$-$C_5$haloalkenyl, $C_3$-$C_8$cycloalkyl, phenyl or heteroaryl;

$R_{24}$, $R_{25}$ and $R_{26}$ are each independently of the others hydrogen, $C_1$-$C_8$alkyl, $C_1$-$C_8$haloalkyl, $C_3$-$C_7$cycloalkyl-$C_1$-$C_2$alkyl, $C_2$-$C_8$alkoxyalkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_2$-$C_5$alkenyl, $C_2$-$C_5$haloalkenyl, $C_3$-$C_8$cycloalkyl, phenyl, heteroaryl, $C_1$-$C_6$alkoxy, $C_1$-$C_3$alkylamino or $C_2$-$C_6$dialkylamino; and $R_{27}$ is $C_1$-$C_8$alkyl, $C_1$-$C_8$haloalkyl, $C_3$-$C_7$cycloalkyl-$C_1$-$C_2$alkyl, $C_2$-$C_8$alkoxyalkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_2$-$C_5$alkenyl, $C_2$-$C_5$haloalkenyl, $C_3$-$C_8$cycloalkyl, phenyl, heteroaryl, $C_1$-$C_6$alkoxy, $C_1$-$C_3$alkylamino, $C_2$-$C_6$dialkylamino or $C_1$-$C_8$alkylcarbonyl.

The compounds of formula I can be prepared by reacting a compound of formula XXX $$Q-H \qquad\qquad (XXX)$$

wherein Q is $Q_1$, $Q_2$, $Q_3$, $Q_4$, $Q_5$, $Q_6$, $Q_7$, $Q_8$, $Q_9$ or $Q_{10}$, the substituents of which, with the exception of $G_1$, $G_2$, $G_3$, $G_4$, $G_5$, $G_6$, $G_7$, $G_8$, $G_9$ and $G_{10}$, have the meanings given above, and $G_1$, $G_2$, $G_3$, $G_4$, $G_5$, $G_6$, $G_7$, $G_8$, $G_9$ and $G_{10}$ are hydrogen, with a compound of formula XXXI

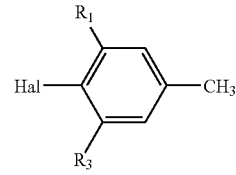

(XXXI)

wherein $R_1$ and $R_3$ are as defined for formula I and Hal is chlorine, bromine or iodine, in the presence of an inert solvent, a base and a palladium catalyst, at temperatures of from 30 to 250° C. The reaction is preferably carried out under an inert gas atmosphere.

Surprisingly, it has been shown that this process is very especially advantageous for the preparation of compounds of formula I wherein $R_1$ and $R_3$ are ethyl. The intermediates of formula XXXI wherein $R_1$ and $R_3$ are ethyl and Hal is chlorine, bromine or iodine (formula XXXIa) used for the preparation of those compounds of formula I are novel and were developed especially for that process. The present invention accordingly also relates to those intermediates.

The compounds of formula XXX are known or can be prepared according to known processes, as described, for example, in J. Chem. Soc. Perkin Trans. 1 (1987), (4), 877-884. The compounds of formula XXXI can be prepared, for example, according to known methods, via the diazonium salts, for example by Sandmeyer reaction starting from the corresponding anilines of formula XXXII

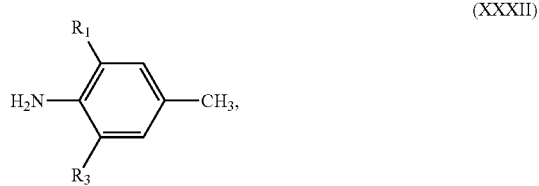

(XXXII)

wherein $R_1$ and $R_3$ are as defined for formula I. Such reactions are described, for example, in Vogel's Textbook of Practical Organic Chemistry, 5th Edition, B. S. Furniss, A. J. Hannaford, P. W. G. Smith, A. R. Tatchell; Longman Scientific & Technical 1989, page 923. The compounds of formula XXXII are known; some of them are available commercially or they can be prepared analogously to known methods.

There are suitable for the reaction bases such as trialkali metal phosphates, alkali metal and alkaline earth metal hydrides, alkali metal and alkaline earth metal amides or alkali metal alcoholates, for example tripotassium phosphate, sodium hydride, lithium diisopropylamide (LDA), sodium tert-butanolate or potassium tert-butanolate. Sodium tert-butanolate, potassium tert-butanolate and tripotassium phosphate are especially preferred.

Suitable solvents include, for example, aromatic hydrocarbons, for example xylene or toluene, ethers, such as tetrahydrofuran, dioxane or ethylene glycol dimethyl ether, dimethyl sulfoxide or tertiary amides, such as dimethylformamide, N-methylpyrrolidinone or dimethyl acetamide, and acyclic ureas, such as N,N'-dimethylpropyleneurea.

Palladium catalysts that come into consideration for the C—C coupling reaction of a compound of formula XXX with a compound of formula XXXI are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenylphosphine ($PPh_3$), tricyclopentylphosphine or tricyclohexylphosphine and the selected solvent, with a compound of formula XXXI, a compound of formula XXX and a base. Also suitable are bidendate ligands, for example 1,1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula XXXI.

The reaction temperatures are selected in accordance with the solvent used and, where applicable, in accordance with the pressure. Preferably, the reaction is carried out at atmospheric pressure.

The compounds of formula I wherein Q is $Q_1$ can be prepared analogously to the procedures described in WO 96/21652. Compounds of formula I wherein Q is $Q_2$ can be prepared, for example, in accordance with the procedures described in EP-A-0 415 185, EP-A-0 521 334, EP-A-0 355 599 and EP-A-0 442 077. Compounds of formula I wherein Q is $Q_3$, $Q_4$, $Q_6$ or $Q_7$ can be prepared, for example, in accordance with the procedures described in WO 96/35644 and WO 97/02243. Compounds of formula I wherein Q is $Q_5$ can be prepared, for example, analogously to the procedures described in WO 97/14667. Analogous procedures for the preparation of compounds of formula I wherein Q is $Q_7$ are described in WO 97/16436. Compounds of formula I in which Q is $Q_8$ can be prepared analogously to U.S. Pat. No. 5,994,274. Compounds of formula I wherein Q is $Q_9$ can be prepared analogously to JP 11152273 A (priority: 19.11.1997 JP 318614), Compounds of formula I wherein Q is $Q_{10}$ can be prepared according to J. Org. Chem. (1979), 44(26), 4906-4912 or J. Org. Chem. (1977), 42(7), 1163-1169 or in an analogous manner.

The reactions to form compounds of formula I are advantageously carried out in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, and amides, such as N,N-dimethylformamide, diethylformamide or N-methylpyrrolidinone. The reaction temperatures are preferably from −20° C. to +120° C. The reactions are generally slightly exothermic and can usually be carried out at room temperature. To shorten the reaction time or also to initiate the reaction, the temperature can, if desired, be increased to the boiling point of the reaction mixture for a brief period. The reaction times can also be shortened by the addition of a few drops of base as reaction catalyst. Suitable bases include especially tertiary amines, such as trimethylamine, triethylamine, quinuclidine, 1,4-diazabicyclo[2.2.2]octane, 1,5-diazabicyclo[4.3.0]non-5-ene and 1,5-diazabicyclo[5.4.0]undec-7-ene, but it is also possible to use inorganic bases, such as hydrides, for example sodium or calcium hydride, hydroxides, for example sodium or potassium hydroxide, carbonates, for example sodium or potassium carbonate, or hydrogen carbonates, for example potassium or sodium hydrogen carbonate.

The compounds of formula I can be isolated in customary manner by concentration and/or evaporation of the solvent and can be purified by recrystallisation or trituration of the solid residue in solvents in which they are not readily soluble, such as ethers, aromatic hydrocarbons or chlorinated hydrocarbons.

For the use in accordance with the invention of the compounds of formula I or of compositions comprising them, there are suitable any of the methods of application customary in agriculture, such as pre-emergence application, post-emergence application and seed dressing, and also various methods and techniques, for example the controlled release of active ingredient. In that method, the active ingredient is applied in solution to mineral granule carriers or polymerised granules (urea/formaldehyde) and dried. Where appropriate, it is also possible to apply a coating (coated granules) that allows the active ingredient to be released in metered amounts over a specific period.

The compounds of formula I can be used as herbicides in unmodified form, that is to say as obtained in the synthesis. Preferably, however, they are formulated in customary manner using the adjuvants customarily employed in formulation technology, for example into emulsifiable concentrates, directly sprayable or dilutable solutions, dilute emulsions, wettable powders, soluble powders, dusts, granules or microcapsules. Such formulations are described, for example, in WO 97/34485 on pages 9 to 13. As with the nature of the compositions, the methods of application, such as spraying, atomising, dusting, wetting, scattering or pouring, are chosen in accordance with the intended objectives and the prevailing circumstances.

The formulations, i.e. the compositions, preparations or mixtures comprising the active ingredient of formula I or at least one active ingredient of formula I and generally one or more solid or liquid formulation adjuvants, are prepared in known manner, e.g. by intimately mixing and/or grinding the active ingredients with the formulation adjuvants, e.g. solvents or solid carriers. In addition, it is also possible for surface-active compounds (surfactants) to be used in the preparation of the formulations. Examples of solvents and solid carriers are given, for example, in WO 97/34485 on page 6.

Depending on the nature of the active ingredient of formula I to be formulated, suitable surface-active compounds are non-ionic, cationic and/or anionic surfactants and mixtures of surfactants having good emulsifying, dispersing and wetting properties. Examples of suitable anionic, non-ionic and cationic surfactants are listed, for example, on pages 7 and 8 of WO 97/34485. Also suitable for the preparation of the herbicidal compositions according to the invention are the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I-III, Chemical Publishing Co., New York, 1980-81.

The activity of the herbicidal and plant growth-inhibiting compositions according to the invention comprising a herbicidally effective amount of compound of formula I can be increased by the addition of spray tank adjuvants.

Such adjuvants may be, for example: non-ionic surfactants, mixtures of non-ionic surfactants, mixtures of anionic surfactants with non-ionic surfactants, cationic surfactants, organosilicon surfactants, mineral oil derivatives with and without surfactants, vegetable oil derivatives with and without the addition of surfactant, alkylated derivatives of oils of vegetable or mineral origin with and without surfactants, fish oils and other animal oils of animal nature and alkyl derivatives thereof with and without surfactants, naturally occurring higher fatty acids, preferably having from 8 to 28 carbon atoms, and alkyl ester derivatives thereof, organic acids containing an aromatic ring system and one or more carboxylic acid esters, and alkyl derivatives thereof, and also suspensions of polymers of vinyl acetate or of copolymers of vinyl acetate/acrylic acid esters. Mixtures of individual adjuvants with one another and combined with organic solvents may lead to the activity being further increased.

Suitable non-ionic surfactants include, for example, polyglycol ether derivatives of aliphatic or cycloaliphatic alcohols, of saturated or unsaturated fatty acids and alkylphenols, preferably that can contain from 3 to 30 glycol ether groups and from 8 to 20 carbon atoms in the (aliphatic) hydrocarbon radical and from 6 to 18 carbon atoms in the alkyl radical of the alkylphenols.

Further suitable non-ionic surfactants are the water-soluble polyethylene oxide adducts of polypropylene glycol, ethylenediaminopolypropylene glycol and alkyl polypropylene glycol having preferably from 1 to 10 carbon atoms in the alkyl chain, which adducts contain preferably from 20 to 250 ethylene glycol ether groups and from 10 to 100 propylene glycol ether groups. The said compounds usually contain from 1 to 5 ethylene glycol units per propylene glycol unit.

There may also be mentioned, as further examples of non-ionic surfactants, nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylenesorbitan, e.g. polyoxyethylenesorbitan trioleate, are also suitable.

Preferred anionic surfactants are especially alkyl sulfates, alkyl sulfonates, alkylaryl sulfonates, alkylated phosphoric acids, and ethoxylated derivatives thereof. The alkyl radicals usually contain from 8 to 24 carbon atoms.

Preferred non-ionic surfactants are known by the following trade names:

polyoxyethylene cocoalkylamine (e.g. AMIET® 105 (Kao Co.)), polyoxyethylene oleylamine (e.g. AMIET® 415 (Kao Co.)), nonylphenol polyethoxyethanols, polyoxyethylene stearylamine (e.g. AMIET® 320 (Kao Co.)), N-polyethoxyethylamines (e.g. GENAMIN® (Hoechst AG)), N,N,N',N'-tetra(polyethoxypolypropoxyethyl)ethylenediamine (e.g. TERRONIL® and TETRONIC® (BASF Wyandotte Corp.)), BRIJ® (Atlas Chemicals), ETHYLAN® CD and ETHYLAN® D (Diamond Shamrock), GENAPOL® C, GENAPOL® O, GENAPOL® S and GENAPOL® X080 (Hoechst AG), EMULGEN® 104P, EMULGEN® 109P and EMULGEN® 408 (Kao Co.); DISTY® 125 (Geronazzo), SOPROPHOR® CY 18 (Rhone Poulenc S.A.); NONISOL® (Ciba-Geigy), MRYJ® (ICI); TWEEN® (ICI); EMULSOGEN® (Hoechst AG); AMIDOX® (Stephan Chemical Co.), ETHOMID® (Armak Co.); PLURONIC® (BASF Wyandotte Corp.), SOPROPHOR® 461 P (Rhône Poulenc S.A.), SOPROPHOR® 496/P (Rhone Poulenc S.A.), ANTAROX FM-63 (Rhone Poulenc S.A.), SLYGARD 309 (Dow Corning), SILWET 408, SILWET L-7607N (Osi-Specialities).

The cationic surfactants are especially quaternary ammonium salts that contain as N-substituent(s) at least one alkyl radical having from 8 to 22 carbon atoms and, as further substituents, optionally halogenated lower alkyl, benzyl or hydroxy-lower alkyl radicals. The salts are preferably in the form of halides, methyl sulfates or ethyl sulfates, for example stearyltrimethylammonium chloride or benzyldi(2-chloroethyl)ethylammonium bromide.

The oils used are either of mineral or natural origin. The natural oils can in addition be of animal or vegetable origin. Of the animal oils preference is given especially to derivatives of beef tallow, but fish oils (e.g. sardine oil) and derivatives thereof are also used. Vegetable oils are mostly seed oils of varied origin. Examples of vegetable oils used especially that may be mentioned include coconut oil, rapeseed oil and sunflower oil and derivatives thereof.

In the composition according to the invention, the concentrations of oil additive are generally from 0.01 to 2%, based on the spray mixture. The oil additive can, for example, be added to the spray tank in the desired concentration after the spray mixture has been prepared.

Preferred oil additives in the composition according to the invention comprise an oil of vegetable origin, for example rapeseed oil or sunflower oil, alkyl esters of oils of vegetable origin, for example methyl derivatives, or mineral oils.

Especially preferred oil additives comprise alkyl esters of higher fatty acids ($C_8$-$C_{22}$), especially the methyl derivatives of $C_{12}$-$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9).

The application and action of the oil additives can be improved by combining them with surface-active substances, such as non-ionic, anionic or cationic surfactants. Examples of suitable anionic, non-ionic and cationic surfactants are listed in WO 97/34485 on pages 7 and 8.

Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available preferred surfactants are the Genapol types (Clariant AG, Muttenz, Switzerland). The concentration of the surface-active substances in relation to the total additive is generally from 1 to 30% by weight.

Examples of oil additives consisting of mixtures of oils or mineral oils or derivatives thereof with surfactants include Edenor ME SU®, Emery 2231® (Henkel subsidiary Cognis GMBH, DE), Turbocharge® (Zeneca Agro, Stoney Creek, Ontario, Calif.) or, more especially, Actipron® (BP Oil UK Limited, GB).

The addition of an organic solvent to the oil additive/surfactant mixture can, furthermore, bring about a further increase in activity. Suitable solvents include, for example, Solvesso® (ESSO) and Aromatic Solvent® (Exxon Corporation) types.

The concentration of such solvents can be from 10 to 80%, by weight, of the total weight.

Such oil additives, which, for example, are also described in U.S. Pat. No. 4,834,908, are especially preferred for the composition according to the invention. A more especially preferred oil additive is known by the name MERGE®, can be obtained from BASF Corporation and is basically described, for example, in U.S. Pat. No. 4,834,908, col. 5, as Example COC-1. A further oil additive that is preferred in accordance with the invention is SCORE® (Novartis Crop Protection Canada).

Surfactants, oils, especially vegetable oils, derivatives thereof, such as alkylated fatty acids and mixtures thereof, for example with preferably anionic surfactants, such as alkylated phosphoric acids, alkyl sulfates and alkylaryl sulfonates and also higher fatty acids, that are customary in formulation and adjuvant technology and that can also be used in the compositions according to the invention and in spray tank solutions thereof, are described, inter alia, in "Mc Cutcheon's Detergents and Emulsifiers Annual" MC Publishing Corp., Ridgewood N.J., 1998, Stache, H., "Tensid-Taschenbuch", Carl Hanser Verlag, Munich/Vienna, 1990, M. and J. Ash, "Encyclopedia of Surfactants", Vol I-IV, Chemical Publishing Co., New York, 1981-89, G. Kapusta, "A Compendium of Herbicide Adjuvants", Southern Illinois Univ., 1998, L. Thomson Harvey, "A Guide to Agricultural Spray Adjuvants Used in the United States", Thomson Pubns., 1992.

The herbicidal formulations generally contain from 0.1 to 99% by weight, especially from 0.1 to 95% by weight, of herbicide, from 1 to 99.9% by weight, especially from 5 to 99.8% by weight, of a solid or liquid formulation adjuvant, and from 0 to 25% by weight, especially from 0.1 to 25% by weight, of a surfactant. Whereas commercial products will preferably be formulated as concentrates, the end user will normally employ dilute formulations. The compositions may also comprise further ingredients, such as stabilisers, for example vegetable oils or epoxidised vegetable oils (epoxidised coconut oil, rapeseed oil or soybean oil), anti-foams, for example silicone oil, preservatives, viscosity regulators, binders, tackifiers and also fertilisers or other active ingredients.

The active ingredients of formula I are generally used on the plants or the locus thereof at rates of application of from 0.001 to 4 kg/ha, especially from 0.005 to 2 kg/ha. The concentration required to achieve the desired effect can be determined by experiment. It is dependent on the type of action, the development stage of the crop plant and of the weed and on the application (place, time, method) and, in dependence on those parameters, can vary within wide ranges.

The compounds of formula I are distinguished by herbicidal and growth-inhibiting properties that make them suitable for use in crops of useful plants, especially in cereals, cotton, soybeans, sugar beet, sugar cane, plantation crops, rape, maize and rice, and for non-selective weed control. Crops are also to be understood as including those that have been rendered tolerant to herbicides or classes of herbicides by conventional breeding or genetic engineering methods. Those include, for example, IMI Maize, Poast Protected Maize (sethoxydim tolerance), Liberty Link Maize, B.t./Liberty Link Maize, IMI/Liberty Link Maize, IMI/Liberty Link/B.t. Maize, Roundup Ready Maize and Roundup Ready/B.t. Maize.

The weeds to be controlled may be either monocotyledonous or dicotyledonous weeds, for example *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica*.

Surprisingly, it has been shown that special safeners, known from U.S. Pat. No. 5,041,157, U.S. Pat. No. 5,541,148, U.S. Pat. No. 5,006,656, EP-A-0 094 349, EP-A-0 551 650, EP-A-0 268 554, EP-A-0 375 061, EP-A-0 174 562, EP-A-492 366, WO 91/7874, WO 94/987, DE-A-19612943, WO 96/29870, WO 98/13361, WO 98/39297, WO 98/27049, EP-A-0 716 073, EP-A-0 613 618, U.S. Pat. No. 5,597,776, EP-A-0 430 004, DE-A-4 331 448, WO 99/16744, WO 00/30447 and WO 00/00020, are suitable for mixing with the herbicidal compositions according to the invention. The present invention accordingly relates also to a selective-herbicidal composition for controlling grasses and weeds in crops of useful plants, especially in crops of maize and cereals, which composition comprises a herbicide of formula I and a safener (antidote) and protects the useful plants, but not the weeds, against the phytotoxic action of the herbicide, and to the use of such a composition in the control of weeds in crops of useful plants.

There is thus proposed, in accordance with the invention, a selective-herbicidal composition that comprises as active ingredient, in addition to customary inert formulation adjuvants, such as carriers, solvents and welting agents, a mixture of a) a herbicidally effective amount of a compound of formula I

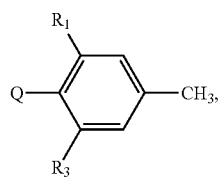
(I)

wherein $R_1$, $R_3$ and Q are as defined hereinabove, with the proviso that Q is other than $Q_1$; and b) a herbicide-antagonistically effective amount either of a compound of formula X

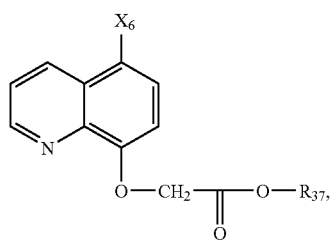
(X)

wherein $R_{37}$ is hydrogen, $C_1$-$C_8$alkyl, or $C_1$-$C_8$alkyl substituted by $C_1$-$C_6$alkoxy or by $C_3$-$C_6$alkenyloxy; and $X_7$ is hydrogen or chlorine; or of a compound of formula XI

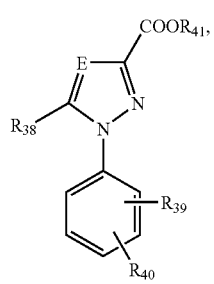
(XI)

wherein E is nitrogen or methine;
$R_{38}$ is —$CCl_3$, phenyl or phenyl substituted by halogen;
$R_{39}$ and $R_{40}$ are each independently of the other hydrogen or halogen; and $R_{41}$ is $C_1$-$C_4$alkyl; or of a compound of formula XII

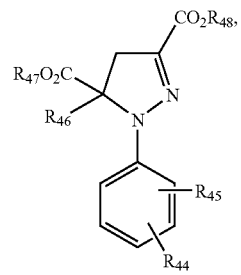
(XII)

wherein $R_{44}$ and $R_{45}$ are each independently of the other hydrogen or halogen, and
$R_{46}$, $R_{47}$ and $R_{48}$ are each independently of the others $C_1$-$C_4$alkyl, or of a compound of formula XIII

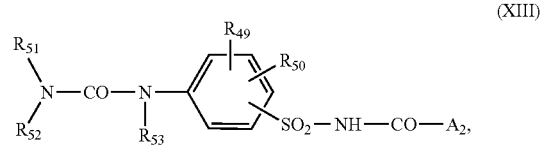
(XIII)

wherein $A_2$ is a group

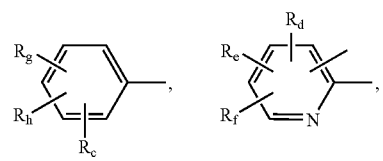

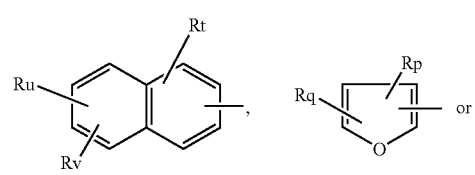

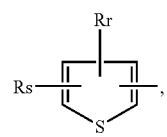

$R_{51}$ and $R_{52}$ are each independently of the other hydrogen, $C_1$-$C_8$alkyl, $C_3$-$C_8$cycloalkyl, $C_3$-$C_6$alkenyl, $C_3$-$C_6$alkynyl,

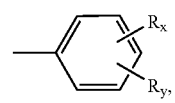

or C$_1$-C$_4$alkyl substituted by C$_1$-C$_4$alkoxy or by

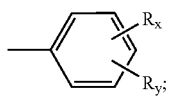

or R$_{51}$, and R$_{52}$ together form a C$_4$-C$_6$alkylene bridge that may be interrupted by oxygen, sulfur, SO, SO$_2$, NH or by —N(C$_1$-C$_4$alkyl)-;

R$_{53}$ is hydrogen or C$_1$-C$_4$alkyl;

R$_{49}$ is hydrogen, halogen, cyano, trifluoromethyl, nitro, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, —COOR$_j$, —CONR$_k$R$_m$, —COR$_n$, —SO$_2$NR$_k$R$_m$ or —OSO$_2$-C$_1$-C$_4$alkyl;

R$_g$ is hydrogen, halogen, cyano, nitro, C$_1$-C$_4$alkyl, C$_1$-C$_4$haloalkyl, C$_1$-C$_4$alkylthio, C$_1$-C$_4$alkylsulfinyl, C$_1$-C$_4$alkylsulfonyl, —COOR$_j$, —CONR$_k$R$_m$, —COR$_n$, —SO$_2$NR$_k$R$_m$, —OSO$_2$-C$_1$-C$_4$alkyl, C$_1$-C$_6$alkoxy, or C$_1$-C$_6$alkoxy substituted by C$_1$-C$_4$alkoxy or by halogen, C$_3$-C$_6$alkenyloxy, or C$_3$-C$_6$alkenyloxy substituted by halogen, or C$_3$-C$_6$alkynyloxy, or R$_{49}$ and R$_{50}$ together form a C$_3$-C$_4$alkylene bridge that may be substituted by halogen or by C$_1$-C$_4$alkyl, or together form a C$_3$-C$_4$alkenylene bridge that may be substituted by halogen or by C$_1$-C$_4$alkyl, or together form a C$_4$alkadienylene bridge that may be substituted by halogen or by C$_1$-C$_4$alkyl;

R$_{50}$ and R$_h$ are each independently of the other hydrogen, halogen, C$_1$-C$_4$alkyl, trifluoromethyl, C$_1$-C$_6$alkoxy, C$_1$-C$_6$alkylthio or —COOR$_j$;

R$_c$ is hydrogen, halogen, nitro, C$_1$-C$_4$alkyl or methoxy; R$_d$ is hydrogen, halogen, nitro, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, —COOR$_j$ or CONR$_k$R$_m$;

R$_e$ is hydrogen, halogen, C$_1$-C$_4$alkyl, —COOR$_j$, trifluoromethyl or methoxy, or R$_d$ and R$_e$ together form a C$_3$-C$_4$alkylene bridge;

Rp is hydrogen, halogen, C$_1$-C$_4$alkyl, —COOR$_j$, trifluoromethyl or methoxy; Rq is hydrogen, halogen, nitro, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, —COOR$_j$ or CONR$_k$R$_m$; or Rp and Rq together form a C$_3$-C$_4$alkylene bridge;

Rr is hydrogen, halogen, C$_1$-C$_4$alkyl, —COOR$_j$, trifluoromethyl or methoxy; Rs is hydrogen, halogen, nitro, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, —COOR$_j$ or CONR$_k$R$_m$; or Rr and Rs together form a C$_3$-C$_4$alkylene bridge;

Rt is hydrogen, halogen, C$_1$-C$_4$alkyl, —COOR$_j$, trifluoromethyl or methoxy; Ru is hydrogen, halogen, nitro, C$_1$-C$_4$alkyl, C$_1$-C$_4$alkoxy, C$_1$-C$_4$alkylthio, C$_1$-C$_4$alkylsulfinyl, C$_1$-C$_4$alkylsulfonyl, —COOR$_j$ or CONR$_k$R$_m$; or Rv and Ru together form a C$_3$-C$_4$alkylene bridge;

R$_f$ and Rv are hydrogen, halogen or C$_1$-C$_4$alkyl;

R$_x$ and R$_y$ are each independently of the other hydrogen, halogen, C$_1$-C$_4$alkyl, C$_1$-C$_4$alkoxy, C$_1$-C$_4$alkylthio, —COOR$_{54}$, trifluoromethyl, nitro or cyano;

R$_j$, R$_k$ and R$_m$ are each independently of the others hydrogen or C$_1$-C$_4$alkyl; or R$_k$ and R$_m$ together form a C$_4$-C$_6$alkylene bridge that may be interrupted by oxygen, NH or by —N(C$_1$-C$_4$alkyl)-;

R$_n$ is C$_1$-C$_4$alkyl, phenyl, or phenyl substituted by halogen, C$_1$-C$_4$alkyl, methoxy, nitro or by trifluoromethyl;

R$_{54}$ is hydrogen, C$_1$-C$_{10}$alkyl, C$_1$-C$_4$alkoxy-C$_1$-C$_4$alkyl, C$_1$-C$_4$alkylthio-C$_1$-C$_4$alkyl, di-C$_1$-C$_4$alkylamino-C$_1$-C$_4$alkyl, halo-C$_1$-C$_8$alkyl, C$_2$-C$_8$alkenyl, halo-C$_2$-C$_8$alkenyl, C$_3$-C$_8$alkynyl, C$_3$-C$_7$cycloalkyl, halo-C$_3$-C$_7$cycloalkyl, C$_1$-C$_8$alkylcarbonyl, allylcarbonyl, C$_3$-C$_7$cycloalkylcarbonyl, benzoyl, which is unsubstituted or substituted on the phenyl ring identically or differently up to three times by halogen, C$_1$-C$_4$alkyl, halo-C$_1$-C$_4$alkyl, halo-C$_1$-C$_4$alkoxy or C$_1$-C$_4$alkoxy; or furoyl, thienyl; or C$_1$-C$_4$alkyl substituted by phenyl, halophenyl, C$_1$-C$_4$alkylphenyl, C$_1$-C$_4$alkoxyphenyl, halo-C$_1$-C$_4$alkylphenyl, halo-C$_1$-C$_4$alkoxyphenyl, C$_1$-C$_6$alkoxycarbonyl, C$_1$-C$_4$alkoxy-C$_1$-C$_8$alkoxycarbonyl, C$_3$-C$_8$alkenyloxycarbonyl, C$_3$-C$_8$alkynyloxycarbonyl, C$_1$-C$_8$alkylthiocarbonyl, C$_3$-C$_8$alkenylthiocarbonyl, C$_3$-C$_8$alkynylthiocarbonyl, carbamoyl, mono-C$_1$-C$_4$alkylaminocarbonyl, di-C$_1$-C$_4$alkylaminocarbonyl; or phenylaminocarbonyl, which is unsubstituted or substituted on the phenyl identically or differently up to three times by halogen, C$_1$-C$_4$alkyl, halo-C$_1$-C$_4$alkyl, halo-C$_1$-C$_4$alkoxy or C$_1$-C$_4$alkoxy or once by cyano or nitro; or dioxolan-2-yl, which is unsubstituted or substituted by one or two C$_1$-C$_4$alkyl radicals, or dioxan-2-yl, which is unsubstituted or substituted by one or two C$_1$-C$_4$alkyl radicals, or C$_1$-C$_4$alkyl substituted by cyano, nitro, carboxyl or by C$_1$-C$_8$alkylthio-C$_1$-C$_8$alkoxycarbonyl;

or of a compound of formula XIV

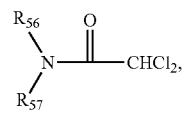

(XIV)

wherein R$_{56}$ and R$_{57}$ are each independently of the other C$_1$-C$_6$alkyl or C$_2$-C$_6$alkenyl; or R$_{56}$ and R$_{57}$ together are

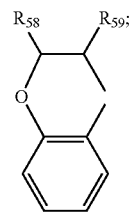

R$_{58}$ and R$_{59}$ are each independently of the other hydrogen or C$_1$-C$_6$alkyl; or R$_{56}$ and R$_{57}$ together are

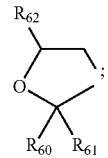

R$_{60}$ and R$_{61}$ are each independently of the other C$_1$-C$_4$alkyl, or R$_{60}$ and R$_{61}$ together are —(CH$_2$)$_5$—;

R$_{62}$ is hydrogen, C$_1$-C$_4$alkyl or

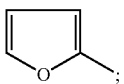

or $R_{56}$ and $R_{57}$ together are

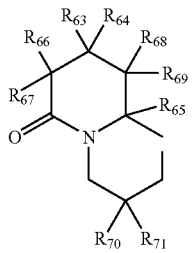 or 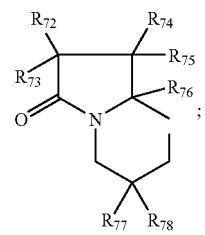 ;

$R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$ and $R_{78}$ are each independently of the others hydrogen or $C_1$-$C_4$alkyl;

or of a compound of formula XV

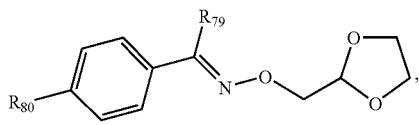

(XV)

wherein $R_{80}$ is hydrogen or chlorine and $R_{79}$ is cyano or trifluoromethyl;

or of a compound of formula XVI

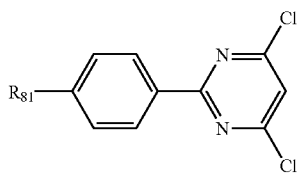

(XVI)

wherein $R_{81}$ is hydrogen or methyl;

or of a compound of formula XVII

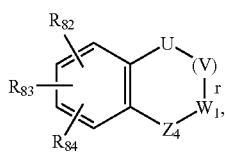

(XVII)

wherein
$R_{82}$ is hydrogen, $C_1$-$C_4$alkyl, or $C_1$-$C_4$alkyl substituted by $C_1$-$C_4$alkyl-$X_2$- or by $C_1$-$C_4$haloalkyl-$X_2$-, or is $C_1$-$C_4$haloalkyl, nitro, cyano, —COO$R_{85}$, —N$R_{86}R_{87}$, —SO$_2$N$R_{88}R_{89}$ or —CON$R_{90}R_{91}$;

$R_{83}$ is hydrogen, halogen, $C_1$-$C_4$alkyl, trifluoromethyl, $C_1$-$C_4$alkoxy or $C_1$-$C_4$haloalkoxy;

$R_{84}$ is hydrogen, halogen or $C_1$-$C_4$alkyl;

U, V, $W_1$ and $Z_4$ are each independently of the others oxygen, sulfur, $C(R_{92})R_{93}$, carbonyl, $NR_{94}$, or a group

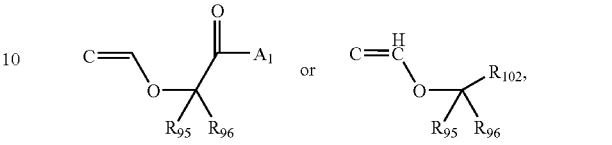

wherein $R_{102}$ is $C_2$-$C_4$alkenyl or $C_2$-$C_4$alkynyl; with the provisos that a) at least one of the ring members U, V, W. or $Z_4$ is carbonyl, and a ring member adjacent to that ring member or to those ring members is the group

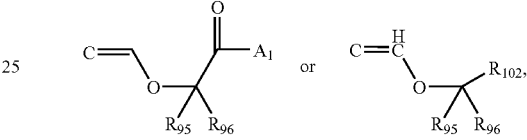

that group occurring only once; and b) two adjacent ring members U and V, V and $W_1$ and $W_1$ and $Z_4$ cannot simultaneously be oxygen;

$R_{95}$ and $R_{96}$ are each independently of the other hydrogen or $C_1$-$C_8$alkyl; or $R_{95}$ and $R_{96}$ together form a $C_2$-$C_6$alkylene group;

$A_1$ is $R_{99}$—$Y_1$— or —$NR_{97}R_{98}$;

$X_2$ is oxygen or —S(O)$_s$;

$Y_1$ is oxygen or sulfur;

$R_{99}$ is hydrogen, $C_1$-$C_8$alkyl, $C_1$-$C_8$haloalkyl, $C_1$-$C_4$alkoxy-$C_1$-$C_8$alkyl, $C_3$-$C_6$alkenyloxy-$C_1$-$C_8$alkyl, or phenyl-$C_1$-$C_8$alkyl in which the phenyl ring may be substituted by halogen, $C_1$-$C_4$alkyl, trifluoromethyl, methoxy or by methyl—S(O)$_s$—, or is $C_3$-$C_6$alkenyl, $C_3$-$C_6$haloalkenyl, phenyl-$C_3$-$C_6$alkenyl, $C_3$-$C_6$alkynyl, phenyl-$C_3$-$C_6$alkynyl, oxetanyl, furyl or tetrahydrofuryl;

$R_{85}$ is hydrogen or $C_1$-$C_4$alkyl;

$R_{86}$ is hydrogen, $C_1$-$C_4$alkyl or $C_1$-$C_4$alkylcarbonyl;

$R_{87}$ is hydrogen or $C_1$-$C_4$alkyl; or $R_{86}$ and $R_{87}$ together form a $C_4$- or $C_5$-alkylene group;

$R_{88}$, $R_{89}$, $R_{90}$ and $R_{91}$ are each independently of the others hydrogen or $C_1$-$C_4$alkyl; or $R_{88}$ together with $R_{89}$, or $R_{90}$ together with $R_{91}$, are each independently of the other $C_4$- or $C_5$-alkylene in which one carbon atom may have been replaced by oxygen or by sulfur, or one or two carbon atoms may have been replaced by —$NR_{100}$—;

$R_{92}$, $R_{100}$ and $R_{93}$ are each independently of the others hydrogen or $C_1$-$C_8$alkyl; or $R_{92}$ and $R_{93}$ together are $C_2$-$C_6$alkylene;

$R_{94}$ is hydrogen or $C_1$-$C_8$alkyl;

$R_{97}$ is hydrogen, $C_1$-$C_8$alkyl, phenyl or phenyl-$C_1$-$C_8$alkyl, wherein the phenyl rings may be substituted by fluorine, chlorine, bromine, nitro, cyano, —OCH$_3$, $C_1$-$C_4$alkyl or by CH$_3$SO$_2$—, or is $C_1$-$C_4$alkoxy-$C_1$-$C_8$alkyl, $C_3$-$C_6$alkenyl or $C_3$-$C_6$alkynyl;

$R_{98}$ is hydrogen, $C_1$-$C_8$alkyl, $C_3$-$C_6$alkenyl or $C_3$-$C_6$alkynyl; or $R_{97}$ and $R_{98}$ together are $C_4$- or $C_5$-alkylene in which one carbon atom may have been replaced by oxygen or by sulfur, or one or two carbon atoms may have been replaced by —$NR_{101}$—;

$R_{101}$ is hydrogen or $C_1$-$C_4$alkyl;

r is 0 or 1; and s is 0, 1 or 2, or of a compound of formula XVIII

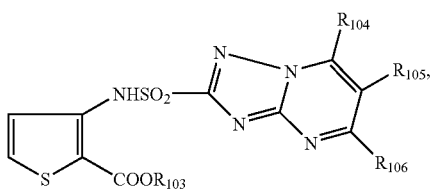

(XVIII)

wherein $R_{103}$ is hydrogen, $C_1$-$C_6$alkyl, $C_3$-$C_6$cycloalkyl, $C_3$-$C_6$alkenyl or $C_3$-$C_6$alkynyl; and $R_{104}$, $R_{105}$ and $R_{106}$ are each independently of the others hydrogen, $C_1$-$C_6$alkyl, $C_3$-$C_6$cycloalkyl or $C_1$-$C_6$alkoxy, with the proviso that one of the substituents $R_{104}$, $R_{105}$ and $R_{106}$ is other than hydrogen;

or of a compound of formula XIX

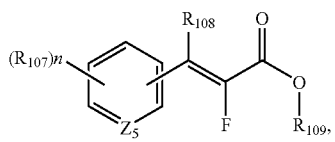

(XIX)

wherein $Z_5$ is N or CH, n is 0, 1, 2 or 3 when $Z_5$ is N, and n is 0, 1, 2, 3 or 4 when $Z_5$ is CH, $R_{107}$ is halogen, $C_1$-$C_4$alkyl, $C_1$-$C_4$haloalkyl, $C_1$-$C_4$alkoxy, $C_1$-$C_4$haloalkoxy, nitro, $C_1$-$C_4$alkylthio, $C_1$-$C_4$alkylsulfonyl, $C_1$-$C_4$alkoxycarbonyl, phenyl or phenoxy, or phenyl or phenoxy substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{108}$ is hydrogen or $C_1$-$C_4$alkyl, $R_{109}$ is hydrogen, $C_1$-$C_4$alkyl, $C_3$-$C_6$cycloalkyl, $C_2$-$C_6$alkenyl, $C_2$-$C_6$alkynyl, $C_1$-$C_4$haloalkyl, $C_2$-$C_6$haloalkenyl, $C_2$-$C_6$haloalkynyl, $C_1$-$C_4$alkylthio-$C_1$-$C_4$alkyl, $C_1$-$C_4$alkylsulfonyl-$C_1$-$C_4$alkyl, $C_1$-$C_4$alkoxy-$C_1$-$C_4$alkyl, $C_1$-$C_4$alkenyloxy-$C_1$-$C_4$alkyl or $C_1$-$C_4$alkynyloxy-$C_1$-$C_4$alkyl;

or of a compound of formula XX

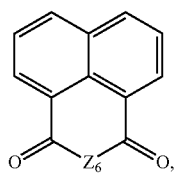

(XX)

wherein $Z_6$ is oxygen or N—$R_{110}$ and $R_{110}$ is a group of formula

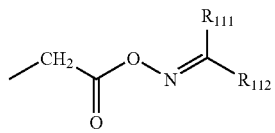

wherein $R_{111}$ and $R_{112}$ are each independently of the other cyano, hydrogen, $C_1$-$C_4$alkyl, $C_3$-$C_6$cycloalkyl, $C_2$-$C_6$alkenyl, aryl, phenyl or heteroaryl, or phenyl, aryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

or of a compound of formula XXI

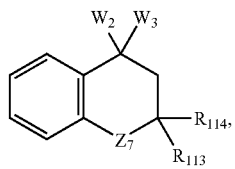

(XXI)

wherein $Z_7$ is oxygen, sulfur, S=O, $SO_2$ or $CH_2$, $R_{113}$ and $R_{114}$ are each independently of the other hydrogen, halogen or $C_1$-$C_4$alkyl, $W_2$ and $W_3$ are each independently of the other $CH_2COOR_{115}$ or $COOR_{0115}$ or together are a group of formula —($CH_2$)C(O)—O—C(O)—($CH_2$)—, and $R_{115}$ and $R_{0115}$ are each independently of the other hydrogen, $C_1$-$C_4$alkyl, $C_2$-$C_4$alkenyl, $C_2$-$C_6$alkynyl, $C_3$-$C_6$cycloalkyl, $C_1$-$C_4$haloalkyl, or a metal cation or an ammonium cation;

or of a compound of formula XXII

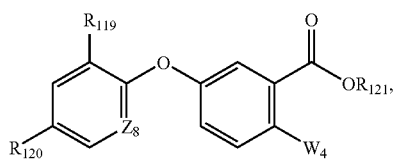

(XXII)

wherein $R_{119}$ and $R_{120}$ are each independently of the other hydrogen, halogen or $C_1$-$C_4$haloalkyl, $R_{121}$ is hydrogen, $C_1$-$C_4$alkyl, $C_3$-$C_4$alkenyl, $C_3$-$C_4$alkynyl, $C_1$-$C_4$haloalkyl, $C_3$-$C_6$cycloalkyl, a metal cation or an ammonium cation, $Z_8$ is N, CH, C—F or C—Cl and $W_4$ is a group of formula

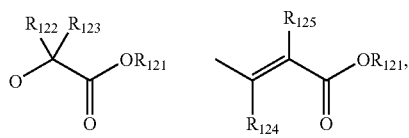

wherein $R_{122}$ and $R_{123}$ are each independently of the other hydrogen or $C_1$-$C_4$alkyl and $R_{124}$ and $R_{125}$ are each independently of the other hydrogen or $C_1$-$C_4$alkyl;

or of a compound of formula XXIII

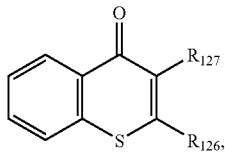

(XXIII)

wherein $R_{126}$ is hydrogen, cyano, halogen, $C_1$-$C_4$alkyl, $C_3$-$C_6$cycloalkyl, $C_1$-$C_4$alkoxy, $C_1$-$C_4$alkoxycarbonyl, $C_1$-$C_4$alkylthiocarbonyl, —NH—$R_{128}$, —C(O)NH—$R_{0128}$, aryl or heteroaryl, or aryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{127}$ is hydrogen, cyano, nitro, halogen, $C_1$-$C_4$alkyl, $C_1$-$C_4$haloalkyl, $C_1$-$C_4$alkoxy or $C_1$-$C_4$thioalkyl; and $R_{128}$ and $R_{0128}$ are each independently of the other $C_1$-$C_4$alkyl, $C_1$-$C_4$haloalkyl, $C_3$-$C_4$alkenyl, $C_3$-$C_4$alkynyl, $C_3$-$C_4$cycloalkyl, aryl or heteroaryl, or aryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, formyl, $C_1$-$C_4$alkylcarbonyl or $C_1$-$C_4$alkylsufonyl;

or of a compound of formula XXIV

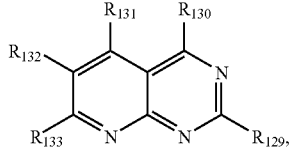

(XXIV)

wherein $R_{129}$ and $R_{130}$ are each independently of the other hydrogen, $C_1$-$C_4$alkyl, $C_1$-$C_4$haloalkyl, $C_1$-$C_4$alkoxy, mono-$C_1$-$C_8$- or di-$C_1$-$C_8$-alkylamino, $C_3$-$C_6$cycloalkyl, $C_1$-$C_4$thioalkyl, phenyl or heteroaryl, $R_{131}$ has the meanings of $R_{129}$ and in addition is OH, $NH_2$, halogen, di-$C_1$-$C_4$aminoalkyl, $C_1$-$C_4$alkylthio, $C_1$-$C_4$alkylsulfonyl or $C_1$-$C_4$alkoxycarbonyl, $R_{132}$ has the meanings of $R_{129}$ and in addition is cyano, nitro, carboxyl, $C_1$-$C_4$alkoxycarbonyl, di-$C_1$-$C_4$aminoalkyl, $C_1$-$C_4$alkylthio, $C_1$-$C_4$alkylsulfonyl, $SO_2$—OH, i-$C_1$-$C_4$aminoalkylsulfonyl or $C_1$-$C_4$alkoxysulfonyl, $R_{133}$ has the meanings of $R_{129}$ and in addition is OH, $NH_2$, halogen, di-$C_1$-$C_4$aminoalkyl, pyrrolidin-1-yl, piperidin-1-yl, morpholin-1-yl, $C_1$-$C_4$alkylthio, $C_1$-$C_4$alkylsulfonyl, $C_1$-$C_4$alkoxycarbonyl, phenoxy, naphthoxy, phenylamino, benzoyloxy or phenylsulfonyloxy;

or of a compound of formula XXV

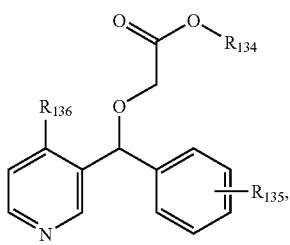

(XXV)

wherein $R_{134}$ is hydrogen, $C_4$alkyl, $C_1$-$C_4$haloalkyl, $C_2$-$C_4$alkenyl, $C_2$-$C_4$alkynyl or $C_1$-$C_4$alkoxy-$C_1$-$C_4$alkyl, $R_{135}$ is hydrogen, halogen, $C_1$-$C_4$alkyl, $C_1$-$C_4$haloalkyl or $C_1$-$C_4$alkoxy and $R_{136}$ is hydrogen, halogen, $C_1$-$C_4$alkyl, $C_1$-$C_4$haloalkyl or $C_1$-$C_4$alkoxy, with the proviso that $R_{135}$ and $R_{136}$ are not simultaneously hydrogen, or of formula XXVI

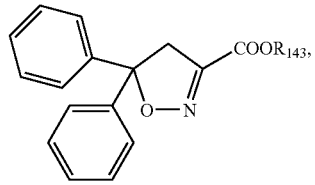

(XXVI)

wherein $R_{143}$ is hydrogen, an alkali metal cation, alkaline earth metal cation, sulfonium cation or ammonium cation or ethyl;

or of formula XXVII

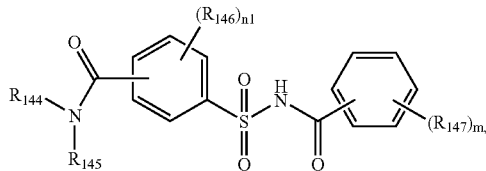

(XXVII)

wherein $R_{144}$ and $R_{145}$ are each independently of the other hydrogen, $C_1$-$C_6$alkyl, $C_2$-$C_6$alkenyl, $C_2$-$C_6$alkynyl or $C_3$-$C_6$cycloalkyl;

$R_{146}$ is hydrogen, halogen, $C_1$-$C_4$alkyl, $C_1$-$C_6$haloalkyl or $C_1$-$C_6$haloalkoxy;

$R_{147}$ is hydrogen, halogen, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$alkoxycarbonyl or nitro;

$n$, is 0, 1, 2 or 3; and $m$ is 1 or 2;

or of formula XXVIII

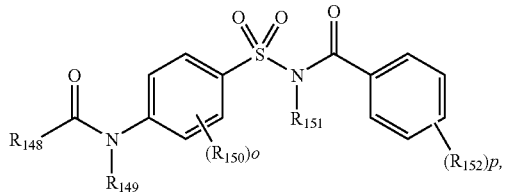

(XXVIII)

wherein $R_{148}$ is hydrogen, $C_1$-$C_6$alkyl, $C_1$-$C_6$alkoxy, $C_1$-$C_6$alkylthio, $C_3$-$C_8$cycloalkyl, phenyl, phenyl-$C_1$-$C_6$alkyl or heteroaryl; wherein the said groups may be substituted by halogen, cyano, nitro, amino, hydroxy, carbonyl, carboxyl, formyl, carbonamide or by sulfonamide;

$R_{149}$ is hydrogen, $C_1$-$C_6$alkyl or $C_1$-$C_4$haloalkyl;

each $R_{150}$ is independently of any other(s) hydrogen, halogen, $C_1$-$C_4$alkyl, $C_1$-$C_4$haloalkyl, $C_1$-$C_4$alkoxy, $C_1$-$C_4$alkylthio, $C_1$-$C_4$alkylsulfonyl, cyano, nitro, formyl or carboxyl;

$R_{151}$ is hydrogen, $C_1$-$C_6$alkyl or $C_1$-$C_4$haloalkyl;

each $R_{152}$ is independently of any other(s) hydrogen, halogen, $C_1$-$C_4$alkyl, $C_1$-$C_4$haloalkyl, $C_1$-$C_4$alkoxy, $C_1$-$C_4$alkylthio, $C_1$-$C_4$alkylsulfonyl, cyano, nitro, formyl or carboxyl;

o is 0, 1, or 2, and p is 0, 1 or 2;

or of formula XXIX

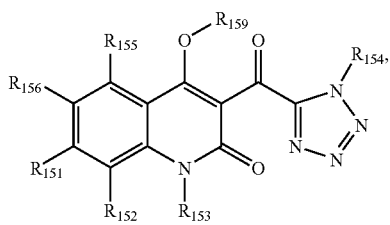

(XXIX)

wherein $R_{159}$ is hydrogen, formyl, $C_{1-6}$alkylcarbonyl, $C_{1-6}$alkenylcarbonyl, $C_{1-6}$alkynylcarbonyl, $C_{1-6}$alkoxycarbonyl, $C_{1-6}$alkylthiocarbonyl, $C_{3-8}$cycloalkylcarbonyl, phenyl-$C_{1-6}$alkylcarbonyl, phenylcarbonyl, $C_{1-6}$alkylsulfonyl, $C_{1-6}$alkenylsulfonyl or phenylsulfonyl, wherein the aforementioned hydrocarbon groups may be substituted by one or more halogen atoms, cyano, nitro, amino, methoxy, ethoxy or phenyl;

$R_{153}$ is hydrogen, $C_{1-6}$alkyl, $C_{1-6}$alkenyl, $C_{1-6}$alkynyl, $C_{3-8}$cycloalkyl, formyl, $C_{1-6}$alkylcarbonyl, $C_{1-6}$alkenylcarbonyl, $C_{1-6}$alkynylcarbonyl, $C_{1-6}$alkoxycarbonyl, $C_{1-6}$alkylthiocarbonyl, $C_{3-8}$cycloalkylcarbonyl, $C_{1-6}$alkylsulfonyl, $C_{1-6}$alkenylsulfonyl or phenylsulfonyl, wherein the afore-mentioned hydrocarbon groups may be substituted by one or more halogen atoms, cyano, nitro, amino, methoxy, ethoxy or phenyl;

$R_{154}$ is hydrogen, $C_{1-6}$alkyl, $C_{1-6}$alkenyl, $C_{1-6}$alkynyl, $C_{3-8}$cycloalkyl, formyl, $C_{1-6}$alkylcarbonyl, $C_{1-6}$alkenylcarbonyl, $C_{1-6}$alkynylcarbonyl, $C_{1-6}$alkoxycarbonyl, $C_{1-6}$alkylthiocarbonyl, $C_{3-8}$cycloalkylcarbonyl, $C_{1-6}$alkylsulfonyl, $C_{1-6}$alkenylsulfonyl or phenylsulfonyl, wherein the afore-mentioned hydrocarbon groups may be substituted by one or more halogen atoms, cyano, nitro, amino, methoxy, ethoxy or phenyl;

$R_{155}$, $R_{156}$, $R_{157}$, and $R_{158}$ are each independently of the others hydrogen, halogen, amino, $C_{1-3}$alkylamino, $C_{1-6}$dialkylamino, hydroxy, cyano, nitro, formyl, carboxyl, $C_{1-6}$alkoxy, $C_{1-6}$haloalkoxy, $C_{1-6}$alkylcarbonyl, $C_{1-6}$alkoxycarboxyl, $C_{1-6}$alkyl, $C_{1-6}$haloalkyl, $C_{1-6}$alkenyl or $C_{1-6}$alkynyl;

or $R_{153}$ and $R_{158}$, together with the ring atoms to which they are bonded, form a five- or six-membered, partially saturated or unsaturated ring that may contain up to 2 identical or different hetero atoms from the group oxygen, sulfur and nitrogen, it being possible for that ring to be substituted by an oxo radical.

Preferably, the compositions according to the invention comprise a herbicide-antagonistically effective amount of a safener of formula X, XI, XII, XIII, XIV, XV, XVI, XVII, XVIII, XIX, XX, XXI, XXII, XXIII, XXIV or XXV.

Preferably, the selective-herbicidal composition according to the invention comprises, in herbicide-antagonistically effective amount, either a compound of formula X

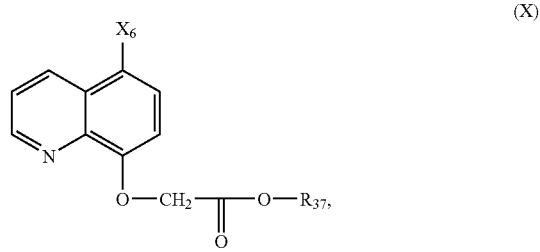

(X)

wherein $R_{37}$ is hydrogen, $C_1$-$C_8$alkyl, or $C_1$-$C_8$alkyl substituted by $C_1$-$C_6$alkoxy or by $C_3$-$C_6$alkenyloxy; and $X_6$ is hydrogen or chlorine; or a compound of formula XI

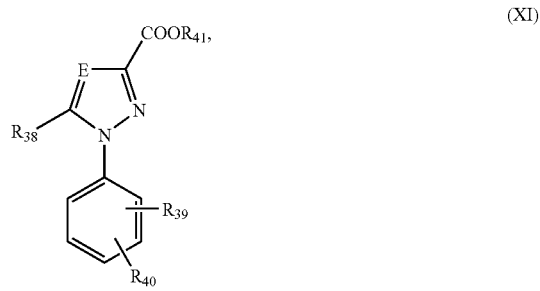

(XI)

wherein

E is nitrogen or methine; $R_{38}$ is —$CCl_3$, phenyl, or phenyl substituted by halogen;

$R_{39}$ and $R_{40}$ are each independently of the other hydrogen or halogen; and $R_{41}$ is $C_1$-$C_4$alkyl; or a compound of formula XII

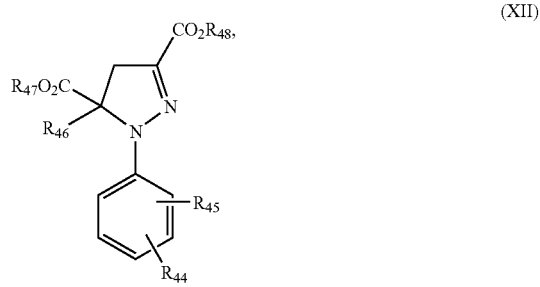

(XII)

wherein $R_{44}$ and $R_{45}$ are each independently of the other hydrogen or halogen, and $R_{46}$, $R_{47}$ and $R_{48}$ are each independently of the others $C_1$-$C_4$alkyl.

The above-mentioned preferences of the compounds of formula I apply also in mixtures of compounds of formula I with the safeners of formulae X to XVIII. Preferred compositions according to the invention comprise a safener selected from the group of formula Xa (Xa)

[Structure: 5-chloroquinoline with 8-O—CH₂—C(O)—O—CH(CH₃)C₅H₁₁-n]

formula Xb (Xb)

[Structure: 5-chloroquinoline with 8-O—CH₂—C(O)—O—CH(CH₃)—CH₂—O—CH₂CH=CH₂]

and formula XIa (XIa)

[Structure: 1-(2-chlorophenyl)-5-phenyl-pyrazole-3-COOCH₃]

Further preferred compounds of formulae X, XI and XII are also listed in Tables 9, 10 and 11.

TABLE 9

Compounds of formula X:

(X)

[Structure: quinoline with $X_6$ at 5-position and 8-O—CH₂—C(O)—O—$R_{37}$]

| Comp. No. | $X_6$ | $R_{37}$ |
|---|---|---|
| 9.01 | Cl | —CH(CH₃)-C₅H₁₁-n |
| 9.02 | Cl | —CH(CH₃)-CH₂OCH₂CH=CH₂ |
| 9.03 | Cl | H |
| 9.04 | Cl | C₄H₉-n |

Preferred compounds of formula XI are listed in the following Table 10.

TABLE 10

Compounds of formula XI:

(XI)

[Structure: 1-aryl-pyrazole/triazole with COOR₄₁ at 3-position, $R_{38}$ at 5-position, E in ring, phenyl with $R_{39}$ and $R_{40}$]

| Comp. No. | $R_{41}$ | $R_{38}$ | $R_{39}$ | $R_{40}$ | E |
|---|---|---|---|---|---|
| 10.01 | CH₃ | phenyl | 2-Cl | H | CH |
| 10.02 | CH₃ | phenyl | 2-Cl | 4-Cl | CH |
| 10.03 | CH₃ | phenyl | 2-F | H | CH |
| 10.04 | CH₃ | 2-chlorophenyl | 2-F | H | CH |
| 10.05 | C₂H₅ | CCl₃ | 2-Cl | 4-Cl | N |
| 10.06 | CH₃ | phenyl | 2-Cl | 4-CF₃ | N |
| 10.07 | CH₃ | phenyl | 2-Cl | 4-CF₃ | N |

Preferred compounds of formula XII are listed in the following Table 11.

TABLE 11

Compounds of formula XII:

(XII)

[Structure: pyrazoline with CO₂$R_{48}$, $R_{47}$O₂C, $R_{46}$, and phenyl with $R_{44}$, $R_{45}$]

| Comp. No. | $R_{46}$ | $R_{47}$ | $R_{48}$ | $R_{44}$ | $R_{45}$ |
|---|---|---|---|---|---|
| 11.01 | CH₃ | CH₃ | CH₃ | 2-Cl | 4-Cl |
| 11.02 | CH₃ | C₂H₅ | CH₃ | 2-Cl | 4-Cl |
| 11.03 | CH₃ | C₂H₅ | C₂H₅ | 2-Cl | 4-Cl |

Preferred compounds of formula XIII are listed in the following Table 12 as compounds of formula XIIIa:

TABLE 1

Compounds of formula XIIIa:

(XIIIa)

$A_2$—C(O)—NHSO$_2$—C$_6$H$_4$—NH—C(O)—N(CH$_3$)(R$_{51}$)

| Comp. No. | $A_2$ | $R_{51}$ |
|---|---|---|
| 12.001 | 2-OCH$_3$-phenyl | H |
| 12.002 | 2,4-di-CH$_3$-phenyl | H |
| 12.003 | 1-methylnaphthyl | CH$_3$ |
| 12.004 | 2-OCH$_3$-phenyl | CH$_3$ |

Preferred compounds of formula XIV are listed in the following Table 13:

TABLE 13

Compounds of formula XIV:

(XIV)

$R_{56}$—N($R_{57}$)—C(O)—CHCl$_2$

| Comp. No. | $R_{56}$ | $R_{57}$ | $R_{56}$ + $R_{57}$ |
|---|---|---|---|
| 13.001 | CH$_2$=CHCH$_2$ | CH$_2$=CHCH$_2$ | — |
| 13.002 | — | — | 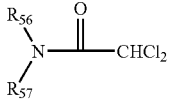 |
| 13.003 | — | — | CH$_3$-CH(OC(CH$_3$)$_3$)-CH$_2$CH$_3$ |
| 13.004 | — | — | 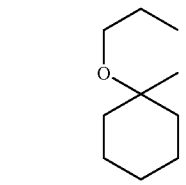 |
| 13.005 | — | — | furan-CH(OC(CH$_3$)$_3$)-CH$_2$CH$_3$ |
| 13.006 | — | — | chroman-CH$_3$ |
| 13.007 | — | — | pyrrolidinone derivative |
| 13.008 | — | — | 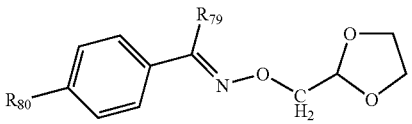 |

Preferred compounds of formula XV are listed in the following Table 14:

TABLE 14

Compounds of formula XV:

(XV)

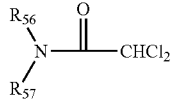

| Comp. No. | $R_{80}$ | $R_{79}$ |
|---|---|---|
| 14.01 | H | CN |
| 14.02 | Cl | CF$_3$ |

Preferred compounds of formula XVI are listed in the following Table 15:

TABLE 15

Compounds of formula XVI:

(XVI)

[Structure: R$_{81}$-phenyl-pyrimidine with two Cl substituents]

| Comp. No. | R$_{81}$ |
|---|---|
| 15.01 | H |
| 15.02 | CH$_3$ |

Preferred compounds of formula XVII are listed in the following Table 16 as compounds of formula XVIIa:

TABLE 16

Compounds of formula XVIIa (XVIIa)

[Structure: bicyclic lactone/lactam with R$_{82}$, (V)$_r$, Z$_4$]

| Comp. No. | R$_{82}$ | Z$_4$ | V | r |
|---|---|---|---|---|
| 16.001 | H | C=CH–O–CH(H)–C(H$_2$)=CH$_2$ | O | 1 |
| 16.002 | H | C=CH–O–CH$_2$–COOCH$_3$ | O | 1 |
| 16.003 | H | C=CH–O–CH$_2$–C≡CH | O | 1 |
| 16.004 | H | C=CH–O–CH$_2$–COOCH(CH$_3$)CH$_2$)$_4$CH$_3$O | O | 1 |
| 16.005 | H | C=CH–O–CH$_2$–COOCH$_3$ | CH$_2$ | 1 |
| 16.006 | H | C=CH–O–CH(CH$_3$)–COOCH$_3$ | CH$_2$ | 1 |
| 16.007 | H | C=CH–O–CH$_2$–COOCH$_3$ | S | 1 |
| 16.008 | H | C=CH–O–CH$_2$–C≡CH | S | 1 |
| 16.009 | H | C=CH–O–CH$_2$–C≡CH | NCH$_3$ | 1 |

TABLE 16-continued

Compounds of formula XVIIa (XVIIa)

| Comp. No. | R$_{82}$ | Z$_4$ | V | r |
|---|---|---|---|---|
| 16.010 | H | C=CH–O–CH$_2$–COOCH$_3$ | NCH$_3$ | 1 |
| 16.011 | H | C=CH–O–CH(CH$_3$)–COOCH$_3$ | NCH$_3$ | 1 |
| 16.012 | H | C=CH–O–CH(CH$_3$)–COOCH$_3$ | O | 1 |
| 16.013 | H | C=CH–O–CH(CH$_3$)–COOCH$_3$ | S | 1 |

Preferred compounds of formula XVII are listed in the following Table 17 as compounds of formula XVIIb:

TABLE 17

Compounds of formula XVIIb (XVIIb)

[Structure: bicyclic with U, R$_{82}$, Z$_4$]

| Comp. No. | U | R$_{82}$ | Z$_4$ |
|---|---|---|---|
| 17.001 | O | H | C=CH–O–CH$_2$–COOCH$_3$ |
| 17.002 | O | H | C=CH–O–CH$_2$–C≡CH |
| 17.003 | O | 5-Cl | C=CH–O–CH$_2$–COOCH$_3$ |
| 17.004 | CH$_2$ | H | C=CH–O–CH$_2$–COOCH$_3$ |
| 17.005 | CH$_2$ | H | C=CH–O–CH$_2$–COO–CH$_2$–phenyl |
| 17.006 | CH$_2$ | H | C=CH–O–CH$_2$–COOC$_2$H$_5$ |

TABLE 17-continued

Compounds of formula XVIIb

(XVIIb)

[Structure: benzofuranone with R82, U, Z4, =O]

| Comp. No. | U | R82 | Z4 |
|---|---|---|---|
| 17.007 | NH2 | 5-Cl | C=CH–O–CH(CH3)–COOCH3 |
| 17.008 | NH2 | 5-Cl | C=CH–O–CH2–C≡CH |
| 17.009 | NH2 | H | C=CH–O–CH2–C≡CH |
| 17.010 | NH2 | H | C=CH–O–CH(CH3)–COOCH3 |
| 17.011 | NCH3 | H | C=CH–O–CH(CH3)–COOCH3 |
| 17.012 | NCH3 | H | C=CH–O–CH2–COOCH3 |

Preferred compounds of formula XVII are listed in the following Table 18 as compounds of formula XVIIc:

TABLE 18

Compounds of formula XVIIc

(XVIIc)

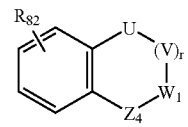

| Comp. No. | U | V | R | W1 | Z4 | R82 |
|---|---|---|---|---|---|---|
| 18.001 | O | C=O | 1 | C=CH–O–CH2–C≡CH | CH2 | H |
| 18.002 | O | C=O | 1 | C=CH–O–CH2–COOCH3 | CH2 | H |
| 18.003 | CH2 | C=O | 1 | C=CH–O–CH(CH3)–COOCH3 | CH2 | H |
| 18.004 | CH2 | C=O | 1 | C=CH–O–CH2–COOCH3 | CH2 | H |
| 18.005 | CH2 | CH2 | 1 | C=CH–O–CH2–COOCH3 | C=H | H |
| 18.006 | CH2 | CH2 | 1 | C=CH–O–CH(CH3)–COOCH3 | C=H | H |
| 18.007 | NCH3 | C=O | 1 | C=CH–O–CH2–C≡CH | CH2 | H |

Preferred compounds of formula XVII are listed in the following Table 19 as compounds of formula XVIId:

TABLE 19

Compounds of formula XVIId (XVIId)

| Comp. No. | $R_{82}$ | $W_1$ |
|---|---|---|
| 19.001 | 6-Cl | C—CH(O—CH$_2$COOCH$_3$) |
| 19.002 | 6-Cl | C=CH—O—CH(CH$_3$)COOCH$_3$ |
| 19.003 | H | C—CH(O—CH$_2$C≡CH) |
| 19.004 | H | C=CH—O—CH(CH$_3$)COOCH$_3$ |
| 19.005 | H | C—CH(O—CH$_2$COOCH$_3$) |

Preferred compounds of formula XVIII are listed in the following Table 20:

TABLE 20

Compounds of formula XVIII (XVIII),

| Comp. No. | $R_{103}$ | $R_{104}$ | $R_{105}$ | $R_{106}$ |
|---|---|---|---|---|
| 20.01 | CH$_3$ | H | cyclopropyl | H |
| 20.02 | CH$_3$ | C$_2$H$_5$ | cyclopropyl | H |
| 20.03 | CH$_3$ | cyclopropyl | C$_2$H$_5$ | H |
| 20.04 | CH$_3$ | CH$_3$ | H | H |
| 20.05 | CH$_3$ | CH$_3$ | cyclopropyl | H |
| 20.06 | CH$_3$ | COH$_3$ | COH$_3$ | H |
| 20.07 | CH$_3$ | COH$_3$ | COH$_3$ | H |
| 20.08 | CH$_3$ | COH$_3$ | CH$_3$ | H |
| 20.09 | CH$_3$ | CH$_3$ | CH$_3$ | H |
| 20.10 | C$_2$H$_5$ | CH$_3$ | CH$_3$ | H |
| 20.11 | C$_2$H$_5$ | COH$_3$ | COH$_3$ | H |
| 20.12 | H | COH$_3$ | COH$_3$ | H |
| 20.13 | H | CH$_3$ | CH$_3$ | H |
| 20.14 | C$_2$H$_5$ | H | H | CH$_3$ |
| 20.15 | H | H | H | CH$_3$ |
| 20.16 | CH$_3$ | H | H | CH$_3$ |
| 20.17 | CH$_3$ | CH$_3$ | H | CH$_3$ |

Of the compounds of formula XXVIII, preference is given to those wherein $R_{148}$ is hydrogen, $C_1$-$C_6$alkyl, $C_3$-$C_8$cycloalkyl or phenyl, wherein the said groups may be substituted by halogen, cyano, nitro, amino, hydroxy, carbonyl, carboxyl, formyl, carbonamide or sulfonamide;

$R_{149}$ is hydrogen;

each $R_{150}$ is independently of any other(s) hydrogen, halogen, $C_1$-$C_4$alkyl, $C_1$-$C_4$haloalkyl, $C_1$-$C_4$alkoxy, $C_1$-$C_4$alkylthio, cyano, nitro or formyl;

$R_{151}$ is hydrogen; and each $R_{152}$ is independently of any other(s) hydrogen, halogen, $C_1$-$C_4$alkyl, $C_1$-$C_4$haloalkyl, $C_1$-$C_4$alkoxy, $C_1$-$C_4$alkylthio, cyano, nitro or formyl.

Especially preferred compounds of formula XXVIII are selected from the group 2-methoxy-N-[4-(2-methoxybenzoylsulfamoyl)phenyl]-acetamide, N-[4-(2-methoxybenzoylsulfamoyl)phenyl]-cyclopropanecarboxamide, N-[4-(2-methoxybenzoylsulfamoyl)phenyl]-cyclobutanecarboxamide, N-[4-(2-chlorobenzoylsulfamoyl)phenyl]-cyclopropanecarboxamide, N-[4-(2-chlorobenzoylsulfamoyl)phenyl]-acetamide, N-[4-(2-trifluoromethoxybenzoylsulfamoyl)phenyl]-acetamide, N-[4-(2-trifluoromethylbenzoylsulfamoyl)phenyl]-cyclopropanecarboxamide, N-[4-(2-trifluoromethoxybenzoylsulfamoyl)phenyl]-cyclopropanecarboxamide, N-[4-(2-trifluoromethoxybenzoylsulfamoyl)phenyl]-cyclobutanecarboxamide and N-[4-(2-trifluoromethylbenzoylsulfamoyl)phenyl]-acetamide.

Of the compounds of formula XXIX, preference is given to those wherein $R_{159}$ is hydrogen, formyl, $C_{1-6}$alkylcarbonyl, $C_{1-6}$alkenylcarbonyl, $C_{1-6}$alkynylcarbonyl, $C_{1-6}$alkoxycarbonyl, $C_{1-6}$alkylthiocarbonyl, $C_{3-8}$cycloalkylcarbonyl, phenyl-$C_{1-6}$alkylcarbonyl or phenylcarbonyl, wherein the afore-mentioned hydrocarbon radicals may be substituted by one or more halogen atoms, cyano, nitro, amino, methoxy, ethoxy or phenyl;

$R_{153}$ is hydrogen, $C_{1-6}$alkyl, $C_{1-6}$alkenyl, $C_{1-6}$alkynyl, formyl, $C_{1-6}$alkylcarbonyl or $C_{1-6}$alkoxycarbonyl, wherein the afore-mentioned hydrocarbon radicals may be substituted by one or more halogen atoms, cyano, nitro, amino, methoxy, ethoxy or phenyl;

$R_{154}$ is hydrogen, $C_{1-6}$alkyl, $C_{1-6}$alkenyl, $C_{1-6}$alkynyl, formyl, $C_{1-6}$alkylcarbonyl or $C_{1-6}$alkoxycarbonyl, wherein the afore-mentioned hydrocarbon radicals may be substituted by one or more halogen atoms, cyano, nitro, amino, methoxy, ethoxy or phenyl;

$R_{155}$, $R_{156}$, $R_{157}$ and $R_{158}$ are each independently of the others hydrogen, halogen, cyano, nitro, formyl, carboxyl, $C_{1-6}$alkoxy, $C_{1-6}$haloalkoxy, $C_{1-6}$alkylcarbonyl, $C_{1-6}$alkoxycarboxyl, $C_{1-6}$alkyl or $C_{1-6}$haloalkyl;

or $R_{153}$ and $R_{158}$, together with the ring atoms to which they are bonded, form a five- or six-membered, partially saturated or unsaturated ring that may contain up to 2 identical or different hetero atoms from the group oxygen, sulfur and nitrogen, it being possible for that ring to be substituted by an oxo radical.

Special preference is given to compounds of formula XXIX wherein $R_{159}$ is hydrogen, formyl, $C_{1-6}$alkylcarbonyl, $C_{1-6}$alkenylcarbonyl, $C_{1-6}$alkynylcarbonyl, $C_{1-6}$alkoxycarbonyl, $C_{1-6}$alkylthiocarbonyl, $C_{3-8}$cycloalkylcarbonyl or phenylcarbonyl;

$R_{153}$ is hydrogen, $C_{1-6}$alkyl, $C_{1-6}$alkenyl, $C_{1-6}$alkynyl, formyl, $C_{1-6}$alkylcarbonyl or $C_{1-6}$alkoxycarbonyl;

$R_{154}$ is hydrogen, $C_{1-6}$alkyl, $C_{1-6}$alkenyl, $C_{1-6}$alkynyl, formyl, $C_{1-6}$alkylcarbonyl or $C_{1-6}$alkoxycarbonyl;

$R_{155}$, $R_{156}$, $R_{157}$, and $R_{158}$ are each independently of the others hydrogen, halogen, cyano, nitro, formyl, $C_{1-6}$alkyl, $C_{1-6}$haloalkyl, $C_{1-6}$alkoxy or $C_{1-6}$haloalkoxy;

or $R_{153}$ and $R_{158}$, together with the ring atoms to which they are bonded, form a five- or six-membered, partially saturated or unsaturated ring that may contain up to 2 identical or different hetero atoms from the group oxygen, sulfur and nitrogen, it being possible for that ring to be substituted by an oxo radical.

Very special preference is given to compounds of formula XXIX selected from the group 4-hydroxy-1-methyl-3-(1H-tetrazole-5-carbonyl)-1H-quinolin-2-one, 1-ethyl-4-hydroxy-3-(1H-tetrazole-5-carbonyl)-1H-quinolin-2-one, 6-hydroxy-5-(1H-tetrazole-5-carbonyl)-1,2-dihydro-pyrrolo [3.2. 1-.ij.]quinolin-4-one, 3-(1-acetyl-1H-tetrazole-5-carbonyl)-4-hydroxy-1-methyl-1H-quinolin-2-one, 6-chloro-4-hydroxy-1-methyl-3-(1H-tetrazole-5-carbonyl)-1H-quinolin-2-one, 6-fluoro-4-hydroxy-1-methyl-3-(1H-tetrazole-5-carbonyl)-1H-quinolin-2-one, 4-hydroxy-1,6-dimethyl-3-(1H-tetrazole-5-carbonyl )-1H-quinolin-2-one, 4-hydroxy-6-methoxy-1-methyl-3-(1H-tetrazole-5-carbonyl)-1H-quinolin-2-one, 4-hydroxy-6-methoxy-1-methyl-3-(1H-tetrazole-5-carbonyl)-1H-quinolin-2-one, acetic acid 1-methyl-2-oxo-3-(1H-tetrazole-5-carbonyl)-1,2-dihydro-quinolin-4-yl ester and 2,2-dimethylpropionic acid 1-methyl-2-oxo-3-(1H-tetrazole-5-carbonyl)-1,2-dihydroquinolin-4-yl ester.

The invention relates also to a method for the selective control of weeds in crops of useful plants, which comprises treating the useful plants, the seeds or cuttings thereof or the area of cultivation thereof simultaneously or separately with a herbicidally effective amount of a herbicide of formula I and a herbicide-antagonistically effective amount of a safener of formula X, XI, XII, XIII, XIV, XV, XVI, XVII, XVIII, XIX, XX, XXI, XXII, XXIII, XXIV, XXV, XXVI, XXVII, XXVIII or XXIX, preferably of formula X, XI, XII, XIII, XIV, XV, XVI, XVII or XVIII.

Suitable cultivated plants that can be protected against the harmful effect of the above-mentioned herbicides by the safeners of formula X, XI, XII, XIII, XIV, XV, XVI, XVII or XVIII are especially cereals, cotton, soybeans, sugar beet, sugar cane, plantation crops, rape, maize and rice, more especially maize and cereals. Crops are also to be understood as including those that have been rendered tolerant to herbicides or classes of herbicides by conventional breeding or genetic engineering methods.

The weeds to be controlled may be either monocotyledonous or dicotyledonous weeds, for example the monocotyledonous weeds *Avena, Agrostis, Phalaris, Lolium, Bromus, Alopecurus, Setaria, Digitara, Brachiaria, Echinochloa, Panicum, Sorghum* hal./bic., *Rottboellia, Cyperus, Brachiaria, Echinochloa, Scirpus, Monochoria, Sagittaria* and *Stellaria* and the dicotyledenous weeds *Sinapis, Chenopodium, Galium, Viola, Veronica, Matricaria, Papaver, Solanum, Abutilon, Sida, Xanthium, Amaranthus, Ipomoea* and *Chrysanthemum*.

Areas of cultivation are areas of land on which the cultivated plants are already growing or in which the seeds of those cultivated plants have already been sown, as well as the areas of land on which it is intended to grow those cultivated plants.

A safener of formula X, XI, XII, XIII, XIV, XV, XVI, XVII, XVIII, XIX, XX, XXI, XXII, XXIII, XXIV, XXV, XXVI, XXVII, XXVIII or XXIX may, depending on the intended purpose, be used to pretreat the seed material of the cultivated plant (dressing the seed or the cuttings) or may be incorporated into the soil before or after sowing. It can, however, also be applied alone or together with the herbicide after the emergence of the plants. The treatment of the plants or seed with the safener can therefore, in principle, be effected independently of the time at which the herbicide is applied. The treatment of the plants can, however, also be carried out by applying the herbicide and safener simultaneously (for example in the form of a tank mixture). The rate of application of the safener in relation to the herbicide depends largely on the method of application. In the case of field treatment, which is effected either using a tank mixture comprising a combination of safener and herbicide or by the separate application of safener and herbicide, the ratio of herbicide to safener is generally from 100:1 to 1:10, preferably from 20:1 to 1:1. In the case of field treatment, from 0.001 to 1.0 kg of safener/ha, preferably from 0.001 to 0.25 kg of safener/ha, is generally applied.

The rate of application of herbicide is generally from 0.001 to 2 kg/ha, but is preferably from 0.005 to 0.5 kg/ha.

The compositions according to the invention are suitable for any of the methods of application customary in agriculture, for example pre-emergence application, post-emergence application and seed dressing.

In the case of seed dressing, from 0.001 to 10 g of safener/kg of seed, preferably from 0.05 to 2 g of safener/kg of seed, is generally applied. When the safener is applied in liquid form shortly before sowing, with swelling of the seed, it is advantageous to use safener solutions that comprise the active ingredient in a concentration of from 1 to 10 000 ppm, preferably from 100 to 1000 ppm.

For application, the safeners of formula X, XI, XII, XIII, XIV, XV, XVI, XVII, XVIII, XIX, XX, XXI, XXII, XXIII, XXIV, XXV, XXVI, XXVII, XXVIII or XXIX, or combinations of those safeners with the herbicides of formula I, are advantageously processed, together with the adjuvants customary in formulation technology, into formulations, for example into emulsifiable concentrates, coatable pastes, directly sprayable or dilutable solutions, dilute emulsions, wettable powders, soluble powders, dusts, granules or microcapsules.

Such formulations are described, for example, in WO 97/34485, on pages 9 to 13. The formulations are prepared in known manner, e.g. by intimately mixing and/or grinding the active ingredients with liquid or solid formulation adjuvants, for example solvents or solid carriers. Furthermore, in addition surface-active compounds (surfactants) can be used in the preparation of the formulations. Solvents and solid carriers suitable for that purpose are mentioned, for example, in WO 97/34485, on page 6.

Depending on the nature of the active ingredient of formula I to be formulated, there come into consideration as surface-active compounds non-ionic, cationic and/or anionic surfactants and mixtures of surfactants having good emulsifying, dispersing and wetting properties. Examples of suitable anionic, non-ionic and cationic surfactants are listed, for example, in WO 97/34485 on pages 7 and 8. Also suitable for the preparation of the herbicidal compositions according to the invention are the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I-Ill, Chemical Publishing Co., New York, 1980-81.

The herbicidal formulations generally contain from 0.1 to 99% by weight, especially from 0.1 to 95% by weight, of active ingredient mixture comprising the compound of formula I and the compounds of formulae X, XI, XII, XIII, XIV, XV, XVI, XVII, XVIII, XIX, XX, XXI, XXII, XXIII, XXIV, XXV, XXVI, XXVII, XXVIII or XXIX, from 1 to 99.9% by weight of a solid or liquid formulation adjuvant and from 0 to 25% by weight, especially from 0.1 to 25% by weight, of a surfactant. Whereas commercial products will usually preferably be formulated as concentrates, the end user will normally employ dilute formulations.

The compositions may also comprise further additives, such as stabilisers, vegetable oils or epoxidised vegetable oils (epoxidised coconut oil, rapeseed oil or soybean oil), antifoams, e.g. silicone oil, preservatives, viscosity regulators, binders, tackifiers and also fertilisers or other active ingredients. There are various suitable methods and techniques for using safeners of formulae X, XI, XII, XIII, XIV, XV, XVI, XVII, XVIII, XIX, XX, XXI, XXII, XXIII, XXIV, XXV, XXVI, XXVII, XXVIII or XXIX or compositions comprising them to protect cultivated plants against the harmful effects of herbicides of formula I; the following are examples:

i) Seed Dressing a) Dressing the seeds with a wettable powder formulation of an active ingredient of formula X, XI, XII, XIII, XIV, XV, XVI, XVII, XVIII, XIX, XX, XXI, XXII, XXIII, XXIV, XXV, XXVI, XXVII, XXVIII or XXIX, by shaking in a vessel until the formulation is uniformly distributed on the seed surface (dry dressing). Approximately from 1 to 500 g of active ingredient of formula X, XI, XII, XIII, XIV, XV, XVI, XVII, XVIII, XIX, XX, XXI, XXII, XXIII, XXIV, XXV, XXVI, XXVII, XXVIII or XXIX (from 4 g to 2 kg of wettable powder) are used per 100 kg of seed.

b) Dressing the seeds with an emulsifiable concentrate of an active ingredient of formula X, XI, XII, XIII, XIV, XV, XVI, XVII, XVIII, XIX, XX, XXI, XXII, XXIII, XXIV, XXV, XXVI, XXVII, XXVIII or XXIX in accordance with method a) (wet dressing).

c) Dressing by immersing the seeds in a liquid formulation containing from 100 to 1000 ppm of active ingredient of formula X, XI, XII, XIII, XIV, XV, XVI, XVII, XVIII, XIX, XX, XXI, XXII, XXIII, XXIV, XXV, XXVI, XXVII, XXVIII or XXIX for from 1 to 72 hours and, if desired, subsequently drying the seeds (immersion dressing).

Dressing the seeds or treating the germinated seedlings are naturally the preferred methods of application, because treatment with the active ingredient is directed wholly at the target crop. From 1 to 1000 g of antidote, preferably from 5 to 250 g of antidote, is generally used per 100 kg of seed, although depending on the method employed, which also allows the addition of other active ingredients or micronutrients, amounts that exceed or fall short of the specified concentration limits may be employed (repeat dressing).

ii) Application in the Form of a Tank Mixture

A liquid formulation of a mixture of antidote and herbicide (ratio of the one to the other from 10:1 to 1:100) is used, the rate of application of herbicide being from 0.005 to 5.0 kg per hectare. Such tank mixtures are applied before or after sowing.

iii) Application to the Seed Furrow

The active ingredient of formula X, XI, XII, XIII, XIV, XV, XVI, XVII, XVIII, XIX, XX, XXI, XXII, XXIII, XXIV, XXV, XXVI, XXVII, XXVIII or XXIX is introduced into the open, sown seed furrow in the form of an emulsifiable concentrate, wettable powder or granules. After the seed furrow has been covered, the herbicide is applied pre-emergence in the normal manner.

iv) Controlled Active Ingredient Release

The active ingredient of formula X, XI, XII, XIII, XIV, XV, XVI, XVII, XVIII, XIX, XX, XXI, XXII, XXIII, XXIV, XXV, XXVI, XXVII, XXVIII or XXIX is applied in solution to mineral granule carriers or polymerised granules (urea/formaldehyde) and dried. Where appropriate, it is also possible to apply a coating (coated granules) that allows the active ingredient to be released in metered amounts over a specific period.

The activity of herbicidal and plant growth-inhibiting compositions according to the invention comprising a herbicidally effective amount of compound of formula I and a herbicide-antagonistically effective amount of compound of formula X, XI, XII, XIII, XIV, XV, XVI, XVII, XVIII, XIX, XX, XXI, XXII, XXIII, XXIV, XXV, XXVI, XXVII, XXVIII or XXIX can be increased by the addition of spray tank adjuvants.

Such adjuvants may be, for example: non-ionic surfactants, mixtures of non-ionic surfactants, mixtures of anionic surfactants with non-ionic surfactants, cationic surfactants, organosilicon surfactants, mineral oil derivatives with and without surfactants, vegetable oil derivatives with and without the addition of surfactant, alkylated derivatives of oils of vegetable or mineral origin with and without surfactants, fish oils and other animal oils of animal nature and alkyl derivatives thereof with and without surfactants, naturally occurring higher fatty acids, preferably having from 8 to 28 carbon atoms, and alkyl ester derivatives thereof, organic acids containing an aromatic ring system and one or more carboxylic acid esters, and alkyl derivatives thereof, and also suspensions of polymers of vinyl acetate or copolymers of vinyl acetate/acrylic acid esters. Mixtures of individual adjuvants with one another and combined with organic solvents may lead to the activity being further increased.

Suitable non-ionic surfactants include, for example, polyglycol ether derivatives of aliphatic or cycloaliphatic alcohols, of saturated or unsaturated fatty acids and alkylphenols, preferably that can contain from 3 to 30 glycol ether groups and from 8 to 20 carbon atoms in the (aliphatic) hydrocarbon radical and from 6 to 18 carbon atoms in the alkyl radical of the alkylphenols.

Further suitable non-ionic surfactants are the water-soluble polyethylene oxide adducts of polypropylene glycol, ethylenediaminopolypropylene glycol and alkyl polypropylene glycol having preferably from 1 to 10 carbon atoms in the alkyl chain, which adducts contain preferably from 20 to 250 ethylene glycol ether groups and from 10 to 100 propylene glycol ether groups. The said compounds usually contain from 1 to 5 ethylene glycol units per propylene glycol unit.

There may also be mentioned, as further examples of non-ionic surfactants, nonylphenol polyethoxyethanols, castor oil polyglycol ethers, polypropylene/polyethylene oxide adducts, tributylphenoxypolyethoxy ethanol, polyethylene glycol and octylphenoxypolyethoxyethanol.

Fatty acid esters of polyoxyethylenesorbitan, e.g. polyoxyethylenesorbitan trioleate, are also suitable.

Preferred anionic surfactants are especially alkyl sulfates, alkyl sulfonates, alkylaryl sulfonates, alkylated phosphoric acids, and ethoxylated derivatives thereof. The alkyl radicals usually contain from 8 to 24 carbon atoms.

Preferred non-ionic surfactants are known by the following trade names:

polyoxyethylene cocoalkylamine (e.g. AMIET® 105 (Kao Co.)), polyoxyethylene oleylamine (e.g. AMIET® 415 (Kao Co.)), nonylphenol polyethoxyethanols, polyoxyethylene stearylamine (e.g. AMIET® 320 (Kao Co.)), N-polyethoxyethylamines (e.g. GENAMIN® (Hoechst AG)), N,N,N',N'-tetra(polyethoxypolypropoxyethyl)ethylenediamine (e.g. TERRONIL® and TETRONIC®(BASF Wyandotte Corp.)), BRIJ® (Atlas Chemicals), ETHYLAN® CD and ETHYLAN® D (Diamond Shamrock), GENAPOL® C, GENAPOL® O, GENAPOL® S and GENAPOL® X080 (Hoechst AG), EMULGEN® 104P, EMULGEN® 109P and EMULGEN® 408 (Kao Co.); DISTY® 125 (Geronazzo), SOPROPHOR® CY 18 (Rhone Poulenc S.A.); NONISOL® (Ciba-Geigy), MRYJ® (ICI); TWEEN® (ICI); EMULSOGEN® (Hoechst AG); AMIDOX® (Stephan Chemical Co.), ETHOMID® (Armak Co.); PLURONIC® (BASF Wyandotte Corp.), SOPROPHOR® 461 P (Rhône Poulenc S.A.), SOPROPHOR® 496/P (Rhone Poulenc S.A.), ANTAROX FM-63 (Rhone Poulenc S.A.), SLYGARD 309 (Dow Corning), SILWET 408, SILWET L-7607N (Osi-Specialities).

The cationic surfactants are especially quaternary ammonium salts that contain as N-substituent(s) at least one alkyl radical having from 8 to 22 carbon atoms and, as further substituents, optionally halogenated lower alkyl, benzyl or hydroxy-lower alkyl radicals. The salts are preferably in the form of halides, methyl sulfates or ethyl sulfates, for example stearyltrimethylammonium chloride or benzyldi(2-chloroethyl)ethylammonium bromide.

The oils used are either of mineral or natural origin. The natural oils can in addition be of animal or vegetable origin. Of the animal oils preference is given especially to derivatives of beef tallow, but fish oils (e.g. sardine oil) and derivatives thereof are also used. Vegetable oils are mostly seed oils of varied origin. Examples of vegetable oils used especially that may be mentioned include coconut oil, rapeseed oil and sunflower oil and derivatives thereof.

In the composition according to the invention, the concentrations of oil additive are generally from 0.01 to 2% based on the spray mixture. The oil additive can, for example, be added to the spray tank in the desired concentration after the spray mixture has been prepared.

Preferred oil additives in the composition according to the invention comprise an oil of vegetable origin, for example rapeseed oil or sunflower oil, alkyl esters of oils of vegetable origin, for example methyl derivatives, or mineral oils.

Especially preferred oil additives comprise alkyl esters of higher fatty acids ($C_8$-$C_{22}$), especially methyl derivatives of $C_{12}$-$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9).

The application and action of the oil additives can be improved by combining them with surface-active substances, such as non-ionic, anionic or cationic surfactants. Examples of suitable anionic, non-ionic and cationic surfactants are listed in WO 97/34485 on pages 7 and 8.

Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available preferred surfactants are the Genapol types (Clariant AG, Muttenz, Switzerland). The concentration of the surface-active substances in relation to the total additive is generally from 1 to 30% by weight.

Examples of oil additives that consist of mixtures of oils or mineral oils, or derivatives thereof, with surfactants include Edenor ME SU®, Emery 22310 (Henkel subsidiary Cognis GMBH, DE), Turbocharge® (Zeneca Agro, Stoney Creek, Ontario, Calif.) or, more especially, Actipron®) (BP Oil UK Limited, GB).

The addition of an organic solvent to the oil additive/surfactant mixture can also bring about further increase in activity. Suitable solvents include, for example, Solvesso® (ESSO) and Aromatic Solvent® (Exxon Corporation) types.

The concentration of such solvents can be from 10 to 80%, by weight, of the total weight.

Such oil additives, which, for example, are also described in U.S. Pat. No. 4,834,908, are especially preferred for the composition according to the invention. A more especially preferred oil additive is known by the name MERGE®, can be obtained from BASF Corporation and is basically described, for example, in U.S. Pat. No. 4,834,908, col. 5, as Example COC-1. A further oil additive that is preferred in accordance with the invention is SCORE® (Novartis Crop Protection Canada).

Surfactants, oils, especially vegetable oils, derivatives thereof, such as alkylated fatty acids and mixtures thereof, for example with preferably anionic surfactants, such as alkylated phosphoric acids, alkyl sulfates and alkylaryl sulfonates and also higher fatty acids, that are customary in formulation and adjuvant technology and that can also be used in the compositions according to the invention and in spray tank solutions thereof, are described, inter alia, in "McCutcheon's Detergents and Emulsifiers Annual" MC Publishing Corp., Ridgewood N.J., 1998, Stache, H., "Tensid-Taschenbuch", Carl Hanser Verlag, Munich/Vienna, 1990, M. and J. Ash, "Encyclopedia of Surfactants", Vol I-IV, Chemical Publishing Co., New York, 1981-89, G. Kapusta, "A Compendium of Herbicide Adjuvants", Southern Illinois Univ., 1998, L. Thomson Harvey, "A Guide to Agricultural Spray Adjuvants Used in the United States", Thomson Pubns., 1992.

Preferred formulations have especially the following compositions (%=percent by weight)

| Emulsifiable concentrates: | |
|---|---|
| active ingredient mixture: | from 1 to 90%, preferably from 5 to 20% |
| surface-active agent: | from 1 to 30%, preferably from 10 to 20% |
| liquid carrier: | from 5 to 94%, preferably from 70 to 85% |
| Dusts: | |
| active ingredient mixture: | from 0.1 to 10%, preferably from 0.1 to 5% |
| solid carrier: | from 99.9 to 90%, preferably from 99.9 to 99% |
| Suspension concentrates: | |
| active ingredient mixture: | from 5 to 75%, preferably from 10 to 50% |
| water: | from 94 to 24%, preferably from 88 to 30% |
| surface-active agent: | from 1 to 40%, preferably from 2 to 30% |
| Wettable powders: | |
| active ingredient mixture: | from 0.5 to 90%, preferably from 1 to 80% |
| surface-active agent: | from 0.5 to 20%, preferably from 1 to 15% |
| solid carrier: | from 5 to 95%, preferably from 15 to 90% |
| Granules: | |
| active ingredient mixture: | from 0.1 to 30%, preferably from 0.1 to 15% |
| solid carrier: | from 99.5 to 70%, preferably from 97 to 85% |

The Examples that follow illustrate the invention further. They do not limit the invention.

Formulation Examples for mixtures of herbicides of formula I and safener of formula X, XI, XII, XIII, XIV, XV, XVI, XVII, XVIII, XIX, XX, XXI, XXII, XXIII, XXIV, XXV, XXVI, XXVII, XXVIII or XXIX (%=percent by weight)

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| cyclohexanone | — | — | 10% | 20% |
| aromatic $C_9$-$C_{12}$ hydrocarbon mixture | 85% | 78% | 55% | 16% |

Emulsions of any desired concentration can be prepared from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol (mol. wt. 400) | 20% | 10% | — | — |
| N-methyl-2-pyrrolidone | — | — | 30% | 10% |
| aromatic $C_9$-$C_{12}$ hydrocarbon mixture | 75% | 60% | — | — |

The solutions are suitable for application in the form of micro-drops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier material ($\varnothing$ 0.1-1 mm) for example $CaCO_3$ or $SiO_2$ | 99.0% | 93% | 83% |

The active ingredient is dissolved in methylene chloride, the solution is sprayed onto the carrier, and the solvent is subsequently evaporated off in vacuo.

| F5. Coated granules | a) | b) | c) |
|---|---|---|---|
| active ingredient mixture | 0.1% | 5% | 15% |
| polyethylene glycol (mol. wt. 200) | 1.0% | 2% | 3% |
| highly dispersed silicic acid | 0.9% | 1% | 2% |
| inorganic carrier material ($\varnothing$ 0.1-1 mm) for example $CaCO_3$ or $SiO_2$ | 98.0% | 92% | 80% |

The finely ground active ingredient is uniformly applied, in a mixer, to the carrier material moistened with polyethylene glycol, yielding non-dusty coated granules.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed with the adjuvants, and the mixture is ground, moistened with water, extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical to formulate the active ingredient of formula I and the mixing partner of formula X, XI, XII, XIII, XIV, XV, XVI, XVII, XVIII, XIX, XX, XXI, XXII, XXIII, XXIV, XXV, XXVI, XXVII, XXVIII or XXIX separately and then, shortly before application, to bring them together in the applicator in the desired mixing ratio in the form of a "tank mixture" in water.

The ability of the safeners of formula X, XI, XII, XIII, XIV, XV, XVI, XVII, XVIII, XIX, XX, XXI, XXII, XXIII, XXIV, XXV, XXVI, XXVII, XXVIII or XXIX to protect cultivated plants against the phytotoxic action of herbicides of formula I is illustrated in the following Examples.

BIOLOGICAL EXAMPLE 1

Safening Action

Under greenhouse conditions, the test plants are grown in plastics pots to the 4-leaf stage. At that stage, on the one hand the herbicide alone, and on the other hand mixtures of the herbicide with the test substances to be tested as safeners, are applied to the test plants. The test substances are applied in the form of an aqueous suspension prepared from a 25% wettable powder (Example F3, b)), using 500 litres of water/ha. 2 to 3 weeks after application, the phytotoxic action of the herbicide on the cultivated plants, for example maize and cereals, is evaluated using a percentage scale. 100% indicates that the test plant has died, and 0% indicates no phytotoxic action.

The results obtained in this test demonstrate that the damage caused to the cultivated plant by the herbicide of formula I can be appreciably reduced by the compounds of formula X, XI, XII, XIII, XIV, XV, XVI, XVII, XVIII, XIX, XX, XXI, XXII, XXIII, XXIV, XXV, XXVI, XXVII, XXVIII or XXIX. Examples of those results are given in the following Table B5:

TABLE B5

Post-emergence action of a mixture according to the invention of herbicide and safener:

| Test plant | Comp. No. 1.01 (60 g/ha) | Comp. No. 1.01 (60 g/ha) + Comp. No. 11.03 (15 g/ha) |
|---|---|---|
| Barley | 20 | 0 |
| Agrostis | 70 | 70 |
| Alopecurus | 70 | 80 |
| Lolium | 70 | 70 |

It can be seen from Table 5 that compound No. 1.01 exhibits a phytotoxic effect of 20% on barley, which is not tolerable. The weeds *Agrostis, Alopecurus* und *Lolium* are satisfactorily controlled.

In contrast, the mixture according to the invention, consisting of herbicide No. 1.01 and safener No. 11.03, has no phytotoxic effect on the cultivated plant. At the same time, the herbicidal effect on the weeds is not only identical but surprisingly, in the case of *Alopecurus*, even increased (80% compared with the 70% achieved with the application of herbicide No. 1.01 on its own).

The same results are obtained when the mixtures are formulated in accordance with Examples F1, F2 and F4 to F8.

The compound of formula I can advantageously be mixed with a number of other known herbicides. As a result, for example, the spectrum of weeds is substantially broadened and in many cases an increase in selectivity with respect to the useful plants is achieved. In particular, mixtures of the compound of formula I with at least one of the following herbicides are important:

herbicides from the class of the phenoxy-phenoxypropionic acids, for example diclofop-methyl, fluazifop-P-butyl, quizalafop-P-ethyl, propaquizafop, clodinafop-P-propargyl, cyhalofop-butyl, fenoxaprop-P-ethyl, haloxyfop-methyl or haloxyfop-etoethyl;

herbicides from the class of the hydroxylamines, for example sethoxidim, alloxydim, clethodim, cycloxydim, tepralkoxydim, tralkoxydim or butroxidim;

herbicides from the class of the sulfonylureas, for example amidosulfuron, azimsulfuron, bensulfuron-methyl, chlorimuron-ethyl, cinosulfuron, chlorsulfuron, chlorimuron, cyclosulfamuron, ethametsulfuron-methyl, ethoxysulfuron, fluazasulfuron, flupyrsulfuron, imazosulfuron, iodosulfuron (CAS RN 144550-36-7 and 185119-76-0), metsulfuron-methyl, nicosulfuron, oxasulfuron, primisulfuron, pyrazosulfuron-ethyl, sulfosulfuron, rimsulfuron, thifensulfuron-methyl, triasulfuron, tribenuron-methyl, triflusulfuron-methyl, prosulfuron, flucarbazone ortritosulfuron (CAS RN 142469-14-5);

herbicides from the class of the imidazolinones, such as imazethapyr, imazamethabenz, imazamethapyr, imazaquin, imazamox or imazapyr;

herbicides from the class of the pyrimidines, such as pyrithiobac-sodium, pyriminobac, bispyribac-sodium;

herbicides from the class of the triazines, for example atrazine, simazine, simethryne, terbutryne, terbuthylazine;

herbicides from the class of the ureas, such as isoproturon, chlortoluron, diuron, dymron, fluometuron, linuron or methabenzthiazuron;

herbicides from the class of the phosphonic acid derivatives, for example glyphosate, glufosinate, sulfosate or phosphinothricin;

herbicides from the class of the PPO, for example nitrofen, bifenox, acifluorfen, lactofen, oxyfluorfen, ethoxyfen, fluoroglycofen, fomesafen, halosafen, azafenidin (CAS RN.-68049-83-2), benzfendizone (CAS RN 158755-954), butafenacil (known from U.S. Pat. No. 5,183,492, CAS RN 158755-954), carfentrazone-ethyl, cinidon-ethyl (CAS RN 142891-20-1), flumichlorac-pentyl, flumioxazin, fluthiacet-methyl, oxadiargyl, oxadiazon, pentoxazone, sulfentrazone, fluazolate (CAS RN 174514-07-9) or pyraflufen-ethyl;

herbicides from the class of the chloroacetanilides, for example alachlor, acetochlor, butachlor, dimethachlor, dimethenamid, S-dimethenamid, metazachlor, metolachlor, S-metolachlor, pretilachlor, propachlor, propisochlor, thenylchlor or pethoamid (CASRN 106700-29-2)

herbicides from the class of the phenoxyacetic acids, for example 2,4-D, fluroxypyr, MCPA, MCPP, MCPB, trichlorpyr or mecropop-P;

herbicides from the class of the triazinones, for example hexazinone, metamitron or metribuzin;

herbicides from the class of the dinitroanilines, for example oryzalin, pendimethalin or trifluralin;

herbicides from the class of the azinones, for example chloridazon or norflurazon;

herbicides from the class of the carbamates, for example chlorpropham, desmedipham, phenmedipham or propham;

herbicides from the class of the oxyacetamides, for example mefenacet or fluthiacet;

herbicides from the class of the thiolcarbamates, for example butylate, cycloate, diallate, EPTC, esprocarb, molinate, prosulfocarb, thiobencarb or triallate;

herbicides from the class of the azoloureas, for example fentrazamide (CAS RN1 58237-07-1) or cafenstrole;

herbicides from the class of the benzoic acids, for example dicamba or picloram;

herbicides from the class of the anilides, for example diflufenican, or propanil;

herbicides from the class of the nitriles, for example bromoxynil, dichlobenil or ioxynil;

herbicides from the class of the triones, for example sulcotrione, mesotrione (known from U.S. Pat. No. 5,006,158), isoxaflutole or isoxachlortole;

herbicides from the class of the sulfonamides, for example flucarbazone (CAS RN 181274-17-9), procarbazone (CAS RN 145026-81-9), chlorasulam, diclosulam (CAS RN 145701-21-9), florasulam, flumetsulam or metosulam;

and also amitrole, benfuresate, bentazone, cinmethylin, clomazone, chlopyralid, difenzoquat, dithiopyr, ethofumesate, flurochloridone, indanofan, isoxaben, oxaziclomefone, pyridate, pyridafol (CAS RN. 40020-01-7), quinchlorac, quinmerac, tridiphane or flamprop.

Unless specified otherwise, the above-mentioned mixing partners of the compound of formula I are known from The Pesticide Manual, Eleventh Edition, 1997, BCPC. The mixing partners of the compound of formula I can, if desired, also be in the form of esters or salts, as mentioned, for example, in The Pesticide Manual, Eleventh Edition, 1997, BCPC.

The following Examples illustrate the invention further without implying any limitation.

PREPARATION EXAMPLES

Example P1

Preparation of (8):

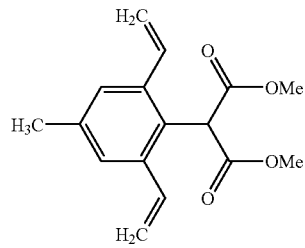

To a solution of 20 g of 2-(2,6-dibromo-4-methyl-phenyl)-malonic acid dimethyl ester (52.6 mmol) in 400 ml of toluene (degassed 3 times, vacuum/argon) there are added first 36.7 g (0.116 mol) of tributylvinylstannane and then 2 g of tetrakis(triphenylphosphine)-palladium. The reaction mixture is then stirred for 9 hours at a temperature of from 90 to 95° C. After filtration over Hyflo and concentration using a rotary evaporator, and after purification by chromatography, 15.3 g of (8) are obtained in the form of a yellow oil, which is used in the next reaction without being further purified.

Example P2

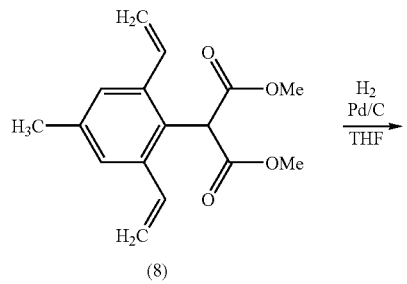

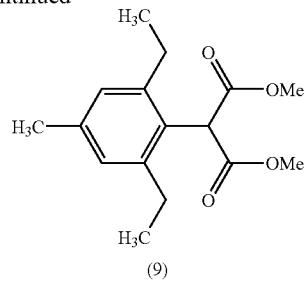

15.2 g of compound (8) obtained according to Example P1 are hydrogenated with hydrogen over a palladium catalyst (carbon as carrier, 7 g of 5% Pd/C) in 160 ml of tetrahydrofuran at a temperature of from 20 to 25° C. When the hydrogenation is complete, the product is filtered over Hyflo and the filtrate obtained is concentrated using a rotary evaporator. 13.7 g of (9) are obtained in the form of yellow crystals having a melting point of from 47 to 49° C.

Example P3

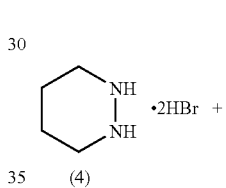

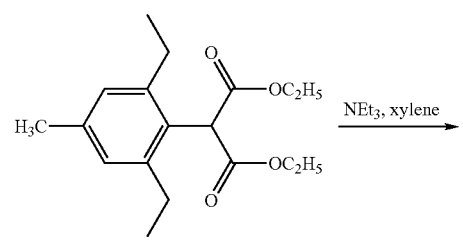

71.8 g (0.71 mol) of triethylamine are added to a suspension of 40 g (0.15 mol) of (4) in 1000 ml of xylene and the mixture is degassed (4 times, vacuum/argon). The yellow suspension is then heated to a temperature of 60° C. and stirred for 3 hours. 42.5 g (0.15 mol) of (5) are subsequently added and the mixture is heated to a bath temperature of 150° C. in order continuously to distill off excess triethylamine and the resulting ethanol. After 3 hours, the reaction mixture is cooled to a temperature of 40° C. and introduced into 500 ml of an ice/water mixture. The reaction mixture is rendered alkaline using 100 ml of aqueous 1N sodium hydroxide solution, and the aqueous phase (containing the product) is washed twice with ethyl acetate. After then washing the organic phase twice with aqueous 1N sodium hydroxide solution, the aqueous phases are combined, the remaining xylene is distilled off and the combined aqueous phases are adjusted to pH 2-3 using 4N HCl with cooling. The precipitated product obtained is poured onto a suction filter, and the filtration residue is washed with water and briefly with hexane, and then dried in vacuo at a temperature of 60° C. over $P_2O_5$. 34.6 g of (6) are obtained in the form of a slightly beige solid having a melting point of from 242 to 244° C. (decomposition).

Example P4

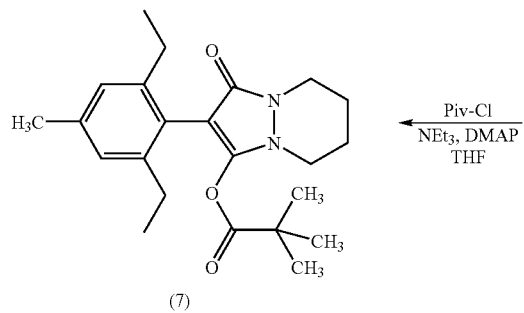

(7)

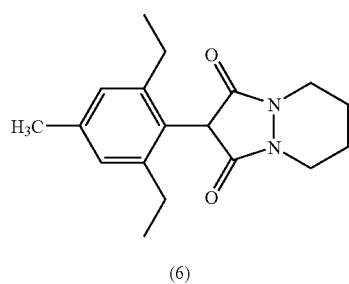

(6)

A catalytic amount of 4-dimethylaminopyridine is added to a solution, cooled to a temperature of 0° C., of 3 g (10.4 mmol) of (6) and 1.6 g (15.8 mmol) of triethylamine in 100 ml of tetrahydrofuran. 1.57 g (13.0 mmol) of pivaloyl chloride is then added dropwise. After stirring for 30 minutes at a temperature of 0° C., the cooling is removed and the stirring is continued for a further 60 minutes. The reaction mixture is then introduced into saturated aqueous sodium chloride solution and the organic phase is separated off. The organic phase is dried over magnesium sulfate, filtered off and concentrated by evaporation. After purification by chromatography and recrystallisation from diethyl ether, 2.94 g of (7) having a melting point of from 135 to 136° C. are obtained.

Example P5

Preparation of 2-(2,6-diethyl-4-methyl-phenyl)-tetrahydro-pyrazolo[1,2-a]pyridazine-1,3-dione 1.39 g of tetrahydro-pyrazolo[1,2-a]pyridazine-1,3-dione and 2.68 g of sodium tertiary butanolate are dissolved at 20° in 20 ml of dimethylformamide, and 3.21 g of 2,6-diethyl-4-methyl-iodobenzene and 0.82 g of $Pd(TPP)_2Cl_2$ are added. Stirring is then carried out for 2.5 hours at 125°. After cooling to room temperature, 200 ml of ethyl acetate and 200 ml of ether are added and the reaction mixture is poured onto a suction filter. 100 ml of water and 100 ml of methylene chloride are added to the filtration residue, and acidification is carried out using hydrochloric acid. The organic phase is separated off, dried and concentrated by evaporation.

The residue (1.9 g) is chromatographed on silica gel (ethyl acetate/hexane 3:1). 2-(2,6-Diethyl-4-methyl-phenyl)-tetrahydro-pyrazolo[1,2-a]pyridazine-1,3-dione is obtained in the form of beige crystals having a melting point of from 174 to 175°.

Example P6

Preparation of 2-(2,6-diethyl-4-methyl-phenyl)-tetrahydropyrazolo[1,2-a]pyridazine-1,3-dione 1.39 g of tetrahydro-pyrazolo[1,2-a]pyridazine-1,3-dione and 2.68 g of sodium tertiary butanolate are dissolved at 20° in 20 ml of dimethylformamide, and 2.66 g of 2,6-diethyl-4-methyl-bromobenzene as well as 0.82 g of $Pd(TPP)_2Cl_2$ are added. Stirring is then carried out for 2.5 hours at 125°. After cooling to room temperature, 200 ml of ethyl acetate and 200 ml of ether are added, and the reaction mixture is poured onto a suction filter. 100 ml of water and 100 ml of methylene chloride are added to the filtration residue and acidification is carried out using hydrochloric acid. The organic phase is separated off, dried and concentrated by evaporation. The residue (1.4 g) is chromatographed on silica gel (ethyl acetate/hexane 3:1).

2-(2,6-Diethyl-4-methyl-phenyl)-tetrahydro-pyrazolo[1,2-a]pyridazine-1,3-dione is obtained in the form of beige crystals having a melting point of from 174 to 175°.

In the following Tables, the melting points are quoted in ° C. Me denotes the methyl group. Where a formula is given for the substituents $G_1$ to $G_{10}$ and $R_4$ and $R_5$ (independently of each other), the left-hand side of that formula is the linking point to the oxygen atom of the heterocycle $Q_1$ to $Q_{10}$. In the case of the substituent meaning of $R_4$ and $R_5$ together, the right-hand side of the molecule is the linking point to the heterocycle $Q_1$. The remaining terminal valencies are methyl groups.

In the following Tables, "LC/MS: M+" expresses in daltons the positively charged molecular ion that has been ascertained from the mass spectrum in the analysis of the product by coupled HPLC (High Performance Liquid Chromatography) and MS (Mass Spectrometry) devices.

TABLE 1
Compounds of formula Ia:
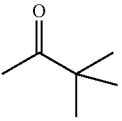
| No. | R$_1$ | R$_3$ | R$_4$/R$_5$ | G$_1$ | Physical data |
|---|---|---|---|---|---|
| 1.1 | ethyl | ethyl | —(CH$_2$)$_4$— | —H | m.p. 209-211 |
| 1.2 | ethyl | ethyl | —(CH$_2$)$_4$— | 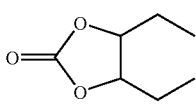 | m.p. 125-127 |
| 1.3 | ethyl | ethyl | 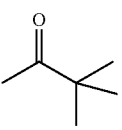 | 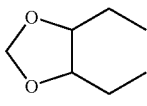 | m.p. 195 |
| 1.4 | ethyl | ethyl | 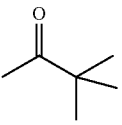 | 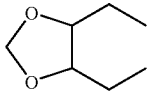 | m.p. 180 |
| 1.5 | ethyl | ethyl | 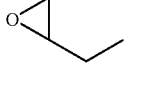 | —H | wax |
| 1.6 | ethyl | ethyl | 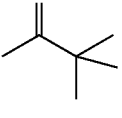 | 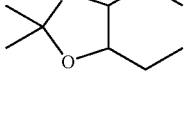 | solid |
| 1.1 | ethyl | ethyl | 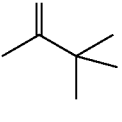 | 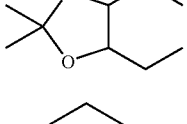 | crystalline |
| 1.2 | ethyl | ethyl | 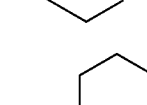 | —H | crystalline |
| 1.3 | ethyl | ethyl | 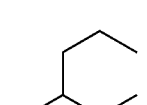 | —H | solid |
| 1.4 | ethyl | ethyl | 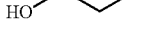 | —H | solid |
| 1.5 | ethyl | ethyl |  | —H | solid |

TABLE 1-continued
Compounds of formula Ia:
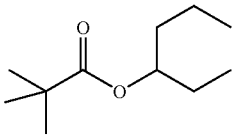
(Ia)
| No. | R₁ | R₃ | R₄/R₅ | G₁ | Physical data |
|---|---|---|---|---|---|
| 1.6 | ethyl | ethyl | 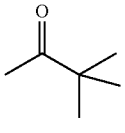 | 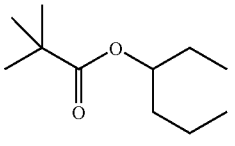 | m.p. 153-155 |
| 1.7 | ethyl | ethyl | 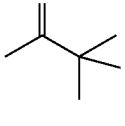 | 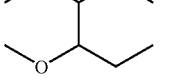 | oil |
| 1.8 | ethyl | ethyl | 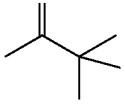 | 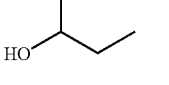 | oil |
| 1.9 | ethyl | ethyl | 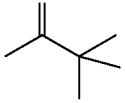 | 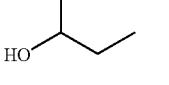 | solid |
| 1.10 | ethyl | ethyl |  | —H | solid |
| 1.11 | ethyl | ethyl | 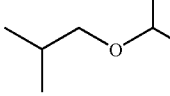 | —H | viscous |
| 1.12 | ethyl | ethyl |  | —H | viscous |
| 1.13 | ethyl | ethyl | 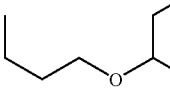 | —H | viscous |
| 1.14 | ethyl | ethyl |  | —H | viscous |
| 1.15 | ethyl | ethyl | 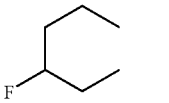 | —H | viscous |

TABLE 1-continued

Compounds of formula Ia:

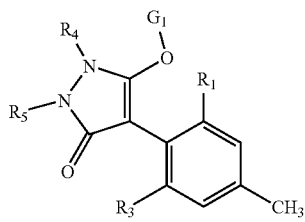

(Ia)

| No. | $R_1$ | $R_3$ | $R_4/R_5$ | $G_1$ | Physical data |
|---|---|---|---|---|---|
| 1.16 | ethyl | ethyl | isobutyl-O-CH(Et)(n-Pr) | C(O)C(CH$_3$)$_3$ | viscous |
| 1.17 | ethyl | ethyl | HO-CH$_2$CH$_2$-O-CH(Et)(n-Pr) | —H | viscous |
| 1.18 | ethyl | ethyl | HOOC-CH(CH$_3$)-O-CH(Et)(n-Pr) | —H | solid |
| 1.19 | ethyl | ethyl | HOOC-CH$_2$-O-CH(Et)(n-Pr) | —H | solid |
| 1.20 | ethyl | ethyl | n-butyl-O-CH(Et)(n-Pr) | C(O)C(CH$_3$)$_3$ | solid |
| 1.21 | ethyl | ethyl | isopropyl-O-CH(Et)(n-Pr) | C(O)C(CH$_3$)$_3$ | oil |
| 1.22 | ethyl | ethyl | MeO-C(O)-CH(CH$_3$)-O-CH(Et)(n-Pr) | C(O)C(CH$_3$)$_3$ | viscous |
| 1.23 | ethyl | ethyl | MeO-C(O)-CH$_2$-O-CH(Et)(n-Pr) | —H | viscous |

TABLE 1-continued
Compounds of formula Ia:
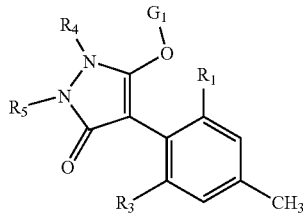
(Ia)
| No. | R₁ | R₃ | R₄/R₅ | G₁ | Physical data |
|---|---|---|---|---|---|
| 1.24 | ethyl | ethyl | | —H | viscous |
| 1.25 | ethyl | ethyl | | | viscous |
| 1.26 | ethyl | ethyl | | —H | viscous |
| 1.27 | ethyl | ethyl | | —H | solid |
| 1.28 | ethyl | ethyl | | | solid |
| 1.29 | ethyl | ethyl | | —H | crystalline |
| 1.30 | ethyl | ethyl | | —H | wax |
| 1.31 | ethyl | ethyl | | | viscous |
| 1.32 | ethyl | ethyl | | | viscous |

TABLE 1-continued

Compounds of formula Ia:

(Ia)

| No. | R$_1$ | R$_3$ | R$_4$/R$_5$ | G$_1$ | Physical data |
|---|---|---|---|---|---|
| 1.33 | ethyl | ethyl | (1-(benzyloxy)propyl)propyl | —H | solid |
| 1.34 | ethyl | ethyl | (1-(benzyloxy)propyl)propyl | pivaloyl | wax |
| 1.35 | ethyl | ethyl | 1-(2-(2-methoxyethoxy)ethoxy)-... with HO | —H | amorphous |
| 1.36 | ethyl | ethyl | 1-(2-(2-methoxyethoxy)ethoxy)propyl | —H | wax |
| 1.37 | ethyl | ethyl | 1-(2-(2-methoxyethoxy)ethoxy)propyl | pivaloyl | oil |
| 1.38 | ethyl | ethyl | 1,2-dimethoxybutyl | —H | crystalline |
| 1.39 | ethyl | ethyl | 1,2-dihydroxybutyl | —H | solid |
| 1.40 | ethyl | ethyl | 1,2-dihydroxybutyl | pivaloyl | solid |

TABLE 1-continued
Compounds of formula Ia:
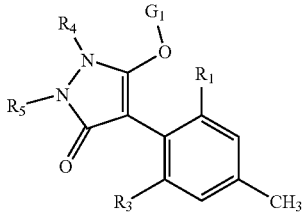
(Ia)
| No. | R₁ | R₃ | R₄/R₅ | G₁ | Physical data |
|---|---|---|---|---|---|
| 1.41 | ethyl | ethyl | 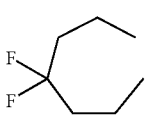 | —H | m.p. 283 |
| 1.42 | ethyl | ethyl | 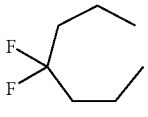 | —H | m.p. 227 |
| 1.43 | ethyl | ethyl | 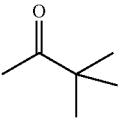 | 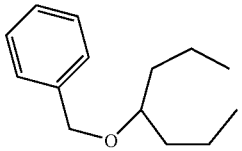 | m.p. 122-124 |
| 1.44 | ethyl | ethyl | 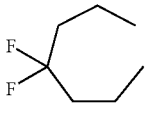 | —H | m.p. 148-151 |
| 1.45 | ethyl | ethynyl | 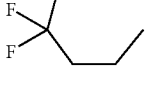 | —H | m.p. 163-166 |
| 1.46 | ethyl | ethynyl | 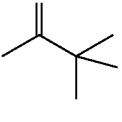 | 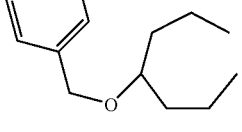 | m.p. 114-116 |
| 1.47 | ethyl | ethyl | 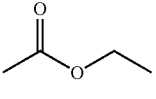 | —H | solid |
| 1.48 | ethyl | ethyl | —(CH₂)₄— | 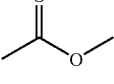 |  |
| 1.49 | ethyl | ethyl | —(CH₂)₄— | 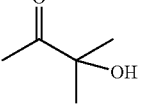 |  |
| 1.50 | ethyl | ethyl | —(CH₂)₄— |  |  |

TABLE 1-continued

Compounds of formula Ia:

(Ia)

| No. | R₁ | R₃ | R₄/R₅ | G₁ | Physical data |
|---|---|---|---|---|---|
| 1.51 | ethyl | ethyl | —(CH₂)₄— | -S(O)₂-ethyl | |
| 1.52 | ethyl | ethyl | —(CH₂)₄— | -S(O)₂-CH₂CH₂Cl | |
| 1.53 | ethyl | ethyl | —(CH₂)₄— | -S(O)₂-CF₃ | |
| 1.54 | ethyl | ethyl | —(CH₂)₄— | -S(O)₂-CH₂-C(=CH₂)-CH₃ | |
| 1.55 | ethyl | ethyl | —(CH₂)₄— | -S(O)₂-CH₂-CH=CH-Cl | |
| 1.56 | ethyl | ethyl | —(CH₂)₄— | -S(O)₂-NH-CH₃ | |
| 1.57 | ethyl | ethyl | —(CH₂)₄— | -S(O)₂-N(Et)₂ | |
| 1.58 | ethyl | ethyl | —(CH₂)₄— | -P(O)(OEt)₂ (methyl on P) | |
| 1.59 | ethyl | ethyl | —(CH₂)₄— | —CH₂—OMe | |
| 1.60 | ethyl | ethyl | —(CH₂)₄— | —CH₂—SMe | |
| 1.61 | ethyl | ethyl | —(CH₂)₄— | -C(O)-N(Et)₂ | |
| 1.62 | ethyl | ethyl | —(CH₂)₄— | -C(O)-C(CH₃)₂-cyclopentyl | |

TABLE 1-continued
Compounds of formula Ia:
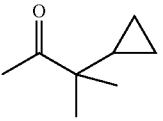
(Ia)
| No. | R₁ | R₃ | R₄/R₅ | G₁ | Physical data |
|---|---|---|---|---|---|
| 1.63 | ethyl | ethyl | —(CH₂)₄— | 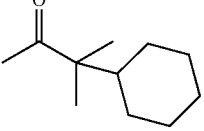 | |
| 1.64 | ethyl | ethyl | —(CH₂)₄— | 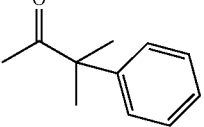 | |
| 1.65 | ethyl | ethyl | —(CH₂)₄— | 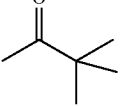 | |
| 1.66 | MeO— | ethyl | —(CH₂)₄— | 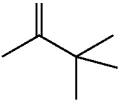 | m.p. 143-144° C. |
| 1.67 | ethyl— | ethynyl | —(CH₂)₄— | 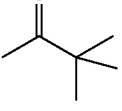 | |
| 1.68 | —OCHF₂ | ethyl | —(CH₂)₄— | 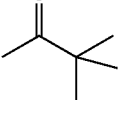 | |
| 1.69 | —CHO | ethyl | —(CH₂)₄— |  | |
| 1.70 | 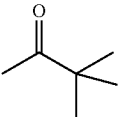 | ethyl | —(CH₂)₄— |  | |
| 1.71 | 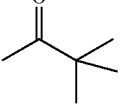 | ethyl | —(CH₂)₄— | | |

TABLE 1-continued

Compounds of formula Ia:

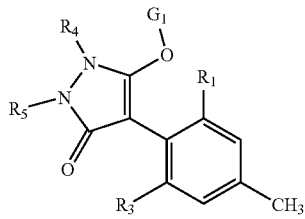

(Ia)

| No. | $R_1$ | $R_3$ | $R_4/R_5$ | $G_1$ | Physical data |
|---|---|---|---|---|---|
| 1.72 | MeO— | MeO- | —(CH$_2$)$_4$— | (pivaloyl) | |
| 1.73 | MeO— | ethyl | —(CH$_2$)$_4$— | —H | m.p. 159-161° C. |
| 1.74 | ethyl— | ethynyl | —(CH$_2$)$_4$— | —H | |
| 1.75 | —OCHF$_2$ | ethyl | —(CH$_2$)$_4$— | —H | |
| 1.76 | —CHO | ethyl | —(CH$_2$)$_4$— | —H | |
| 1.77 | (acetyl) | ethyl | —(CH$_2$)$_4$— | —H | |
| 1.78 | OH | ethyl | —(CH$_2$)$_4$— | —H | |
| 1.79 | MeO— | MeO— | —(CH$_2$)$_4$— | —H | |
| 1.80 | MeO— | ethyl | —(CH$_2$)$_4$— | CO$_2$C$_2$H$_5$ | m.p. 112-113° C. |
| 1.81 | ethyl | ethyl | (norbornyl) | —H | m.p. 283° C. (decomposition) |
| 1.82 | ethyl | ethyl | (diethyl dioxolanone) | —H | m.p. 140° C. |
| 1.83 | MeO— | ethyl | (methoxyethoxy hexyl) | —H | solid |
| 1.84 | MeO— | ethyl | (methoxyethoxy hexyl) | (pivaloyl) | wax |
| 1.85 | MeO— | ethyl | (hydroxyhexyl) | —H | m.p. 177-180° C. |
| 1.86 | MeO— | ethyl | (difluorocycloheptyl) | —H | m.p. 208-210° C. |
| 1.87 | MeO— | ethyl | (difluorocycloheptyl) | (pivaloyl) | m.p. 102-104° C. |

TABLE 1-continued
Compounds of formula Ia:
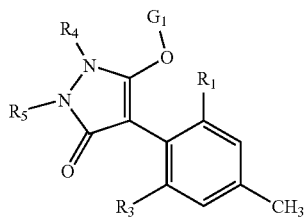
(Ia)
| No. | R₁ | R₃ | R₄/R₅ | G₁ | Physical data |
|---|---|---|---|---|---|
| 1.88 | ethyl | ethyl | (trans) | —H | m.p. 193-194° C. |
| 1.89 | ethyl | ethyl | (trans) | | m.p. 163-165° C. |
| 1.90 | ethyl | ethyl | (trans) | | solid |
| 1.91 | ethyl | ethyl | | —H | wax |
| 1.92 | ethyl | ethyl | | | wax |
| 1.93 | ethyl | ethyl | | —H | wax |
| 1.94 | ethyl | ethyl | | | wax |

TABLE 1-continued
Compounds of formula Ia:
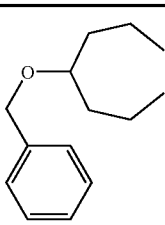
| No. | $R_1$ | $R_3$ | $R_4/R_5$ | $G_1$ | Physical data |
|---|---|---|---|---|---|
| 1.95 | ethyl | ethyl | 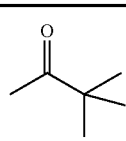 | 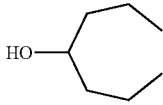 | viscous |
| 1.96 | ethyl | ethyl | 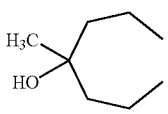 | —H | m.p. 200-202° C. |
| 1.97 | ethyl | ethyl | 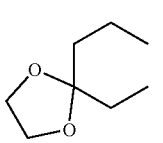 | —H | m.p. 210-220° C. (decomposition) |
| 1.98 | ethyl | ethyl | 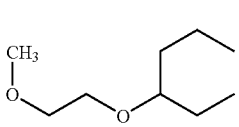 | —H | solid |
| 1.99 | ethyl | ethynyl | 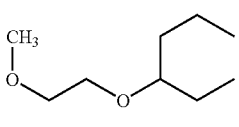 | —H | wax |
| 1.100 | ethyl | ethynyl | 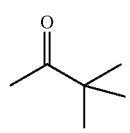 | 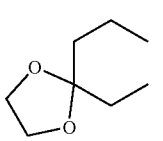 | wax |
| 1.101 | ethyl | ethyl | 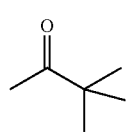 | 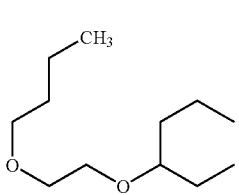 | viscous |
| 1.102 | ethyl | ethyl |  | —H | wax |

TABLE 1-continued

Compounds of formula Ia:

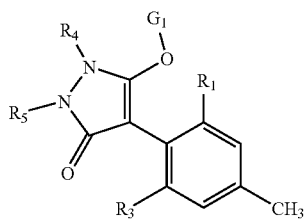

(Ia)

| No. | R$_1$ | R$_3$ | R$_4$/R$_5$ | G$_1$ | Physical data |
|---|---|---|---|---|---|
| 1.103 | OCH$_3$ | ethyl | CH$_3$OCH$_2$CH$_2$O-CH(Et)(Pr) | C(O)N(Et)$_2$ | wax |
| 1.104 | ethyl | ethyl | CH$_3$OCH$_2$CH$_2$O-CH(Et)(Pr) | C(O)N(Et)$_2$ | wax |
| 1.105 | ethyl | ethyl | CH$_3$(CH$_2$)$_3$OCH$_2$CH$_2$O-CH(Et)(Pr) | C(O)C(CH$_3$)$_3$ | wax |
| 1.106 | ethyl | ethyl | CH$_3$(CH$_2$)$_3$OCH$_2$CH$_2$O-CH(Et)(Pr) | S(O)$_2$CH(Me)$_2$ | wax |
| 1.107 | ethyl | ethyl | CH$_3$(CH$_2$)$_3$OCH$_2$CH$_2$O-CH(Et)(Pr) | S(O)$_2$CH$_2$CH$_2$CH$_2$Cl | wax |
| 1.108 | ethyl | ethyl | CH$_3$(CH$_2$)$_3$OCH$_2$CH$_2$O-CH(Et)(Pr) | S(O)$_2$CH=CH$_2$ | wax |
| 1.109 | ethyl | ethyl | CH$_3$(CH$_2$)$_3$OCH$_2$CH$_2$O-CH(Et)(Pr) | S(O)$_2$CH$_2$C(CH$_3$)=CH$_2$ | wax |

TABLE 1-continued
Compounds of formula Ia:
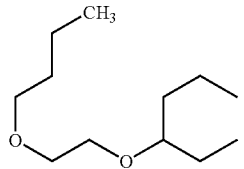
(Ia)
| No. | R₁ | R₃ | R₄/R₅ | G₁ | Physical data |
|---|---|---|---|---|---|
| 1.110 | ethyl | ethyl | 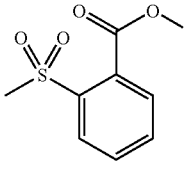 | 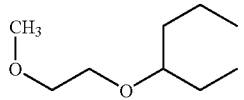 | wax |
| 1.111 | ethynyl | ethyl | 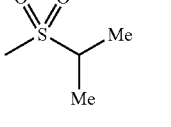 | 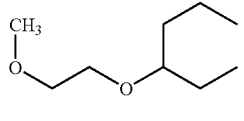 | wax |
| 1.112 | ethynyl | ethyl | 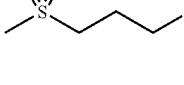 | 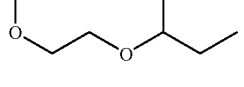 | wax |
| 1.113 | ethynyl | ethyl | 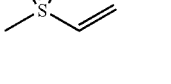 | 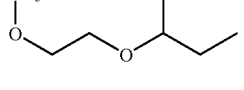 | wax |
| 1.114 | ethynyl | ethyl | 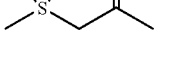 | 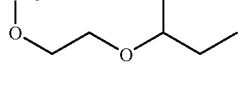 | wax |
| 1.115 | ethynyl | ethyl | 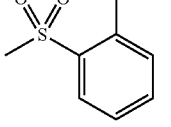 | 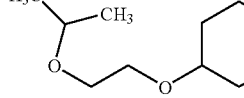 | wax |
| 1.116 | ethyl | ethyl | 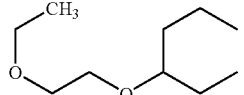 | —H | wax |
| 1.117 | ethyl | ethyl | 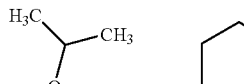 | —H | wax |
| 1.118 | ethyl | ethynyl | 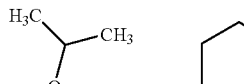 | —H | wax |

TABLE 1-continued

Compounds of formula Ia:

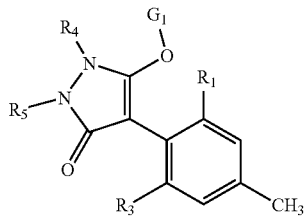

(Ia)

| No. | R$_1$ | R$_3$ | R$_4$/R$_5$ | G$_1$ | Physical data |
|---|---|---|---|---|---|
| 1.119 | ethyl | ethynyl | [CH₃CH₂-O-CH₂CH₂-O-CH(Et)(Pr)] | —H | wax |
| 1.120 | OCH$_3$ | ethyl | [PhCH₂-O-CH(Pr)(Pr)] | —H | m.p. 130-136° C. |
| 1.121 | OCH$_3$ | ethyl | [HO-CH(Pr)(Pr)] | —H | m.p. 198-200° C. |
| 1.122 | ethyl | ethyl | [CH₃O-CH₂CH₂-O-CH(Et)(Pr)] | [CH₃C(O)-N(CH₃)-CH₂Ph] | wax |
| 1.123 | ethyl | OCH$_3$ | [CH₃O-CH₂CH₂-O-CH(Et)(Pr)] | [CH₃C(O)-N(CH₃)-CH₂Ph] | wax |
| 1.124 | ethynyl | ethyl | [CH₃CH₂-O-CH₂CH₂-O-CH(Et)(Pr)] | [(CH₃)₃C-C(O)-] | wax |
| 1.125 | ethynyl | ethyl | [CH₃CH₂-O-CH₂CH₂-O-CH(Et)(Pr)] | [CH₃-SO₂-CH=CH₂] | wax |

TABLE 1-continued

Compounds of formula Ia:

(Ia)

| No. | R₁ | R₃ | R₄/R₅ | G₁ | Physical data |
|---|---|---|---|---|---|
| 1.126 | ethynyl | ethyl | CH₃CH₂-O-CH₂CH₂-O-CH(C₂H₅)(C₃H₇) | -C(=O)-S-n-C₈H₁₇ | wax |
| 1.127 | ethyl | ethyl | 3-pentanone-yl | —H | |
| 1.128 | ethyl | ethyl | CH₃-(CH₂)₃-O-CH₂CH₂-O-CH(C₂H₅)(C₃H₇) | -SO₂-CH₂-(2,4,6-trimethylphenyl) | |
| 1.129 | OCH₃ | ethyl | CH₃-O-CH₂CH₂-O-CH(C₂H₅)(C₃H₇) | -SO₂-(2,6-difluorophenyl) | wax (LC/MS: M⁺ = 552) |
| 1.130 | OCH₃ | ethyl | CH₃-O-CH₂CH₂-O-CH(C₂H₅)(C₃H₇) | -SO₂-(2,4-dichlorothien-3-yl) | wax (LC/MS: M⁺ = 590) |
| 1.131 | OCH₃ | ethyl | CH₃-O-CH₂CH₂-O-CH(C₂H₅)(C₃H₇) | -SO₂-(3,5-dimethylisoxazol-4-yl) | wax (LC/MS: M⁺ = 535) |
| 1.132 | OCH₃ | ethyl | CH₃-O-CH₂CH₂-O-CH(C₂H₅)(C₃H₇) | -SO₂-(4-methoxyphenyl) | wax (LC/MS: M⁺ = 546) |

TABLE 1-continued
Compounds of formula Ia:
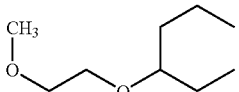
(Ia)
| No. | $R_1$ | $R_3$ | $R_4/R_5$ | $G_1$ | Physical data |
|---|---|---|---|---|---|
| 1.133 | OCH$_3$ | ethyl | 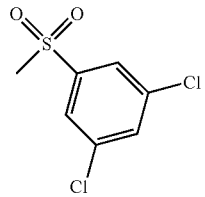 | 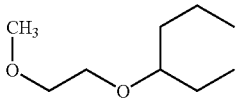 | wax (LC/MS: M$^+$ = 584) |
| 1.134 | OCH$_3$ | ethyl | 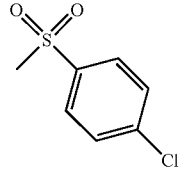 | 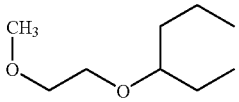 | wax (LC/MS: M$^+$ = 550) |
| 1.135 | OCH$_3$ | ethyl | 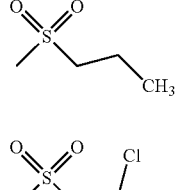 | 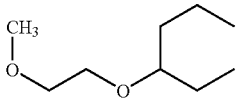 | wax (LC/MS: M$^+$ = 482) |
| 1.136 | OCH$_3$ | ethyl | 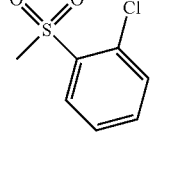 | 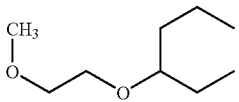 | wax (LC/MS: M$^+$ = 550) |
| 1.137 | OCH$_3$ | ethyl | 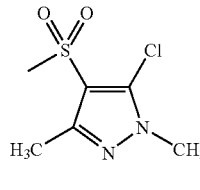 |  | wax (LC/MS: M$^+$ = 568) |
| 1.138 | OCH$_3$ | ethyl | 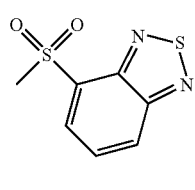 | 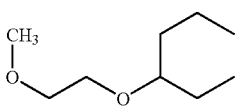 | wax (LC/MS: M$^+$ = 574) |
| 1.139 | OCH$_3$ | ethyl | | 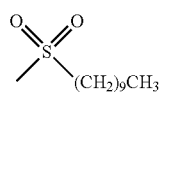 | wax (LC/MS: M$^+$ = 580) |

TABLE 1-continued

Compounds of formula Ia:

(Ia)

| No. | R₁ | R₃ | R₄/R₅ | G₁ | Physical data |
|---|---|---|---|---|---|
| 1.140 | OCH₃ | ethyl | CH₃–O–CH₂CH₂–O–CH(CH₂CH₃)(CH₂CH₂CH₃) | –S(O)₂–(2,4-difluorophenyl) | wax (LC/MS: M⁺ = 552) |
| 1.141 | OCH₃ | ethyl | CH₃–O–CH₂CH₂–O–CH(CH₂CH₃)(CH₂CH₂CH₃) | –S(O)₂–(3-chlorophenyl) | wax (LC/MS: M⁺ = 550) |
| 1.142 | OCH₃ | ethyl | CH₃–O–CH₂CH₂–O–CH(CH₂CH₃)(CH₂CH₂CH₃) | –S(O)₂–(2-nitrophenyl) | wax (LC/MS: M⁺ = 561) |
| 1.143 | OCH₃ | ethyl | CH₃–O–CH₂CH₂–O–CH(CH₂CH₃)(CH₂CH₂CH₃) | –S(O)₂–(1-methylimidazol-4-yl) | wax (LC/MS: M⁺ = 520) |
| 1.144 | OCH₃ | ethyl | CH₃–O–CH₂CH₂–O–CH(CH₂CH₃)(CH₂CH₂CH₃) | —S(O)₂CH₃ | wax (LC/MS: M⁺ = 454) |
| 1.145 | OCH₃ | ethyl | CH₃–O–CH₂CH₂–O–CH(CH₂CH₃)(CH₂CH₂CH₃) | –S(O)₂–phenyl | wax (LC/MS: M⁺ = 516) |
| 1.146 | OCH₃ | ethyl | CH₃–O–CH₂CH₂–O–CH(CH₂CH₃)(CH₂CH₂CH₃) | –S(O)₂–(3-trifluoromethylphenyl) | wax (LC/MS: M⁺ = 584) |

TABLE 1-continued

Compounds of formula Ia:

(Ia)

| No. | R₁ | R₃ | R₄/R₅ | G₁ | Physical data |
|---|---|---|---|---|---|
| 1.147 | OCH₃ | ethyl | CH₃-O-CH₂-CH₂-O-CH(CH₂CH₃)(CH₂CH₂CH₃) | -S(O)₂-CH₂CH₃ | wax (LCIMS: M⁺ = 468) |
| 1.148 | OCH₃ | ethyl | CH₃-O-CH₂-CH₂-O-CH(CH₂CH₃)(CH₂CH₂CH₃) | -S(O)₂-CH₂CH₂CH₂CH₃ | wax (LC/MS: M⁺ = 496) |
| 1.149 | OCH₃ | ethyl | CH₃-O-CH₂-CH₂-O-CH(CH₂CH₃)(CH₂CH₂CH₃) | -S(O)₂-(CH₂)₇CH₃ | wax (LC/MS: M⁺ = 552) |
| 1.150 | OCH₃ | ethyl | CH₃-O-CH₂-CH₂-O-CH(CH₂CH₃)(CH₂CH₂CH₃) | 2-cyanophenyl-S(O)₂- | wax (LC/MS: M⁺ = 541) |
| 1.151 | ethyl | ethyl | PhCH₂-O-CH(CH₂CH₃)(CH₂CH₂CH₃) | 2,6-difluorophenyl-S(O)₂- | wax (LC/MS: M⁺ = 582) |
| 1.152 | ethyl | ethyl | PhCH₂-O-CH(CH₂CH₃)(CH₂CH₂CH₃) | 2,4-dichlorothien-3-yl-S(O)₂- | wax (LC/MS: M⁺ = 620) |
| 1.153 | ethyl | ethyl | PhCH₂-O-CH(CH₂CH₃)(CH₂CH₂CH₃) | 3,5-dimethylisoxazol-4-yl-S(O)₂- | wax (LC/MS: M⁺ = 565) |

TABLE 1-continued

Compounds of formula Ia:

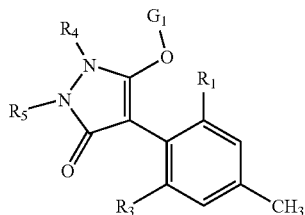

(Ia)

| No. | R₁ | R₃ | R₄/R₅ | G₁ | Physical data |
|---|---|---|---|---|---|
| 1.154 | ethyl | ethyl | (1-ethylpropoxy)methylbenzene | 4-methoxyphenyl methyl sulfone | wax (LC/MS: M⁺ = 576) |
| 1.155 | ethyl | ethyl | (1-ethylpropoxy)methylbenzene | 3,5-dichlorophenyl methyl sulfone | wax (LC/MS: M⁺ = 614) |
| 1.156 | ethyl | ethyl | (1-ethylpropoxy)methylbenzene | 4-chlorophenyl methyl sulfone | wax (LC/MS: M⁺ = 580) |
| 1.157 | ethyl | ethyl | (1-ethylpropoxy)methylbenzene | methyl propyl sulfone | wax (LC/MS: M⁺ = 512) |
| 1.158 | ethyl | ethyl | (1-ethylpropoxy)methylbenzene | 2-chlorophenyl methyl sulfone | wax (LC/MS: M⁺ = 580) |

TABLE 1-continued
Compounds of formula Ia:
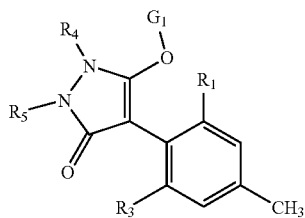
(Ia)
| No. | R₁ | R₃ | R₄/R₅ | G₁ | Physical data |
|---|---|---|---|---|---|
| 1.159 | ethyl | ethyl | | | wax (LC/MS: M⁺ = 642) |
| 1.160 | ethyl | ethyl | | | wax (LC/MS: M⁺ = 598) |
| 1.161 | ethyl | ethyl | | | wax (LC/MS: M⁺ = 604) |
| 1.162 | ethyl | ethyl | | | wax (LC/MS: M⁺ = 546) |
| 1.163 | ethyl | ethyl | | | wax (LC/MS: M⁺ = 582) |

TABLE 1-continued

Compounds of formula Ia:

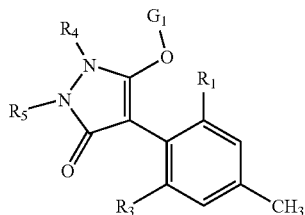

(Ia)

| No. | R₁ | R₃ | R₄/R₅ | G₁ | Physical data |
|---|---|---|---|---|---|
| 1.164 | ethyl | ethyl | [1-(benzyloxy)propyl]ethyl | 3-chlorophenyl methylsulfonyl | wax (LC/MS: M⁺ = 580) |
| 1.165 | ethyl | ethyl | [1-(benzyloxy)propyl]ethyl | 2-nitrophenyl methylsulfonyl | wax (LC/MS: M⁺ = 591) |
| 1.166 | ethyl | ethyl | [1-(benzyloxy)propyl]ethyl | 1-methyl-4-(methylsulfonyl)imidazolyl | wax (LC/MS: M⁺ = 550) |
| 1.167 | ethyl | ethyl | [1-(benzyloxy)propyl]ethyl | —S(O)₂CH₃ | wax (LC/MS: M⁺ = 484) |
| 1.168 | ethyl | ethyl | [1-(benzyloxy)propyl]ethyl | phenyl methylsulfonyl | wax (LC/MS: M⁺ = 546) |

TABLE 1-continued

Compounds of formula Ia:

(Ia)

| No. | R₁ | R₃ | R₄/R₅ | G₁ | Physical data |
|---|---|---|---|---|---|
| 1.169 | ethyl | ethyl | 3-(benzyloxy)pentyl | 3-(methylsulfonyl)-(trifluoromethyl)phenyl | wax (LC/MS: M⁺ = 614) |
| 1.170 | ethyl | ethyl | 3-(benzyloxy)pentyl | isopropylsulfonylmethyl | wax (LC/MS: M⁺ = 512) |
| 1.171 | ethyl | ethyl | 3-(benzyloxy)pentyl | ethylsulfonylmethyl | wax (LC/MS: M⁺ = 498) |
| 1.172 | ethyl | ethyl | 3-(benzyloxy)pentyl | propylsulfonylmethyl | wax (LC/MS: M⁺ = 526) |
| 1.173 | ethyl | ethyl | 3-(benzyloxy)pentyl | octylsulfonylmethyl | wax (LC/MS: M⁺ = 582) |

TABLE 1-continued

Compounds of formula Ia:

(Ia)

| No. | R₁ | R₃ | R₄/R₅ | G₁ | Physical data |
|---|---|---|---|---|---|
| 1.174 | ethyl | ethyl | 1-ethylbutyl benzyl ether | 2-(methylsulfonyl)benzonitrile | wax (LC/MS: M⁺ = 571) |
| 1.175 | ethyl | ethyl | 2-methoxyethoxy-pentyl | 2,6-difluoro-methylsulfonylphenyl | wax (LC/MS: M⁺ = 550) |
| 1.176 | ethyl | ethyl | 2-methoxyethoxy-pentyl | 2,4-dichloro-3-methylsulfonylthiophene | wax (LC/MS: M⁺ = 588) |
| 1.177 | ethyl | ethyl | 2-methoxyethoxy-pentyl | 3,5-dimethyl-4-methylsulfonylisoxazole | wax (LC/MS: M⁺ = 533) |
| 1.178 | ethyl | ethyl | 2-methoxyethoxy-pentyl | 4-methoxy-methylsulfonylphenyl | wax (LC/MS: M⁺ = 544) |
| 1.179 | ethyl | ethyl | 2-methoxyethoxy-pentyl | 3,5-dichloro-methylsulfonylphenyl | wax (LC/MS: M⁺ = 582) |

TABLE 1-continued

Compounds of formula Ia:

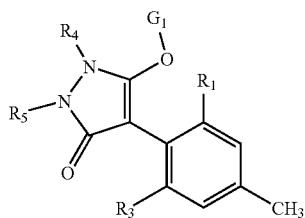

(Ia)

| No. | R₁ | R₃ | R₄/R₅ | G₁ | Physical data |
|---|---|---|---|---|---|
| 1.180 | ethyl | ethyl | CH₃O-CH₂-CH₂-O-CH(CH₂CH₃)(CH₂CH₂CH₃) | 4-Cl-C₆H₄-SO₂- | wax (LC/MS: M⁺ = 548) |
| 1.181 | ethyl | ethyl | CH₃O-CH₂-CH₂-O-CH(CH₂CH₃)(CH₂CH₂CH₃) | CH₃-SO₂-CH₂-CH₂-CH₃ | wax (LC/MS: M⁺ = 480) |
| 1.182 | ethyl | ethyl | CH₃O-CH₂-CH₂-O-CH(CH₂CH₃)(CH₂CH₂CH₃) | 2-Cl-C₆H₄-SO₂- | wax (LC/MS: M⁺ = 548) |
| 1.183 | ethyl | ethyl | CH₃O-CH₂-CH₂-O-CH(CH₂CH₃)(CH₂CH₂CH₃) | 5-chloro-1,3-dimethyl-1H-pyrazol-4-yl-SO₂- | wax (LC/MS: M⁺ = 566) |
| 1.184 | ethyl | ethyl | CH₃O-CH₂-CH₂-O-CH(CH₂CH₃)(CH₂CH₂CH₃) | 2,1,3-benzothiadiazol-4-yl-SO₂- | wax (LC/MS: M⁺ = 572) |
| 1.185 | ethyl | ethyl | CH₃O-CH₂-CH₂-O-CH(CH₂CH₃)(CH₂CH₂CH₃) | CH₃-SO₂-CH₂-CH₂-CH₂-Cl | wax (LC/MS: M⁺ = 514) |
| 1.186 | ethyl | ethyl | CH₃O-CH₂-CH₂-O-CH(CH₂CH₃)(CH₂CH₂CH₃) | 2,4-diF-C₆H₃-SO₂- | wax (LC/MS: M⁺ = 550) |

TABLE 1-continued
Compounds of formula Ia:
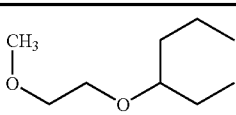
(Ia)
| No. | R₁ | R₃ | R₄/R₅ | G₁ | Physical data |
|---|---|---|---|---|---|
| 1.187 | ethyl | ethyl | 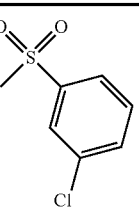 | 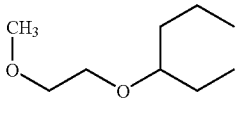 | wax (LC/MS: M⁺ = 548) |
| 1.188 | ethyl | ethyl | 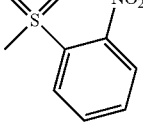 | 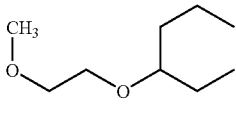 | wax (LC/MS: M⁺ = 559) |
| 1.189 | ethyl | ethyl | 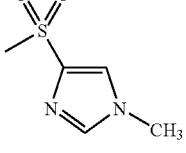 | 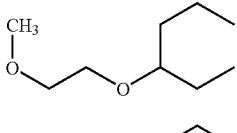 | wax (LC/MS: M⁺ = 518) |
| 1.190 | ethyl | ethyl | 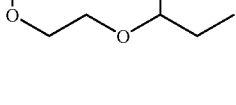 | —S(O)₂CH₃ | wax (LC/MS: M⁺ = 452) |
| 1.191 | ethyl | ethyl | 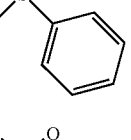 | 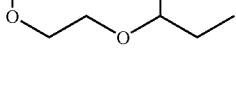 | wax (LC/MS: M⁺ = 514) |
| 1.192 | ethyl | ethyl | 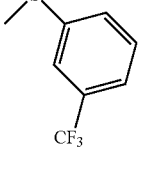 | 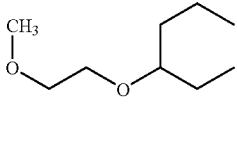 | wax (LC/MS: M⁺ = 582) |
| 1.193 | ethyl | ethyl | 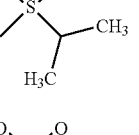 | 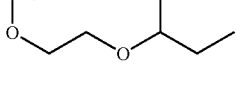 | wax (LC/MS: M⁺ = 480) |
| 1.194 | ethyl | ethyl | 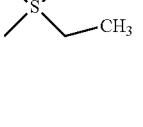 | | wax (LC/MS: M⁺ = 466) |

TABLE 1-continued

Compounds of formula Ia:

(Ia)

| No. | R₁ | R₃ | R₄/R₅ | G₁ | Physical data |
|---|---|---|---|---|---|
| 1.195 | ethyl | ethyl | CH₃O-CH₂CH₂-O-CH(C₂H₅)(C₃H₇) | -S(O)₂-CH₂CH₂CH₂-CH₃ | wax (LC/MS: M⁺ = 494) |
| 1.196 | ethyl | ethyl | CH₃O-CH₂CH₂-O-CH(C₂H₅)(C₃H₇) | -S(O)₂-(CH₂)₇CH₃ | wax (LC/MS: M⁺ = 550) |
| 1.197 | ethyl | ethyl | CH₃O-CH₂CH₂-O-CH(C₂H₅)(C₃H₇) | -S(O)₂-(2-CN-phenyl) | wax (LC/MS: M⁺ = 539) |
| 1.198 | ethyl | ethyl | CH₃O-CH₂CH₂-O-CH(C₂H₅)(C₃H₇) | -S(O)₂-(2-CO₂CH₃-phenyl) | wax (LC/MS: M⁺ = 572) |
| 1.199 | OCH₃ | OCH₃ | -(CH₂)₄- | -H | m.p. 180-193° C. |
| 1.200 | ethyl | ethyl | cyclohexenyl | -CO₂C₂H₅ | m.p. 153-154° C. |

TABLE 2

Compounds of formula Ia:

(Ia)

| No. | R₁ | R₃ | R₄ | R₅ | G₁ | Physical data |
|---|---|---|---|---|---|---|
| 2.01 | ethyl | ethyl | methyl | -CH₂CH₂CH₂-OH | -H | wax |
| 2.02 | ethyl | ethyl | methyl | -CH₂CH₂CH₂-O-CH₃ | -H | solid |

TABLE 2-continued

Compounds of formula Ia:

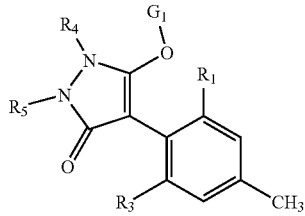

(Ia)

| No. | $R_1$ | $R_3$ | $R_4$ | $R_5$ | $G_1$ | Physical data |
|---|---|---|---|---|---|---|
| 2.03 | ethyl | ethyl | methyl | propyl-O-CH₂-CH₂-O-CH₃ | —H | solid |
| 2.04 | ethyl | ethyl | methyl | propyl-O-methyl | C(=O)C(CH₃)₃ | wax |
| 2.05 | ethyl | ethyl | methyl | propyl-O-CH₂-CH₂-O-CH₃ | C(=O)C(CH₃)₃ | wax |
| 2.06 | ethyl | ethyl | propyl-O-methyl | propyl-O-methyl | —H | m.p. 171-172 |
| 2.07 | ethyl | ethyl | propyl-O-CH₂-CH₂-O-CH₃ | propyl-O-CH₂-CH₂-O-CH₃ | C(=O)C(CH₃)₃ | wax |
| 2.08 | ethyl | ethyl | propyl-O-CH₂-CH₂-O-CH₃ | propyl-O-CH₂-CH₂-O-CH₃ | —H | amorphous |
| 2.09 | ethyl | ethyl | propyl-O-methyl | propyl-O-methyl | C(=O)C(CH₃)₃ | amorphous |
| 2.10 | ethyl | ethyl | propyl-OH | propyl-OH | —H | |
| 2.11 | ethyl | ethyl | methyl | methyl | C(=O)C(CH₃)₃ | |
| 2.12 | ethyl | ethyl | methyl | methyl | —SO₂CH₃ | |
| 2.13 | ethyl | MeO— | methyl | methyl | C(=O)C(CH₃)₃ | |

TABLE 2-continued

Compounds of formula Ia:

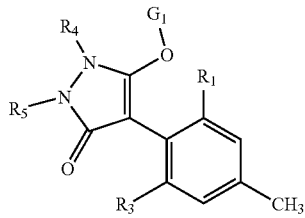

(Ia)

| No. | R$_1$ | R$_3$ | R$_4$ | R$_5$ | G$_1$ | Physical data |
|---|---|---|---|---|---|---|
| 2.14 | ethyl | ethynyl | methyl | methyl | pivaloyl | |
| 2.15 | ethyl | ethyl | methyl | —phenyl | pivaloyl | |
| 2.16 | ethyl | ethyl | methyl | —3-pyridyl | pivaloyl | |
| 2.17 | ethyl | ethyl | methyl | —2-thienyl | pivaloyl | |
| 2.18 | ethyl | ethyl | methyl | —allyl | pivaloyl | |
| 2.19 | ethyl | ethyl | methyl | —crotyl | pivaloyl | |
| 2.20 | ethyl | ethyl | methyl | —4-chloro-phenyl | pivaloyl | |
| 2.21 | MeO— | MeO— | methyl | allyl | —H | |
| 2.22 | ethynyl | ethyl | phenyl— | phenyl | —H | |
| 2.23 | ethynyl | ethyl | phenyl | —CH$_2$CH$_2$CH$_2$Cl | —H | |
| 2.24 | ethyl | ethyl | —CH$_2$CH$_2$SCH$_3$ | methyl— | —H | |
| 2.25 | ethyl | ethyl | —CH$_2$CH$_2$S(O)$_2$CH$_3$ | methyl— | —H | |

TABLE 2-continued

Compounds of formula Ia:

(Ia)

| No. | R$_1$ | R$_3$ | R$_4$ | R$_5$ | G$_1$ | Physical data |
|---|---|---|---|---|---|---|
| 2.26 | ethyl | ethyl | phenyl | (propyl-NH-C(=O)-O-methyl) | —H | |
| 2.27 | ethyl | ethyl | (ethoxy-phenyl) | methyl— | —H | |
| 2.28 | ethyl | ethyl | —benzyl | methyl— | —H | |
| 2.29 | ethyl | ethyl | (propyl-C(=O)-O-methyl) | methyl— | —H | |
| 2.30 | ethyl | ethyl | (propyl-N(methyl)$_2$) | methyl— | —H | |
| 2.31 | ethyl | ethyl | (propyl-phenyl) | methyl— | —H | |
| 2.32 | ethyl | ethyl | —(CH$_2$)$_2$OH | allyl | —H | m.p. 180-185° C. (decomp.) |

TABLE 3

Compounds of formula Ib:

(Ib)

| No. | R$_1$ | R$_3$ | R$_6$ | R$_7$ | R$_8$ | G$_2$ | Physical data |
|---|---|---|---|---|---|---|---|
| 3.01 | ethyl | ethyl | —Me | —Me | —Me | —H | m.p. 249-254° C. |
| 3.02 | ethyl | ethyl | —Me | —H | —Me | —H | |
| 3.03 | ethyl | ethyl | —CH$_2$—CH$_2$—O—CH$_2$—CH$_2$— | | —Me | —H | |
| 3.04 | ethynyl | ethyl | —CH$_2$—CH$_2$— | | —allyl | —H | |
| 3.05 | ethyl | ethyl | —CH$_2$—C(Cl)$_2$— | | —Me | (pivaloyl) | |

TABLE 3-continued

Compounds of formula Ib:

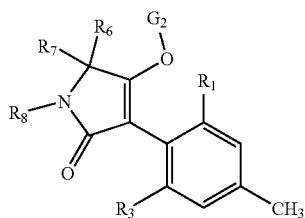

(Ib)

| No. | $R_1$ | $R_8$ | $R_6$ | $R_7$ | $R_3$ | $G_2$ | m.p. |
|---|---|---|---|---|---|---|---|
| 3.06 | ethyl | ethyl | —(CH$_2$)$_2$— | | —Me | —H | |
| 3.07 | ethyl | ethyl | —(CH$_2$)$_2$—CH(CH$_3$)—(CH$_2$)$_2$— | | —Me | —H | |
| 3.08 | ethyl | ethyl | —(CH$_2$)$_2$—C(CH$_3$)$_2$—(CH$_2$)$_2$— | | —Me | —H | |
| 3.09 | ethynyl | ethyl | —(CH$_2$)$_4$— | | —Me | —H | |
| 3.10 | MeO— | ethyl | —(CH$_2$)$_2$— | | —H | —H | |
| 3.11 | MeO— | ethyl | —(CH$_2$)$_2$— | | —methyl | –C(O)C(CH$_3$)$_3$ | |
| 3.12 | —C(O)CH$_3$ | ethyl | —(CH$_2$)$_2$— | | methyl | —H | |
| 3.13 | —OCHF$_2$ | ethyl | —(CH$_2$)$_2$— | | methyl | –C(O)C(CH$_3$)$_3$ | |
| 3.14 | ethyl | ethyl | —(CH$_2$)$_3$— | | methyl | –C(O)C(CH$_3$)$_3$ | |
| 3.15 | ethyl | ethyl | —(CH$_2$)$_5$— | | —H | —H | m.p. 222-224° C. |
| 3.16 | ethyl | ethyl | —(CH$_2$)$_5$— | | —H | –C(O)C(CH$_3$)$_3$ | m.p. 147-149° C |
| 3.17 | ethyl | ethyl | methyl | methyl | —H | —H | m.p. 244-246° C. |
| 3.18 | ethyl | ethyl | methyl | methyl | —H | –C(O)C(CH$_3$)$_3$ | m.p. 164-166° C. |
| 3.19 | ethyl | ethyl | —(CH$_2$)$_5$— | | —n-C$_4$H$_9$ | —H | m.p. 170-175° C. |
| 3.20 | ethyl | ethyl | —(CH$_2$)$_5$— | | —n-C$_4$H$_9$ | –C(O)C(CH$_3$)$_3$ | m.p. 99-101° C. |
| 3.21 | ethyl | ethyl | —(CH$_2$)$_5$— | | C$_3$H$_6$OMe | —H | solid |
| 3.22 | ethyl | ethyl | methyl | methyl | methyl | –C(O)C(CH$_3$)$_3$ | m.p. 94-101° C. |
| 3.23 | ethyl | ethyl | —(CH$_2$)$_5$— | | methyl | —H | m.p. 252-262° C. |

TABLE 3-continued
Compounds of formula Ib:
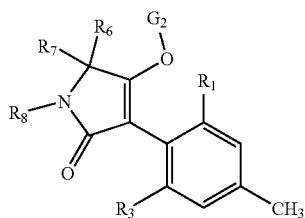
(Ib)
| | | | | | |
|---|---|---|---|---|---|
| 3.24 | ethyl | ethyl | —(CH₂)₅— | methyl | 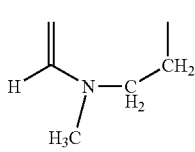 | m.p. 127—128° C. |
| 3.25 | ethyl | ethyl | 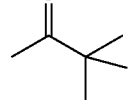 | —H | | crystalline |
| 3.26 | ethyl | ethyl | 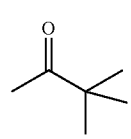 | | 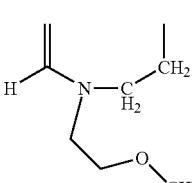 | wax |
| 3.27 | ethyl | ethyl | 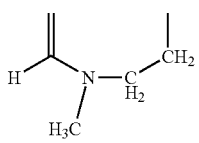 | —H | | crystalline |
| 3.28 | ethyl | ethyl | 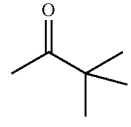 | | 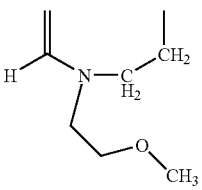 | crystalline |
| 3.29 | ethyl | ethyl | 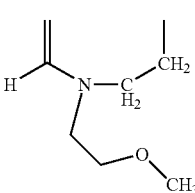 | —H | | solid |
| 3.30 | ethyl | ethyl | 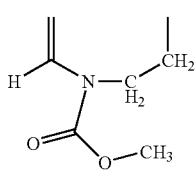 | —H | | solid |
| 3.31 | ethyl | ethyl | 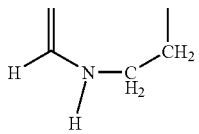 | | 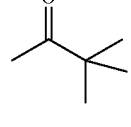 | |

TABLE 3-continued
Compounds of formula Ib:
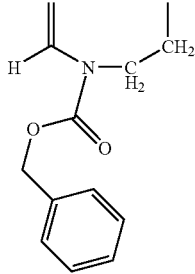
(Ib)
| 3.32 | ethyl | ethyl | 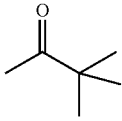 | —H | amorphous |
| No. | R₁ | R₃ | R₇ | R₆ | R₈ | G₂ | Physical data |
|-----|----|----|----|----|----|----|----|
| 3.33 | ethyl | ethyl | methyl | —(CH₂)₄— | | 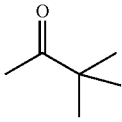 | |
| 3.34 | ethyl | ethyl | methyl | —(CH₂)₃— | | 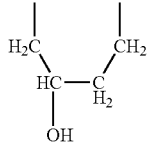 | |
| 3.35 | ethyl | ethyl | —H | 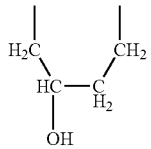 | | —H | |
| 3.36 | ethyl | ethyl | —H | 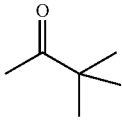 | | 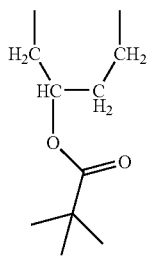 | |
| 3.37 | ethyl | ethyl | —H | 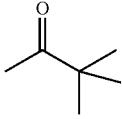 | | 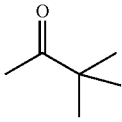 | |

TABLE 3-continued
Compounds of formula Ib:
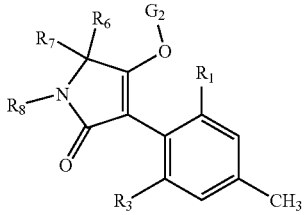
(Ib)
| | | | | | |
|---|---|---|---|---|---|
| 3.38 | ethyl | ethyl | —H | 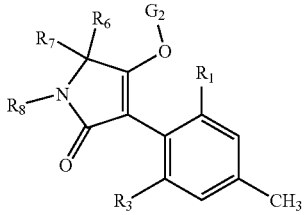 | —H |
| 3.39 | ethyl | ethyl | —H | 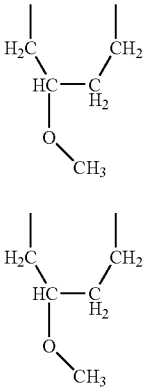 | 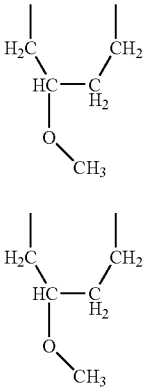 |
| 3.40 | ethyl | ethyl | —H | 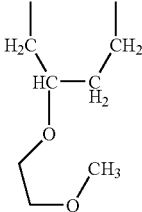 | —H |
| 3.41 | ethyl | ethyl | —H | 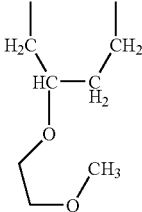 | 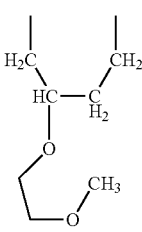 |
| 3.42 | ethyl | ethyl | —H | 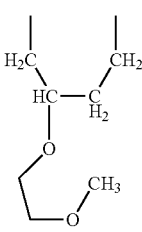 | —H |
| 3.43 | ethyl | ethyl | —H | 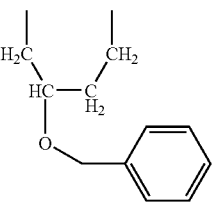 | 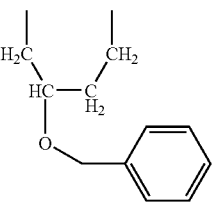 |

TABLE 3-continued
Compounds of formula Ib:
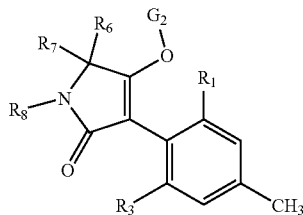
(Ib)
| 3.44 | ethyl | ethyl | —H | 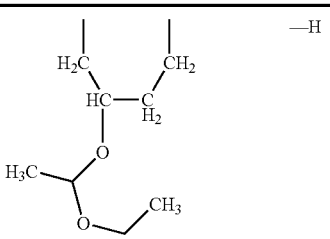 | —H |
| 3.45 | ethyl | ethyl | —H | 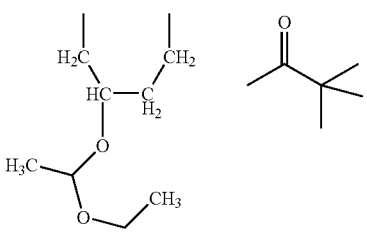 | (pivaloyl) |
TABLE 4
Compounds of formula Ic:
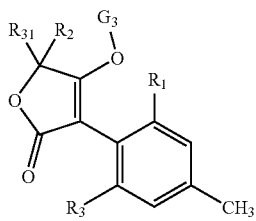
(Ic)
| No. | $R_1$ | $R_3$ | $R_2$ | $R_{31}$ | $G_3$ | Physical Data |
|---|---|---|---|---|---|---|
| 4.01 | ethyl | ethyl | methyl | methyl | —H | m.p. 224-226° C. |
| 4.02 | ethyl | ethyl | methyl | methyl | (pivaloyl) | m.p. 102-104° C. |
| 4.03 | ethyl | ethyl | methyl | ethyl | —H | |
| 4.04 | ethyl | ethynyl | methyl | methyl | —H | |
| 4.05 | ethyl | ethynyl | methyl | methyl | (pivaloyl) | |
| 4.06 | ethyl | methoxy | methyl | methyl | —H | |

TABLE 4-continued

Compounds of formula Ic:

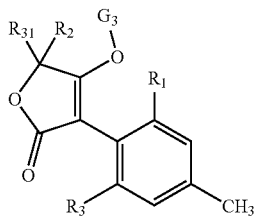

(Ic)

| No. | R$_1$ | R$_3$ | R$_2$ | R$_{31}$ | G$_3$ | Physical Data |
|---|---|---|---|---|---|---|
| 4.07 | ethyl | ethyl | —(CH$_2$)$_2$— | | —H | |
| 4.08 | ethyl | ethyl | —(CH$_2$)$_2$—CH(CH$_3$)—(CH$_2$)$_2$— | | ![ketone] | |
| 4.09 | ethyl | ethyl | —(CH$_2$)$_2$—C(CH$_3$)$_2$—(CH$_2$)$_2$— | | ![ketone] | |
| 4.10 | ethyl | ethyl | —(CH$_2$)4— | | —H | |
| 4.11 | ethyl | ethyl | —CH$_2$—CH$_2$—O—CH$_2$—CH$_2$— | | ![ketone] | |
| 4.12 | ethyl | ethyl | methyl | isopropyl | —H | |
| 4.13 | ethyl | ethyl | methyl | ethyl | —H | |
| 4.14 | ethyl | ethyl | methyl | n-butyl | ![ketone] | |
| 4.15 | ethyl | ethyl | methyl | H | ![ketone] | |
| 4.16 | ethyl | ethyl | —H | —H | —H | m.p. 176-178° C. |
| 4.17 | ethyl | ethyl | —H | —H | ![ketone] | m.p. 80-82° C. |
| 4.18 | OCH$_3$ | ethyl | —H | —H | —H | m.p. 169-171° C. |
| 4.19 | OCH$_3$ | ethyl | —H | —H | ![ketone] | oil |

TABLE 5

Compounds of formula Id:

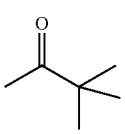

(Id)

| No. | R₁ | R₃ | R₃₂ | R₃₃ | G₄ | Physical data |
|---|---|---|---|---|---|---|
| 5.01 | ethyl | ethyl | methyl | methyl | —H | m.p. 181-183° C. |
| 5.02 | ethyl | ethyl | methyl | methyl | 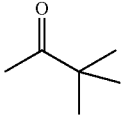 | oil |
| 5.03 | ethyl | ethyl | methyl | ethyl | —H | |
| 5.04 | ethyl | ethynyl | methyl | methyl | —H | |
| 5.05 | ethyl | ethynyl | methyl | methyl | 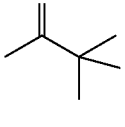 | |
| 5.06 | ethyl | methoxy | methyl | methyl | —H | |
| 5.07 | ethyl | ethyl | —(CH₂)₂— | | —H | |
| 5.08 | ethyl | ethyl | —(CH₂)₂—CH(CH₃)—(CH₂)₂— | | 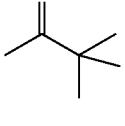 | |
| 5.09 | ethyl | ethyl | —(CH₂)₂—C(CH₃)₂—(CH₂)₂— | | 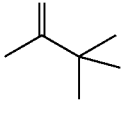 | |
| 5.10 | ethyl | ethyl | —(CH₂)₄— | | 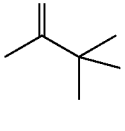 | |
| 5.11 | ethyl | ethyl | —CH₂—CH₂—O—CH₂—CH₂— | | 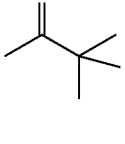 | |
| 5.12 | ethyl | ethyl | methyl | isopropyl | —H | |
| 5.13 | ethyl | ethyl | methyl | ethyl | —H | |
| 5.14 | ethyl | ethyl | methyl | n—butyl |  | |

TABLE 5-continued

Compounds of formula Id:

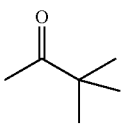

(Id)

| No. | $R_1$ | $R_3$ | $R_{32}$ | $R_{33}$ | $G_4$ | Physical data |
|---|---|---|---|---|---|---|
| 5.15 | ethyl | ethyl | methyl | H | ![pivaloyl] | |
| 5.16 | ethyl | ethyl | methyl | H | —H | oil |

TABLE 6

Compounds of formula Ie:

(Ie)

| No. | $R_1$ | $R_3$ | $R_9$ | $R_{10}$ | $R_{11}$ | $R_{12}$ | $G_5$ | Physical data |
|---|---|---|---|---|---|---|---|---|
| 6.01 | ethyl | ethyl | methyl | —H | methyl | —H | ![pivaloyl] | |
| 6.02 | ethyl | ethyl | methyl | methyl | —H | —H | ![pivaloyl] | |
| 6.03 | ethyl | ethyl | —(CH$_2$)$_2$— | | —H | —H | —H | |
| 6.04 | ethyl | ethyl | —(CH$_2$)$_4$— | | methyl | —H | —H | |
| 6.05 | ethyl | ethyl | —(CH$_2$)$_2$—O—(CH$_2$)$_2$— | | —H | —H | ![pivaloyl] | |
| 6.06 | ethyl | ethyl | —H | methyl | —(CH$_2$)$_4$— | | ![pivaloyl] | |

TABLE 6-continued

Compounds of formula Ie:

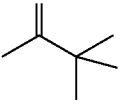

(Ie)

| No. | R$_1$ | R$_3$ | R$_9$ | R$_{10}$ | R$_{11}$ | R$_{12}$ | G$_5$ | Physical data |
|---|---|---|---|---|---|---|---|---|
| 6.07 | ethyl | ethyl | —H | | —O— | —H | 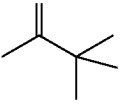 | |
| 6.08 | ethyl | ethyl | —H | | —CH$_2$— | —H | 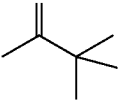 | |
| 6.09 | ethyl | ethynyl | —H | | —(CH$_2$)$_3$— | —H | 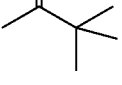 | |
| 6.10 | ethyl | MeO— | —H | | —(CH$_2$)$_4$— | —H | 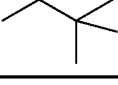 | |
| 6.11 | ethyl | ethynyl | —H | | —(CH$_2$)$_4$— | —H | 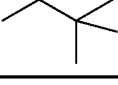 | |

TABLE 7

Compounds of formula If:

(If)

| No. | R$_1$ | R$_2$ | R$_{13}$ | R$_{14}$ | G$_6$ | Phys. data |
|---|---|---|---|---|---|---|
| 7.01 | ethyl | ethyl | methyl | methyl | —H | |
| 7.02 | ethyl | ethyl | methyl | —H | —H | |
| 7.03 | ethyl | ethyl | —H | methyl | —H | |
| 7.04 | ethyl | ethyl | ethyl | methyl | —H | |
| 7.05 | ethyl | ethyl | —(CH$_2$)$_4$— | | —H | |
| 7.06 | ethyl | MeO— | —(CH$_2$)$_4$— | | —H | |

TABLE 7-continued

Compounds of formula If:

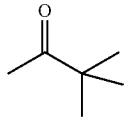

(If)

| No. | $R_1$ | $R_2$ | $R_{13}$ | $R_{14}$ | $G_6$ | Phys. data |
|---|---|---|---|---|---|---|
| 7.07 | ethyl | ethynyl | —(CH$_2$)$_4$— | |  | |
| 7.08 | ethyl | ethynyl | —(CH$_2$)$_3$— | —H | | |

TABLE 8

Compounds of formula Ig:

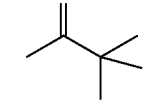

(Ig)

| No. | $R_1$ | $R_2$ | $R_{34}$ | $R_{35}$ | $G_7$ | Phys. data |
|---|---|---|---|---|---|---|
| 8.01 | ethyl | ethyl | methyl | methyl | —H | |
| 8.02 | ethyl | ethyl | methyl | —H | —H | |
| 8.03 | ethyl | ethyl | —H | methyl | —H | |
| 8.04 | ethyl | ethyl | ethyl | methyl | —H | |
| 8.05 | ethyl | ethyl | —(CH$_2$)$_4$— | | 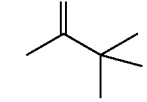 | |
| 8.06 | ethyl | ethyl | —(CH$_2$)$_3$— | | 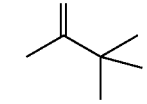 | |
| 8.07 | ethyl | ethynyl | methyl | methyl | 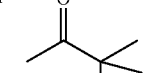 | |
| 8.08 | ethyl | methoxy | methyl | methyl | 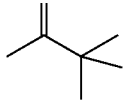 | |

TABLE 9

Compounds of formula Ih:

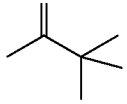

(Ih)

| No. | $R_1$ | $R_3$ | $R_{15}$ | $G_8$ | Physical data |
|---|---|---|---|---|---|
| 9.01 | ethyl | ethyl | methyl | —H | |
| 9.02 | ethyl | methoxy | phenyl | —H | |
| 9.03 | ethyl | ethynyl | —4-chloro-phenyl | —H | |
| 9.04 | ethyl | ethyl | ethyl | 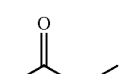 | |
| 9.05 | ethyl | ethyl | —OMe | 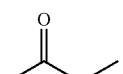 | |
| 9.06 | ethyl | ethyl | —CF$_3$ | | |
| 9.07 | ethyl | ethyl | isopropyl | 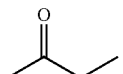 | |
| 9.08 | ethyl | ethyl | n-butyl | 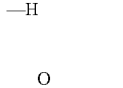 | |
| 9.09 | ethyl | ethyl | cyclopropyl | 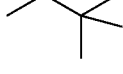 | |
| 9.10 | ethyl | ethyl | phenyl | —H | m.p. 208-209° C. |
| 9.11 | ethyl | ethyl | phenyl | 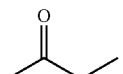 | m.p. 147-149° C. |
| 9.12 | ethyl | ethyl | —4-tert-butyl-phenyl | —H | m.p. 222-224° C. |
| 9.13 | ethyl | ethyl | —4-tert-butyl phenyl |  | amorphous |
| 9.14 | ethyl | ethyl | —4-tolyl | —H | |

TABLE 9-continued

Compounds of formula Ih:

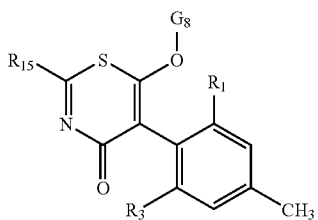

(Ih)

| No. | R₁ | R₃ | R₁₅ | G₈ | Physical data |
|---|---|---|---|---|---|
| 9.15 | ethyl | ethyl | —4-tolyl | ![pivaloyl] | |
| 9.16 | ethyl | ethyl | —3-chloro-4-fluorophenyl | —H | m.p. 186-188° C. |

TABLE 9-continued

Compounds of formula Ih:

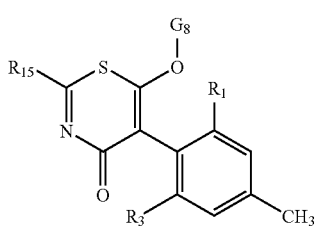

(Ih)

| No. | R₁ | R₃ | R₁₅ | G₈ | Physical data |
|---|---|---|---|---|---|
| 9.17 | ethyl | ethyl | —3-chloro-4-fluorophenyl | ![pivaloyl] | m.p. 109-110° C. |

TABLE 10

Compounds of formula Ik:

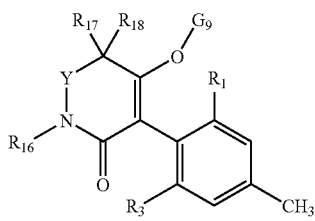

(Ik)

| No. | R₁ | R₃ | R₁₆ | Y | R₁₇ | R₁₈ | G₉ | Phys. data |
|---|---|---|---|---|---|---|---|---|
| 10.01 | ethyl | ethyl | methyl | O | methyl | —H | ![pivaloyl] | |
| 10.02 | ethyl | ethyl | methyl | O | methyl | methyl | ![pivaloyl] | |
| 10.03 | ethyl | ethyl | methyl | N—CH₃ | methyl | methyl | ![pivaloyl] | |
| 10.04 | ethyl | ethyl | methyl | (propyl)N | | —H | ![pivaloyl] | |

TABLE 10-continued

Compounds of formula Ik:

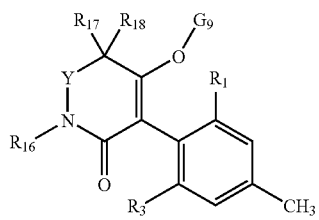

(Ik)

| No. | $R_1$ | $R_3$ | $R_{16}$ | Y | $R_{17}$ | $R_{18}$ | $G_9$ | Phys. data |
|---|---|---|---|---|---|---|---|---|
| 10.05 | ethyl | ethyl | methyl | —CH2— | methyl | methyl | pivaloyl | |
| 10.06 | ethyl | ethyl | methyl | —CH2— | methyl | —H | pivaloyl | |
| 10.07 | ethyl | ethyl | ethyl | —CH2— | —(CH2)2— | | pivaloyl | |
| 10.08 | ethyl | ethynyl | methyl | —CH2— | —H | methyl | pivaloyl | |
| 10.09 | ethyl | MeO— | methyl | —CH2— | methyl | methyl | pivaloyl | |
| 10.10 | ethyl | ethyl | methyl | O | methyl | —H | —H | |
| 10.11 | ethyl | ethyl | methyl | O | methyl | methyl | —H | |
| 10.12 | ethyl | ethyl | methyl | N—CH$_3$ | methyl | methyl | —H | |
| 10.13 | ethyl | ethyl | methyl | (piperidinyl) | | —H | —H | |
| 10.14 | ethyl | ethyl | methyl | —CH$_2$— | methyl | methyl | —H | |
| 10.15 | ethyl | ethyl | methyl | —CH$_2$— | methyl | —H | —H | |
| 10.16 | ethyl | ethyl | ethyl | —CH$_2$— | —(CH$_2$)$_2$— | | —H | |
| 10.17 | ethyl | ethynyl | methyl | —CH$_2$— | —H | methyl | —H | |
| 10.18 | ethyl | MeO— | methyl | —CH$_2$— | methyl | methyl | —H | |

In the following Table 21, Me is methyl, Et is ethyl, Pr is propyl and Bu is butyl:

TABLE 21

Compounds of formula Im:

(Im)

| Comp. No. | $R_1$ | $R_3$ | $R_{55}$ | $R_{137}$ | $R_{138}$ | $R_{139}$ | $Y_2$ | Phys. data |
|---|---|---|---|---|---|---|---|---|
| 21.1 | Et | Et | H | H | H | H | H | O |
| 21.2 | Et | ethynyl | H | H | H | H | H | O |
| 21.3 | Et | Et | Me | Me | Me | Me | H | O |
| 21.4 | Et | OMe | Me | Me | Me | Me | H | O |
| 21.5 | Et | Et | Me | H | H | H | H | O |
| 21.6 | ethynyl | Et | Me | H | H | H | H | O |
| 21.7 | Et | Et | H | H | Me | Me | H | O |
| 21.8 | OMe | Et | H | H | Me | Me | H | O |
| 21.9 | Et | Et | Me | H | Me | Me | H | O |
| 21.10 | Et | ethynyl | Me | H | Me | Me | H | O |
| 21.11 | Et | Et | H | Me | H | Me | H | O |
| 21.12 | Et | OMe | H | Me | H | Me | H | O |
| 21.13 | Et | Et | Me | Et | H | H | H | O |
| 21.14 | ethynyl | Et | Me | Et | H | H | H | O |
| 21.15 | Et | Et | H | Et | H | Et | H | O |
| 21.16 | OMe | Et | H | Et | H | Et | H | O |
| 21.17 | Et | Et | H | H | —(CH$_2$)$_4$— | | H | O |
| 21.18 | Et | ethynyl | H | H | —(CH$_2$)$_4$— | | H | O |
| 21.19 | Et | Et | H | H | H | H | COCMe$_3$ | O |
| 21.20 | Et | ethynyl | H | H | H | H | SO$_2$Me | O |
| 21.21 | Et | Et | Me | Me | Me | Me | COCMe$_3$ | O |
| 21.22 | Et | OMe | Me | Me | Me | Me | SO$_2$-n-Pr | O |
| 21.23 | Et | Et | Me | H | H | H | COCMe$_3$ | O |
| 21.24 | ethynyl | Et | Me | H | H | H | SO$_2$-n-Bu | O |
| 21.25 | Et | Et | H | H | Me | Me | COCMe$_3$ | O |
| 21.26 | OMe | Et | H | H | Me | Me | SO$_2$C$_8$H$_{17}$ | O |
| 21.27 | Et | Et | Me | H | Me | Me | COCMe$_3$ | O |
| 21.28 | Et | elhynyl | Me | H | Me | Me | SO$_2$Ph | O |
| 21.29 | Et | Et | H | Me | H | Me | COCMe$_3$ | O |
| 21.30 | Et | OMe | H | Me | H | Me | SO$_2$Me | O |
| 21.31 | Et | Et | Me | Et | H | H | COCMe$_3$ | O |
| 21.32 | ethynyl | Et | Me | Et | H | H | COCMe$_3$ | O |
| 21.33 | Et | Et | H | Et | H | Et | COCMe$_3$ | O |
| 21.34 | OMe | Et | H | Et | H | Et | COCMe$_3$ | O |
| 21.35 | Et | Et | H | H | —(CH$_2$)$_4$— | | COCMe$_3$ | O |
| 21.36 | Et | ethynyl | H | H | —(CH$_2$)$_4$— | | COCMe$_3$ | O |
| 21.37 | Et | Et | H | H | H | H | H | S |
| 21.38 | Et | ethynyl | H | H | H | H | H | S |
| 21.39 | Et | Et | Me | Me | Me | Me | H | S |
| 21.40 | Et | OMe | Me | Me | Me | Me | H | S |
| 21.41 | Et | Et | Me | H | H | H | H | S |
| 21.42 | ethynyl | Et | Me | H | H | H | H | S |
| 21.43 | Et | Et | H | H | Me | Me | H | S |
| 21.44 | OMe | Et | H | H | Me | Me | H | S |
| 21.45 | Et | Et | Me | H | Me | Me | H | S |
| 21.46 | Et | ethynyl | Me | H | Me | Me | H | S |
| 21.47 | Et | Et | H | Me | H | Me | H | S |
| 21.48 | Et | OMe | H | Me | H | Me | H | S |
| 21.49 | Et | Et | Me | Et | H | H | H | S |
| 21.50 | ethynyl | Et | Me | Et | H | H | H | S |
| 21.51 | Et | Et | H | Et | H | Et | H | S |
| 21.52 | OMe | Et | H | Et | H | Et | H | S |
| 21.53 | Et | Et | H | H | —(CH$_2$)$_4$— | | H | S |
| 21.54 | Et | ethynyl | H | H | —(CH$_2$)$_4$— | | H | S |
| 21.55 | Et | Et | H | H | H | H | COCMe$_3$ | S |
| 21.56 | Et | ethynyl | H | H | H | H | SO$_2$Me | S |
| 21.57 | Et | Et | Me | Me | Me | Me | COCMe$_3$ | S |
| 21.58 | Et | OMe | Me | Me | Me | Me | SO$_2$-n-Pr | S |
| 21.59 | Et | Et | Me | H | H | H | COCMe$_3$ | S |
| 21.60 | ethynyl | Et | Me | H | H | H | SO$_2$-n-Bu | S |

TABLE 21-continued

Compounds of formula Im:

$$\text{(Im)}$$

| Comp. No. | $R_1$ | $R_3$ | $R_{55}$ | $R_{137}$ | $R_{138}$ | $R_{139}$ | $Y_2$ | Phys. data |
|---|---|---|---|---|---|---|---|---|
| 21.61 | Et | Et | H | H | Me | Me | $COCMe_3$ | S |
| 21.62 | OMe | Et | H | H | Me | Me | $C_2C_8H_{17}$ | S |
| 21.63 | Et | Et | Me | H | Me | Me | $COCMe_3$ | S |
| 21.64 | Et | ethynyl | Me | H | Me | Me | $SO_2Ph$ | S |
| 21.65 | Et | Et | H | Me | H | Me | $COCMe_3$ | S |
| 21.66 | Et | OMe | H | Me | H | Me | $SO_2Me$ | S |
| 21.67 | Et | Et | Me | Et | H | H | $COCMe_3$ | S |
| 21.68 | ethynyl | Et | Me | Et | H | H | $COCMe_3$ | S |
| 21.69 | Et | Et | H | Et | H | Et | $COCMe_3$ | S |
| 21.70 | OMe | Et | H | Et | H | Et | $COCMe_3$ | S |
| 21.71 | Et | Et | H | H | —$(CH_2)_4$— | | $COCMe_3$ | S |
| 21.72 | Et | ethynyl | H | H | —$(CH_2)_4$— | | $COCMe_3$ | S |
| 21.73 | Et | Et | H | H | H | H | H | $NCH(CH_3)_2$ |
| 21.74 | Et | Et | H | H | H | H | H | $NCH_3$ |
| 21.75 | Et | Et | H | H | H | H | H | $NCH_2Ph$ |
| 21.76 | Et | ethynyl | H | H | H | H | H | $NCH_3$ |
| 21.77 | Et | Et | Me | Me | Me | Me | H | $NCH(CH_3)_2$ |
| 21.78 | Et | OMe | Me | Me | Me | Me | H | $NCH_3$ |
| 21.79 | Et | Et | Me | H | H | H | H | $NCH(CH_3)_2$ |
| 21.80 | ethynyl | Et | Me | H | H | H | H | $NCH_3$ |
| 21.81 | Et | Et | H | H | Me | Me | H | $NCH_3$ |
| 21.82 | OMe | Et | H | H | Me | Me | H | $NCH(CH_3)_2$ |
| 21.83 | Et | Et | Me | H | Me | Me | H | $NCH_2Ph$ |
| 21.84 | Et | ethynyl | Me | H | Me | Me | H | $NCH_3$ |
| 21.85 | Et | Et | H | Me | H | Me | H | $NCH_2Ph$ |
| 21.86 | Et | OMe | H | Me | H | Me | H | $NCH_3$ |
| 21.87 | Et | Et | Me | Et | H | H | H | $NCH(CH_3)_2$ |
| 21.88 | ethynyl | Et | Me | Et | H | H | H | $NCH_3$ |
| 21.89 | Et | Et | H | Et | H | Et | H | $NCH_2Ph$ |
| 21.90 | OMe | Et | H | Et | H | Et | H | $NCH(CH_3)_2$ |
| 21.91 | Et | Et | H | H | —$(CH_2)_4$— | | H | $NCH(CH_3)_2$ |
| 21.92 | Et | ethynyl | H | H | —$(CH_2)_4$— | | H | $NCH_3$ |
| 21.93 | OMe | Et | Et | Me | H | H | H | $NCH_3$ |
| 21.94 | Et | Et | H | H | H | H | $COCMe_3$ | $NCH(CH_3)_2$ |
| 21.95 | Et | Et | H | H | H | H | $SO_2Me$ | $NCH_3$ |
| 21.96 | Et | Et | H | H | H | H | $COCMe_3$ | $NCH_2Ph$ |
| 21.97 | Et | ethynyl | H | H | H | H | $SO_2$-n-Pr | $NCH_3$ |
| 21.98 | Et | Et | Me | Me | Me | Me | $COCMe_3$ | $NCH(CH_3)_2$ |
| 21.99 | Et | OMe | Me | Me | Me | Me | $SO_2$-n-Bu | $NCH_3$ |
| 21.100 | Et | Et | Me | H | H | H | $COCMe_3$ | $NCH(CH_3)_2$ |
| 21.101 | ethynyl | Et | Me | H | H | H | $SO_2C_8H_{17}$ | $NCH_3$ |
| 21.102 | Et | Et | H | H | Me | Me | $COCMe_3$ | $NCH_3$ |
| 21.103 | OMe | Et | H | H | Me | Me | $SO_2Ph$ | $NCH(CH_3)_2$ |
| 21.104 | Et | Et | Me | H | Me | Me | $COCMe_3$ | $NCH_2Ph$ |
| 21.105 | Et | ethynyl | Me | H | Me | Me | $SO_2Me$ | $NCH_3$ |
| 21.106 | Et | Et | H | Me | H | Me | $COCMe_3$ | $NCH_2Ph$ |
| 21.107 | Et | OMe | H | Me | H | Me | $COCMe_3$ | $NCH_3$ |
| 21.108 | Et | Et | Me | Et | H | H | $COCMe_3$ | $NCH(CH_3)_2$ |
| 21.109 | ethynyl | Et | Me | Et | H | H | $COCMe_3$ | $NCH_3$ |
| 21.110 | Et | Et | H | Et | H | Et | $COCMe_3$ | $NCH_2Ph$ |
| 21.111 | OMe | Et | H | Et | H | Et | $COCMe_3$ | $NCH(CH_3)_2$ |
| 21.112 | Et | Et | H | H | —$(CH_2)_4$— | | $COCMe_3$ | $NCH(CH_3)_2$ |
| 21.113 | Et | ethynyl | H | H | —$(CH_2)_4$— | | $SO_2C_8H_{17}$ | $NCH_3$ |
| 21.114 | OMe | Et | Et | Me | H | H | $SO_2$-n-Bu | $NCH_3$ |
| 21.115 | Et | Et | H | —$(CH_2)_2$— | H | H | H | $CH_2$ |
| 21.116 | Et | ethynyl | H | —$(CH_2)_2$— | H | H | H | $CH_2$ |
| 21.117 | Et | Et | —$(CH_2)_2$— | H | H | H | H | $CH_2$ |
| 21.118 | Et | OMe | —$(CH_2)_2$— | H | H | H | H | $CH_2$ |
| 21.119 | Et | Et | H | Me | Me | H | H | $CH_2$ |
| 21.120 | ethynyl | Et | H | Me | Me | H | H | $CH_2$ |
| 21.121 | Et | Et | Et | H | H | H | H | $CH_2$ |
| 21.122 | OMe | Et | Et | H | H | H | H | $CH_2$ |
| 21.123 | Et | Et | H | H | Me | Me | H | $CH_2$ |

TABLE 21-continued

Compounds of formula Im:

$$\text{(Im)}$$

| Comp. No. | $R_1$ | $R_3$ | $R_{55}$ | $R_{137}$ | $R_{138}$ | $R_{139}$ | $Y_2$ | Phys. data |
|---|---|---|---|---|---|---|---|---|
| 21.124 | Et | ethynyl | H | H | Me | Me | H | $CH_2$ |
| 21.125 | Et | Et | H | OMe | H | H | H | $CH_2$ |
| 21.126 | Et | OMe | H | OMe | H | H | H | $CH_2$ |
| 21.127 | Et | Et | H | —$(CH_2)_3$— | H | H | $CH_2$ | |
| 21.128 | ethynyl | Et | H | —$(CH_2)_3$— | H | H | $CH_2$ | |
| 21.129 | Et | Et | Me | H | Me | Me | H | $CH_2$ |
| 21.130 | OMe | Et | Me | H | Me | Me | H | $CH_2$ |
| 21.131 | Et | Et | Me | OMe | H | H | H | $CH_2$ |
| 21.132 | Et | ethynyl | Me | OMe | H | H | H | $CH_2$ |
| 21.133 | Et | Et | H | SMe | H | H | H | $CH_2$ |
| 21.134 | Et | OMe | H | SMe | H | H | H | $CH_2$ |
| 21.135 | Et | Et | Me | Me | Me | Me | H | $CH_2$ |
| 21.136 | ethynyl | Et | Me | Me | Me | Me | H | $CH_2$ |
| 21.137 | Et | Et | OH | Me | Me | Me | H | $CH_2$ |
| 21.138 | OMe | Et | OH | Me | Me | Me | H | $CH_2$ |
| 21.139 | Et | Et | Me | SMe | H | H | H | $CH_2$ |
| 21.140 | Et | ethynyl | Me | SMe | H | H | H | $CH_2$ |
| 21.141 | Et | Et | Et | Et | H | Me | H | $CH_2$ |
| 21.142 | Et | ethynyl | Et | Et | H | Me | H | $CH_2$ |
| 21.143 | Et | Et | Me | Me | H | $CH_2OMe$ | H | $CH_2$ |
| 21.144 | Et | OMe | Me | Me | H | $CH_2OMe$ | H | $CH_2$ |
| 21.145 | Et | ethynyl | Me | SMe | H | OMe | H | $CH_2$ |
| 21.146 | Et | Et | Me | SMe | H | OMe | H | $CH_2$ |
| 21.147 | Et | OMe | Me | SMe | H | OMe | H | $CH_2$ |
| 21.148 | Et | Et | H | —$(CH_2)_2$— | H | $COCMe_3$ | $CH_2$ | |
| 21.149 | Et | ethynyl | H | —$(CH_2)_2$— | H | $COCMe_3$ | $CH_2$ | |
| 21.150 | Et | Et | —$(CH_2)_2$— | H | H | $SO_2$-n-Pr | $CH_2$ | |
| 21.151 | Et | OMe | —$(CH_2)_2$— | H | H | $COCMe_3$ | $CH_2$ | |
| 21.152 | Et | Et | H | Me | Me | H | $COCMe_3$ | $CH_2$ |
| 21.153 | ethynyl | Et | H | Me | Me | H | $SO_2Me$ | $CH_2$ |
| 21.154 | Et | Et | Et | H | H | H | $COCMe_3$ | $CH_2$ |
| 21.155 | OMe | Et | Et | H | H | H | $SO_2$-n-Pr | $CH_2$ |
| 21.156 | Et | Et | H | H | Me | Me | $COCMe_3$ | $CH_2$ |
| 21.157 | Et | ethynyl | H | H | Me | Me | $SO_2$-n-Bu | $CH_2$ |
| 21.158 | Et | Et | H | OMe | H | H | $COCMe_3$ | $CH_2$ |
| 21.159 | Et | OMe | H | OMe | H | H | $SO_2C_8H_{17}$ | $CH_2$ |
| 21.160 | Et | Et | H | —$(CH_2)_3$— | H | $COCMe_3$ | $CH_2$ | |
| 21.161 | ethynyl | Et | H | —$(CH_2)_3$— | H | $COCMe_3$ | $CH_2$ | |
| 21.162 | Et | Et | Me | H | Me | Me | $SO_2$-n-Pr | $CH_2$ |
| 21.163 | OMe | Et | Me | H | Me | Me | $COCMe_3$ | $CH_2$ |
| 21.164 | Et | Et | Me | OMe | H | H | $COCMe_3$ | $CH_2$ |
| 21.165 | Et | ethynyl | Me | OMe | H | H | $SO_2Me$ | $CH_2$ |
| 21.166 | Et | Et | H | SMe | H | H | $COCMe_3$ | $CH_2$ |
| 21.167 | Et | OMe | H | SMe | H | H | $SO_2$-n-Pr | $CH_2$ |
| 21.168 | Et | Et | Me | Me | Me | Me | $COCMe_3$ | $CH_2$ |
| 21.169 | ethynyl | Et | Me | Me | Me | Me | $SO_2$-n-Bu | $CH_2$ |
| 21.170 | Et | Et | CH | Me | Me | Me | $COCMe_3$ | $CH_2$ |
| 21.171 | OMe | Et | CH | Me | Me | Me | $SO_2C_8H_{17}$ | $CH_2$ |
| 21.172 | Et | Et | Me | SMe | H | H | $COCMe_3$ | $CH_2$ |
| 21.173 | Et | ethynyl | Me | SMe | H | H | $COCMe_3$ | $CH_2$ |
| 21.174 | Et | Et | Et | Et | H | Me | $COCMe_3$ | $CH_2$ |
| 21.175 | Et | ethynyl | Et | Et | H | Me | $SO_2C_8H_{17}$ | $CH_2$ |
| 21.176 | Et | Et | Me | Me | H | $CH_2OMe$ | $SO_2$-n-Pr | $CH_2$ |
| 21.177 | Et | OMe | Me | Me | H | $CH_2OMe$ | $COCMe_3$ | $CH_2$ |
| 21.178 | Et | ethynyl | Me | SMe | H | OMe | $COCMe_3$ | $CH_2$ |
| 21.179 | Et | Et | Me | SMe | H | OMe | $SO_2C_8H_{17}$ | $CH_2$ |
| 21.180 | Et | OMe | Me | SMe | H | OMe | $COOMe_3$ | $CH_2$ |
| 21.181 | Et | Et | H | —$(CH_2)_2$— | H | H | $CHCH_3$ | |
| 21.182 | Et | ethynyl | H | —$(CH_2)_2$— | H | H | $CHCH_3$ | |
| 21.183 | Et | Et | —$(CH_2)_2$— | H | H | H | $CHCH_3$ | |
| 21.184 | Et | OMe | —$(CH_2)_2$— | H | H | H | $CHCH_3$ | |
| 21.185 | Et | Et | H | Me | Me | H | H | $CHCH_3$ |
| 21.186 | ethynyl | Et | H | Me | Me | H | H | $CHCH_3$ |

TABLE 21-continued

Compounds of formula Im:

(Im)

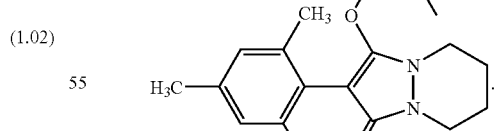

| Comp. No. | $R_1$ | $R_3$ | $R_{55}$ | $R_{137}$ | $R_{138}$ | $R_{139}$ | $Y_2$ | Phys. data |
|---|---|---|---|---|---|---|---|---|
| 21.187 | Et | Et | Et | H | H | H | H | $CHCH_3$ |
| 21.188 | OMe | Et | Et | H | H | H | H | $CHCH_3$ |
| 21.189 | Et | Et | H | H | Me | Me | H | $CHCH_3$ |
| 21.190 | Et | ethynyl | H | H | Me | Me | H | $CHCH_3$ |
| 21.191 | Et | Et | H | —(CH$_2$)$_2$— | H | $COCMe_3$ | $CHCH_3$ |
| 21.192 | Et | ethynyl | H | —(CH$_2$)$_2$— | H | $COCMe_3$ | $CHCH_3$ |
| 21.193 | Et | Et | —(CH$_2$)$_2$— | H | H | $SO_2$-n-Pr | $CHCH_3$ |
| 21.194 | Et | OMe | —(CH$_2$)$_2$— | H | H | $COCMe_3$ | $CHCH_3$ |
| 21.195 | Et | Et | H | Me | Me | H | $COCMe_3$ | $CHCH_3$ |
| 21.196 | ethynyl | Et | H | Me | Me | H | $SO_2Me$ | $CHCH_3$ |
| 21.197 | Et | Et | Et | H | H | H | $COCMe_3$ | $CHCH_3$ |
| 21.198 | OMe | Et | Et | H | H | H | $SO_2$-n-Pr | $CHCH_3$ |
| 21.199 | Et | Et | H | H | Me | Me | $COCMe_3$ | $CHCH_3$ |
| 21.200 | Et | ethynyl | H | H | Me | Me | $SO_2$-n-Bu | $CHCH_3$ |
| 21.201 | Et | Et | H | —(CH$_2$)$_2$— | H | H | $C(CH_3)_2$ |
| 21.202 | Et | ethynyl | H | —(CH$_2$)$_2$— | H | H | $C(CH_3)_2$ |
| 21.203 | Et | Et | —(CH$_2$)$_2$— | H | H | H | $C(CH_3)_2$ |
| 21.204 | Et | OMe | —(CH$_2$)$_2$— | H | H | H | $C(CH_3)_2$ |
| 21.205 | Et | Et | H | Me | Me | H | H | $C(CH_3)_2$ |
| 21.206 | ethynyl | Et | H | Me | Me | H | H | $C(CH_3)_2$ |
| 21.207 | Et | Et | Et | H | H | H | H | $C(CH_3)_2$ |
| 21.208 | OMe | Et | Et | H | H | H | H | $C(CH_3)_2$ |
| 21.209 | Et | Et | H | —(CH$_2$)$_2$— | H | $COCMe_3$ | $C(CH_3)_2$ |
| 21.210 | Et | ethynyl | H | —(CH$_2$)$_2$— | H | $COCMe_3$ | $C(CH_3)_2$ |
| 21.211 | Et | Et | —(CH$_2$)$_2$— | H | H | $SO_2$-n-Pr | $C(CH_3)_2$ |
| 21.212 | Et | OMe | —(CH$_2$)$_2$— | H | H | $COCMe_3$ | $C(CH_3)_2$ |
| 21.213 | Et | Et | H | Me | Me | H | $COCMe_3$ | $C(CH_3)_2$ |
| 21.214 | ethynyl | Et | H | Me | Me | H | $SO_2Me$ | $C(CH_3)_2$ |
| 21.215 | Et | Et | Et | H | H | H | $COCMe_3$ | $C(CH_3)_2$ |
| 21.216 | OMe | Et | Et | H | H | H | $SO_2$-n-Pr | $C(CH_3)_2$ |
| 21.217 | Et | Et | Me | Me | Me | Me | H | $CHCO_2Me$ |
| 21.218 | Et | Et | H | H | H | H | H | $CHCO_2Me$ |
| 21.219 | Et | Et | Me | Me | Me | Me | $COCMe_3$ | $CHCO_2Me$ |
| 21.220 | Et | Et | H | H | H | H | $COCMe_3$ | $CHCO_2Me$ |
| 21.221 | Et | OMe | —(CH$_2$)$_2$— | H | H | H | $CHCO_2Me$ |
| 21.222 | Et | OMe | —(CH$_2$)$_2$— | H | H | $COCMe_3$ | $CHCO_2Me$ |

BIOLOGICAL EXAMPLES

Comparison Test:

The following compounds were tested for their herbicidal action: compound no. 1.02

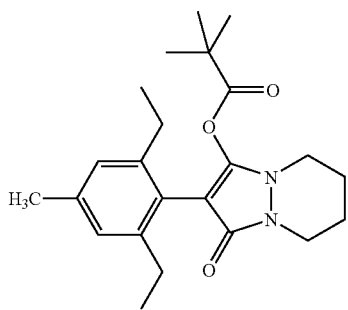

(1.02)

according to the present invention, and compound A (compound A)

Example B1

Herbicidal Action Prior to Emergence of the Plants (Pre-emergence Action)

Monocotyledonous and dicotyledonous weeds are sown in plastics pots in standard soil. Immediately after sowing, the-test substances are applied in the form of an aqueous suspension (prepared from a 25% wettable powder (Example F3,b)) or in the form of an emulsion (prepared from a 25% emulsifiable concentrate (Example F1, c)) (500 litres of water/ha). The rate of application is 500 g of active substance/ha. The test plants are then grown in the greenhouse under optimum conditions. The evaluation is carried out 3 weeks after application, using a scale of nine ratings (1=total damage, 9=no action). Ratings of from 1 to 4 (especially from 1 to 3) indicate good to very good herbicidal action. Test plants: *Alopecurus* (Alo), *Avena* (Ave), *Lolium* (Lol), *Setaria* (Set), *Panicum* (Pan), *Sorghum* (Sor), *Digitaria* (Dig), *Echinocloa* (Ech) and *Brachiaria* (Bra).

TABLE B1

Pre-emergence action:
Pre-emergence action at 500 g of active ingredient/ha

| Comp. No. | Alo | Ave | Lol | Set | Pan | Sor | Dig | Ech | Bra |
|---|---|---|---|---|---|---|---|---|---|
| compound A | 2 | 4 | 1 | 2 | 1 | 4 | 4 | 5 | 3 |
| 1.02 | 1 | 1 | 1 | 1 | 1 | 1 | 4 | 1 | 1 |

Example B2

Herbicidal Action After Emergence of the Plants (Post-emergence Action)

Monocotyledonous and dicotyledonous weeds are grown in standard soil in plastics pots under greenhouse conditions. The test substances are applied to the test plants at the 3- to 6-leaf stage. The test substances are applied at a rate of application of 500 g of active substance per hectare in the form of an aqueous suspension (prepared from a 25% wettable powder (Example F3, b)) or in the form of an emulsion (prepared from a 25% emulsifiable concentrate (Example F1, c)) (500 litres of water/ha). The evaluation is carried out 3 weeks after application, using a scale of nine ratings (1=total damage, 9=no action). Ratings of from 1 to 4 (especially from 1 to 3) indicate good to very good herbicidal action. Test plants: *Alopecurus* (Alo), *Avena* (Ave), *Lolium* (Lol), *Setaria* (Set), *Panicum* (Pan), *Sorghum* (Sor), *Digitaria* (Dig), *Echinocloa* (Ech) and *Brachiaria* (Bra).

TABLE B2

Post-emergence action:
Post-emergence action at 250 g of active ingredient/ha

| Comp. No. | Alo | Ave | Lol | Set | Pan | Sor | Dig | Ech | Bra |
|---|---|---|---|---|---|---|---|---|---|
| compound A | 3 | 3 | 2 | 2 | 1 | 3 | 2 | 1 | 2 |
| 1.02 | 1 | 1 | 1 | 1 | 1 | 1 | 2 | 1 | 1 |

By comparing the herbicidal activity of compound A with compound no. 1.02 of the present invention, it can be seen that, in the case of all weeds tested, compound no. 1.02 surprisingly exhibits an appreciably improved herbicidal action, although the only difference between that compound and compound A is that two ethyl groups have been replaced by methyl groups.

Example B3

Herbicidal Action Prior to the Emergence of the Plants (Pre-emergence Action) of Compounds of the Present Invention Monocotyledonous and dicotyledonous weeds are sown in standard soil in plastics pots. Immediately after sowing, the test substances are applied in the form of an aqueous suspension (prepared from a 25% wettable powder (Example F3, b)) or in the form of an emulsion (prepared from a 25% emulsifiable concentrate (Example F1, c)) (500 litres of water/ha). The rate of application is 500 g of active substance/ha. The test plants are then grown in the greenhouse under optimum conditions, The evaluation is carried out 3 weeks after application, using a scale of nine ratings (1=total damage, 9=no action). Ratings of from 1 to 4 (especially from 1 to 3) indicate good to very good herbicidal action. Test plants: *Avena* (Ave), *Lolium* (Lol), *Setaria* (Set).

TABLE B3

Pre-emergence action: MERGE ® is used as oil additive in a concentration of 0.7% by weight of the spray mixture

|  | Test plant: | | |
|---|---|---|---|
| Comp. No. | Ave | Lol | Set |
| 1.01 | 1 | 1 | 1 |
| 1.02 | 1 | 1 | 1 |
| 1.31 | 1 | 1 | 2 |
| 1.35 | 1 | 1 | 1 |

The same results are obtained when the compounds of formula I are formulated in accordance with Examples F2 and F4 to F8.

Example B4

Herbicidal Action After the Emergence of the Plants (Post-emergence Action) of Compounds of the Present Invention (for Description See Example B2)

Test plants: *Avena* (Ave), *Lolium* (Lol), *Setaria* (Set). The results are given in the following Table B4:

TABLE B4

Post-emergence action: MERGE ® is used as oil additive in a concentration of 0.7% by weight of the spray mixture.

|  | Test plant: | | |
|---|---|---|---|
| Comp. No. | Ave | Lol | Set |
| 1.01 | 1 | 1 | 1 |
| 1.02 | 1 | 1 | 1 |
| 1.04 | 1 | 1 | 1 |
| 1.05 | 1 | 3 | 1 |
| 1.07 | 1 | 1 | 1 |
| 1.08 | 1 | 1 | 1 |
| 1.10 | 1 | 1 | 1 |
| 1.11 | 1 | 1 | 1 |
| 1.14 | 1 | 2 | 2 |
| 1.15 | 1 | 2 | 1 |
| 1.17 | 1 | 1 | 2 |
| 1.19 | 1 | 1 | 1 |

TABLE B4-continued

Post-emergence action: MERGE ® is used as oil additive in a concentration of 0.7% by weight of the spray mixture.

| Comp. No. | Test plant: | | |
|---|---|---|---|
| | Ave | Lol | Set |
| 1.21 | 1 | 1 | 1 |
| 1.23 | 1 | 1 | 1 |
| 1.26 | 1 | 2 | 1 |
| 1.27 | 1 | 1 | 2 |
| 1.30 | 1 | 1 | 1 |
| 1.31 | 1 | 1 | 1 |
| 1.35 | 1 | 1 | 1 |
| 1.37 | 1 | 1 | 1 |
| 1.39 | 1 | 1 | 1 |
| 1.40 | 1 | 1 | 2 |
| 1.43 | 1 | 2 | 2 |

The same results are obtained when the compounds of formula I are formulated in accordance with Examples F2 and F4 to F8.

The invention claimed is:

1. A compound of formula I

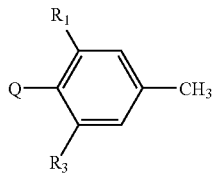

(I)

wherein $R_1$ and $R_3$ are each independently of the other ethyl, haloethyl, ethynyl, $C_1$-$C_2$alkoxy, $C_1$-$C_2$haloalkoxy, $C_1$-$C_2$alkylcarbonyl, $C_1$-$C_2$hydroxyalkyl or $C_1$-$C_2$alkoxycarbonyl;

Q is a group

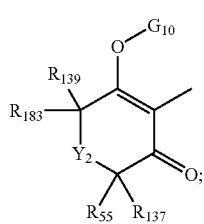

($Q_{10}$)

$G_{10}$ is hydrogen, —C($X_1$)—$R_{20}$, —C($X_2$)—$X_3$—$R_{21}$, —C($X_4$)—N($R_{22}$)—$R_{23}$, —SO$_2$—$R_{24}$, an alkali metal cation, alkaline earth metal cation, sulfonium cation or ammonium cation, —P($X_5$)($R_{25}$)—$R_{26}$ or —CH$_2$—$X_6$—$R_{27}$;

$X_1$, $X_2$, $X_3$, $X_4$, $X_5$ and $X_6$ are each independently of the others oxygen or sulfur;

$R_{20}$, $R_{21}$, $R_{22}$ and $R_{23}$ are each independently of the others hydrogen, $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfoxyl-$C_1$-$C_5$alkyl, $C_1$-$C_5$alkylsulfonyl-$C_1$-$C_5$alkyl, $C_2$-$C_8$alkylideneaminooxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$aminocarbonyl-$C_1$-$C_5$alkyl, $C_2$-$C_8$dialkylaminocarbonyl-$C_1$-$C_5$alkyl, $C_1$-$C_5$alkylcarbonylamino-$C_1$-$C_5$alkyl, $C_1$-$C_5$alkylcarbonyl-($C_2$-$C_5$alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino, or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, phenylamino, or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or $C_3$-$C_7$cycloalkylamino, di-$C_3$-$C_7$cycloalkylamino or $C_3$-$C_7$cycloalkoxy;

$R_{24}$, $R_{25}$ and $R_{26}$ are hydrogen, $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkyl-amino-$C_1$-$C_5$alkyl, $C_3$-$C_7$cycloalkyl-$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfoxyl-$C_1$-$C_5$alkyl, $C_1$-$C_5$alkylsulfonyl-$C_1$-$C_5$alkyl, $C_2$-$C_8$alkylideneaminooxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$aminocarbonyl-$C_1$-$C_5$alkyl, $C_2$-$C_8$dialkylaminocarbonyl-$C_1$-$C_5$alkyl, $C_1$-$C_5$alkylcarbonyl-amino-$C_1$-$C_5$alkyl, $C_1$-$C_5$alkylcarbonyl-($C_2$-$C_5$alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino, or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, phenylamino, or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or $C_3$-$C_7$cycloalkylamino, di-$C_3$-$C_7$cyclo-alkylamino, $C_3$-$C_7$cycloalkoxy, $C_1$-$C_{10}$alkoxy, $C_1$-$C_{10}$haloalkoxy, $C_1$-$C_5$alkylamino, $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or by nitro;

$R_{27}$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxyalkyl, $C_4$-$C_{10}$alkenyloxyalkyl, $C_4$-$C_{10}$alkynyloxyalkyl, $C_2$-$C_{10}$alkylthioalkyl, $C_1$-$C_5$alkylsulfoxyl-$C_1$-$C_5$alkyl, $C_1$-$C_5$alkylsulfonyl-$C_1$-$C_5$alkyl, $C_2$-$C_8$alkylideneaminooxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$aminocarbonyl-$C_1$-$C_5$alkyl, $C_2$-$C_8$dialkylaminocarbonyl-$C_1$-$C_5$alkyl, $C_1$-$C_5$alkylcarbonylamino-$C_1$-$C_5$alkyl, $C_1$-$C_5$alkylcarbonyl-($C_2$-$C_5$alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or phenyl substituted by $C_1$-$C_3$alkyl, $C_1$-$C_3$haloalkyl, $C_1$-$C_3$alkoxy, $C_1$-$C_3$haloalkoxy, halogen, cyano or by nitro, or heteroaryl or heteroarylamino, or heteroaryl or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino, diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, or phenylamino, phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino, diphenyl-amino substituted by $C_1$-$C_3$alkyl, $C_1$-$C_3$haloalkyl, $C_1$-$C_3$alkoxy, $C_1$-$C_3$haloalkoxy, halogen, cyano or by nitro, $C_3$-$C_7$cycloalkylamino, di-$C_3$-$C_7$cycloalkylamino, $C_3$-$C_7$cycloalkoxy or $C_1$-$C_{10}$alkylcarbonyl;

$Y_2$ is oxygen, $R_{55}$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_2$-$C_{10}$alkylcarbonylalkyl, $C_3$-$C_{10}$cycloalkyl, aryl or heteroaryl;

$R_{137}$ is hydrogen, $C_1$-$C_{10}$alkyl, $C_2C_{10}$alkenyl, $C_2$-$C_{10}$alkynyl or $C_1$-$C_{10}$alkoxyalkyl; or $R_{55}$ and $R_{137}$, together with the atoms to which they are bonded, form a 3- to 7-membered cyclic group that may contain one or two hetero atoms selected from nitrogen, oxygen and sulfur;

$R_{138}$ and $R_{139}$ are each independently of the other hydrogen, $C_1$-$C_{10}$alkyl, $C_2$-$C_{10}$alkenyl, $C_2$-$C_{10}$alkynyl or $C_2$-$C_{10}$alkoxyalkyl; and $R_{140}$ and $R_{141}$ are each independently of the other hydrogen, $C_1$-$C_{10}$alkyl, $C_2$-$C_{10}$alkenyl, $C_2$-$C_{10}$alkynyl or $C_1$-$C_{10}$alkoxyalkyl; or $R_{55}$ and C—$R_{140}$, together with the atoms to which they are bonded, form a saturated or unsaturated 3- to 7-membered cyclic group that may contain one or two hetero atoms selected from nitrogen, oxygen and sulfur;

$R_{142}$ is hydrogen, $C_1$-$C_{10}$alkyl, $C_1$-$C_{10}$haloalkyl, $C_2$-$C_{10}$alkoxyalkyl, $C_3$-$C_{10}$alkenyloxyalkyl, $C_3$-$C_{10}$alkynyloxyalkyl, $C_2$-$C_{10}$alkylthioalkyl, $C_2$-$C_{10}$alkylsulfinylalkyl, $C_2$-$C_{10}$alkylsulfonylalkyl, $C_3$-$C_{10}$cycloalkyl, aryl or heteroaryl; or $R_{55}$ and N—$R_{142}$, together with the atoms to which they are bonded, form a saturated or unsaturated 3 to 7-membered cyclic group that may contain one or two hetero atoms selected from nitrogen, oxygen and sulfur;

or an agronomically tolerable salt, isomer or enantiomer of such a compound.

2. A process for the preparation of a compound of formula I according to claim 1, wherein a compound of formula XXX

Q-H (XXX)

wherein Q is $Q_{10}$, as defined in claim 1, the substituents of which, have the meanings as defined in claim 1, is reacted with a compound of formula XXXI

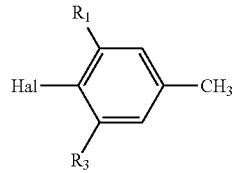

(XXXI)

wherein $R_1$ and $R_3$ are as defined in claim 1 and Hal is chlorine, bromine or iodine, in the presence of an inert solvent, a base and a palladium catalyst at temperatures of from 30 to 250° C.

3. A herbicidal and plant growth-inhibiting composition that comprises a herbicidally effective amount of a compound of formula I as defined in claim 1 on an inert carrier.

4. A method of controlling undesired plant growth that comprises applying an herbicidally effective amount of an active ingredient of formula I as defined in claim 1, or of a composition comprising such an active ingredient, to the plants or to the locus thereof.

5. A method of inhibiting plant growth that comprises applying a herbicidally effective amount of an active ingredient of formula I, or of a composition comprising such an active ingredient, to the plants or to the locus thereof.

* * * * *